(12) United States Patent
Paone et al.

(10) Patent No.: US 7,994,325 B2
(45) Date of Patent: Aug. 9, 2011

(54) CGRP RECEPTOR ANTAGONISTS

(75) Inventors: Daniel V. Paone, Lansdale, PA (US);
Diem N. Nguyen, Harleysville, PA (US);
Anthony W. Shaw, Harleysville, PA (US);
Christopher S. Burgey, Philadelphia, PA (US);
Thomas J. Tucker, North Wales, PA (US);
Samuel L. Graham, Schwenksville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 991 days.

(21) Appl. No.: 11/885,926

(22) PCT Filed: Mar. 14, 2006

(86) PCT No.: PCT/US2006/008859
§ 371 (c)(1),
(2), (4) Date: Sep. 6, 2007

(87) PCT Pub. No.: WO2006/099268
PCT Pub. Date: Sep. 21, 2006

(65) Prior Publication Data
US 2008/0261972 A1 Oct. 23, 2008

Related U.S. Application Data

(60) Provisional application No. 60/661,565, filed on Mar. 14, 2005.

(51) Int. Cl.
*A61K 31/444* (2006.01)
*C07D 211/86* (2006.01)

(52) U.S. Cl. ......... 546/193; 546/198; 546/199; 514/318

(58) Field of Classification Search .................. 546/193, 546/198, 199; 514/318
See application file for complete search history.

(56) References Cited

U.S. PATENT DOCUMENTS

| | | | |
|---|---|---|---|
| 6,953,790 B2 * | 10/2005 | Burgey et al. | 514/212.08 |
| 7,452,903 B2 * | 11/2008 | Burgey et al. | 514/303 |
| 7,491,713 B2 * | 2/2009 | Burgey et al. | 514/211.03 |
| 7,534,784 B2 * | 5/2009 | Burgey et al. | 514/212.08 |
| 7,772,224 B2 * | 8/2010 | Paone et al. | 514/211.04 |

FOREIGN PATENT DOCUMENTS

| | | |
|---|---|---|
| WO | WO2004091514 A2 | 10/2004 |
| WO | WO2004092166 A2 | 10/2004 |
| WO | WO2005072308 A2 | 8/2005 |

OTHER PUBLICATIONS

Database Caplus on STN: Synthesis and N-substitution of an uncommon heterocyclic system DN 117: 212370. Tetrahedron Letters Issue 32, vol. 33, p. 457104, 1992, Flouzat, et al. English Abstract.
Database CA Online, 1978, Fujita Hiroshi, et al., XP002577480, Accession No. 1978:443299, Compounds with RN 66697-49-2 and 66697-50-5, & 1977, Sankyo Kenkyusko Nenpo, 29, 75-98, CODEN: SKKNAJ: ISSN: 0080-6064.
Nguyen, et al., Bioorganic & Medicinal Chemistry Letters, Pergamon, Elsevier Science, GB LNKD-DOI: 10.1016/J/BMCL. 2007.11.042, vol. 18, No. 2, 2007, pp. 755-758, XP022424742, ISSN: 0960-894X.
European Search Report and Search Opinion dated May 7, 2010 for counterpart European Application No. 06748359.4.

* cited by examiner

*Primary Examiner* — Rita Desai
(74) *Attorney, Agent, or Firm* — Gerard Devlin; Raynard Yuro

(57) ABSTRACT

Compounds of Formula I:

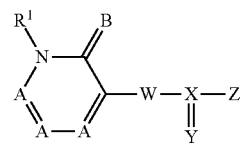

(where variables $R^1$, A, B, W, X, Y and Z are as defined herein) useful as antagonists of CGRP receptors and useful in the treatment or prevention of diseases in which the CGRP is involved, such as headache, migraine and cluster headache. The invention is also directed to pharmaceutical compositions comprising these compounds and the use of these compounds and compositions in the prevention or treatment of such diseases in which CGRP is involved.

7 Claims, No Drawings

CGRP RECEPTOR ANTAGONISTS

CROSS-REFERENCE TO RELATED APPLICATIONS

This application claims priority under 35 U.S.C. §119(e) of U.S. provisional application Ser. No. 60/661,565, filed Mar. 14, 2005.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

Based on pharmacological properties, these receptors are divided into at least two subtypes, denoted $CGRP_1$ and $CGRP_2$. Human α-CGRP-(8-37), a fragment of CGRP that lacks seven N-terminal amino acid residues, is a selective antagonist of $CGRP_1$, whereas the linear analogue of CGRP, diacetoamido methyl cysteine CGRP ([Cys(ACM)2,7] CGRP), is a selective agonist of $CGRP_2$. CGRP is a potent vasodilator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183-187). CGRP activates receptors on the smooth muscle of intracranial vessels, leading to increased vasodilation, which is thought to be the major source of headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193-196). Electrical stimulation of the dura matter in rats increased the diameter of the middle meningeal artery, an effect that was blocked by prior administration of CGRP(8-37), a peptide CGRP antagonist (Williamson et al., Cephalalgia, 1997, 17, 525-531). Trigeminal ganglion stimulation increased facial blood flow in the rat, which was inhibited by CGRP(8-37) (Escott et al., Brain Res. 1995, 669, 93-99). Electrical stimulation of the trigeminal ganglion in marmoset produced an increase in facial blood flow that could be blocked by the non-peptide CGRP antagonist BIBN4096BS (Doods et al., Br. J. Pharmacol., 2000, 129, 420-423). Thus the vascular effects of CGRP may be attenuated, prevented or reversed by a CGRP antagonist.

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al., Ann. Neurol. 2000, 47, 614-624). A CGRP antagonist may be beneficial in attenuating, preventing or reversing the effects of neuronal sensitization.

The ability of the compounds of the present invention to act as CGRP antagonists makes them useful pharmacological agents for disorders that involve CGRP in humans and animals, but particularly in humans. Such disorders include migraine and cluster headache (Doods, Curr Opin Inves Drugs, 2001, 2 (9), 1261-1268; Edvinsson et al., Cephalalgia, 1994, 14, 320-327); chronic tension type headache (Ashina et al., Neurology, 2000, 14, 1335-1340); pain (Yu et al., Eur. J. Pharm., 1998, 347, 275-282); chronic pain (Hulsebosci et al., Pain, 2000, 86, 163-175); neurogenic inflammation and inflammatory pain (Holzer, Neurosci., 1988, 24, 739-768; Delay-Goyet et al., Acta Physiol. Scanda. 1992, 146, 537-538; Salmon et al., Nature Neurosci., 2001, 4(4), 357-358); eye pain (May et al. Cephalalgia, 2002, 22, 195-196), tooth pain (Awawdeh et al., Int. Endocrin. J., 2002, 35, 30-36), non-insulin dependent diabetes mellitus (Molina et al., Diabetes, 1990, 39, 260-265); vascular disorders; inflammation (Zhang et al., Pain, 2001, 89, 265), arthritis, bronchial hyperreactivity, asthma, (Foster et al., Ann. NY Acad. Sci., 1992, 657, 397-404; Schini et al., Am. J. Physiol., 1994, 267, H2483-H2490; Zheng et al., J. Virol., 1993, 67, 5786-5791); shock, sepsis (Beer et al., Crit. Care Med., 2002, 30 (8), 1794-1798); opiate withdrawal syndrome (Salmon et al., Nature Neurosci., 2001, 4(4), 357-358) morphine tolerance (Menard et al., J. Neurosci., 1996, 16 (7), 2342-2351); hot flashes in men and women (Chen et al., Lancet, 1993, 342, 49; Spetz et al., J. Urology, 2001, 166, 1720-1723); allergic dermatitis (Wallengren, Contact Dermatitis, 2000, 43 (3), 137-143); psoriasis; encephalitis, brain trauma, ischaemia, stroke, epilepsy, and neurodegenerative diseases (Robrenbeck et al., Neurobiol. of Disease 1999, 6, 15-34); skin diseases (Geppetti and Holzer, Eds., Neurogenic Inflammation, 1996, CRC Press, Boca Raton, Fla.), neurogenic cutaneous redness, skin rosaceousness and erythema; tinnitus (Herzog et al., J. Membrane Biology, 2002, 189(3), 225); inflammatory bowel disease, irritable bowel syndrome, (Hoffman et al. Scandinavian Journal of Gastroenterology, 2002, 37(4) 414-422) and cystitis. Of particular importance is the acute or prophylactic treatment of headache, including migraine and cluster headache. Compelling evidence of the efficacy of CGRP antagonists for the treatment of migraine has been provided by clinical studies using intravenously administered BIBN4096BS. This CGRP antagonist was found to be a safe and effective acute treatment for migraine (Olesen et al., N. Engl. J. Med., 2004, 350(11), 1104-1110).

The present invention relates to compounds that are useful as ligands for CGRP receptors, in particular antagonists for CGRP receptors, processes for their preparation, their use in therapy, pharmaceutical compositions comprising them and methods of therapy using them.

SUMMARY OF THE INVENTION

The present invention is directed to compounds of Formula I:

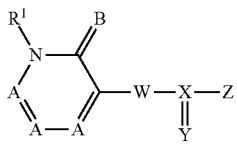

(where variables $R^1$, A, B, W, X, Y and Z are as defined herein) useful as antagonists of CGRP receptors and useful in the treatment or prevention of diseases in which the CGRP is involved, such as headache, migraine and cluster headache. The invention is also directed to pharmaceutical compositions comprising these compounds and the use of these compounds and compositions in the prevention or treatment of such diseases in which CGRP is involved.

DETAILED DESCRIPTION OF THE INVENTION

The present invention is directed to CGRP antagonists which include compounds of Formula I:

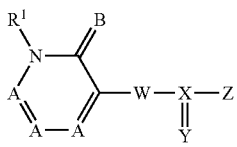

wherein:
Z is selected from:

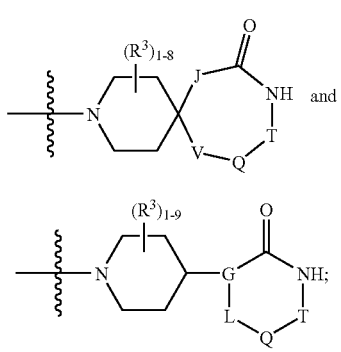

A is independently selected from N and $C(R^2)$;
B is O or S;
R is independently selected from:
1) H, $C_1$-$C_6$ alkyl, $C_2$-$C_6$ alkenyl, $C_2$-$C_6$ alkynyl, $C_{3-6}$ cycloalkyl, and heterocycle, unsubstituted or substituted with one or more substituents each independently selected from:
   a) $C_{1-6}$ alkyl,
   b) $C_{3-6}$ cycloalkyl,
   c) aryl, unsubstituted or substituted with 1-5 substituents each independently selected from $R^4$,
   d) heteroaryl, unsubstituted or substituted with 1-5 substituents each independently selected from $R^4$,
   e) heterocycle, unsubstituted or substituted with 1-5 substituents each independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$,
   p) $SO_2 NR^{10}R^{11}$,
   q) $N(R^{10}) SO_2 R^{11}$,
   r) $S(O)_m R^{10}$,
   s) CN,
   t) $NR^{10}R^{11}$,
   u) $N(R^{10})(CO)NR^4 R^{11}$, and,
   v) $O(CO)R^4$;
2) aryl or heteroaryl, unsubstituted or substituted with one or more substituents each independently selected from:
   a) $C_{1-6}$ alkyl,
   b) $C_{3-6}$ cycloalkyl,
   c) aryl, unsubstituted or substituted with 1-5 substituents each independently selected from $R^4$,
   d) heteroaryl, unsubstituted or substituted with 1-5 substituents each independently selected from $R^4$,
   e) heterocycle, unsubstituted or substituted with 1-5 substituents each independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) $(CO)NR^{10}R^{11}$,
   l) $O(CO)NR^{10}R^{11}$,
   m) $N(R^4)(CONR^{10}R^{11}$,
   n) $N(R^{10})(CO)R^{11}$,
   o) $N(R^{10})(CO)OR^{11}$,
   p) $SO_2 NR^{10}R^{11}$,
   q) $N(R^{10}) SO_2 R^{11}$,
   r) $S(O)_m R^{10}$,
   s) CN,
   t) $NR^{10}R^{11}$,
   u) $N(R^{10})(CO)NR^4 R^{11}$, and
   v) $O(CO)R^4$;
$R^2$ is independently selected from:
1) H, $C_1$-$C_6$ alkyl, $C_2$-$C_6$ alkenyl, $C_2$-$C_6$ alkynyl, $C_{3-6}$ cycloalkyl and heterocycle, unsubstituted or substituted with one or more substituents each independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents each independently selected from $R^4$,
   e) heterocycle, unsubstituted or substituted with 1-5 substituents each independently selected from $R^4$,
   f) $(F)_p C_{1-3}$ alkyl,
   g) halogen,
   h) $OR^4$,
   i) $O(CH_2)_s OR^4$,
   j) $CO_2 R^4$, k) $(CO)NR^{10}R^{11}$,
l) $O(CO)NR^{10}R^{11}$,
m) $N(R^4)(CO)NR^{10}R^{11}$,
n) $N(R^{10})(CO)R^{11}$,
o) $N(R^{10})(CO)OR^{11}$,
p) $SO_2NR^{10}R^{11}$
q) $N(R^{10}) SO_2R^{11}$,
r) $S(O)_mR^{10}$,
s) CN,
t) $NR^{10}R^{11}$,
u) $N(R^{10})(CO)NR^4R^{11}$, and,
v) $O(CO)R^4$;

2) aryl or heteroaryl, unsubstituted or substituted with one or more substituents each independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents each independently selected from $R^4$,
   e) heterocycle, unsubstituted or substituted with 1-5 substituents each independently selected from $R^4$,
   f) $(F)_pC_{1-3}$ alkyl,
   g) halogen,
   h) $OR^4$,
   i) $O(CH_2)_sOR^4$,
   j) $CO_2R^4$,
   k) $(CO)NR^{10}R^{11}$,
   l) $O(CO)NR^{10}R^{11}$,
   m) $N(R^{10})(CO)NR^{10}R^{11}$,
   n) $N(R^{10})(CO)R^{11}$,
   o) $N(R^{10})(CO)OR^{11}$,
   p) $SO_2NR^{10}R^{11}$,
   q) $N(R^{10})SO_2R^{11}$,
   r) $S(O)_mR^{10}$,
   s) CN,
   t) $NR^{10}R^{11}$,
   u) $N(R^{10})(CO)NR^4R^{11}$, and
   v) $O(CO)R^4$, where $R^1$ and $R^2$, or any two independent $R^2$, on adjacent atoms optionally join to form a ring selected from: $C_{5-7}$ cycloalkyl, heterocycle, aryl, and heteroaryl, in which the ring is unsubstituted or substituted with 1-10 substituents each independently selected from $R^6$;

$R^{10}$ and $R^{11}$ are independently selected from: H, $C_{1-6}$ alkyl, $(F)_pC_{1-6}$ alkyl, $C_{3-6}$ cycloalkyl, aryl, heteroaryl, and benzyl, unsubstituted or substituted with halogen, hydroxy or $C_1$-$C_6$ alkoxy, where $R^{10}$ and $R^{11}$ optionally join to form a ring selected from: azetidinyl, pyrrolidinyl, piperidinyl, piperazinyl, or morpholinyl, which is ring is unsubstituted or substituted with 1-5 substituents each independently selected from $R^4$;

$R^4$ is independently selected from: H, $C_{1-6}$ alkyl, $(F)_pC_{1-6}$ alkyl, $C_{3-6}$ cycloalkyl, aryl, heteroaryl and benzyl, unsubstituted or substituted with halogen, hydroxy or $C_1$-$C_6$ alkoxy;

W is O, $NR^4$ or $C(R^4)_2$;
X is C or S;
Y is O, $(R^4)_2$, NCN, $NSO_2CH_3$ or $NCONH_2$, or Y is $O_2$ when X is S;
$R^6$ is independently selected from H and:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents each independently selected from $R^4$,
   e) heterocycle, unsubstituted or substituted with 1-5 substituents each independently selected from $R^4$,
   f) $(F)_pC_{1-3}$ alkyl,
   g) halogen,
   h) $OR^4$,
   i) $O(CH_2)_sOR^4$,
   j) $CO_2R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$,
   p) $SO_2NR^{10}R^{11}$,
   q) $N(R^{10}) SO_2R^{11}$,
   r) $S(O)_mR^{10}$,
   s) CN,
   t) $NR^{10}R^{11}$,
   u) $N(R^{10})(CO)NR^4R^{11}$, and
   v) $O(CO)R^4$;

J is a bond, $C(R^6)_2$, O or $NR^6$;
V is selected from a bond, $C(R^6)_2$, O, $S(O)_m$, $NR^6$, $C(R^6)_2$—$C(R^6)_2$, $C(R^6)$=$C(R^6)$, $C(R^6)_2$—$N(R^6)$, $C(R^6)$=N, $N(R^6)$—$C(R^6)_2$, N=$C(R^6)$, and $N(R^6)$—$N(R^6)$;

G-L is selected from: N,N—$C(R^6)_2$, C=$C(R^6)$, C=N, $C(R^6)$, $C(R^6)$—$C(R^6)_2$, $C(R^6)$—$C(R^6)_2$—$C(R^6)_2$, C=C $(R^6)$—$C(R^6)_2$, $C(R^6)$—$C(R^6)$=$C(R^6)$, $C(R^6)$—$C(R^6)_2$—$N(R^6)$, C=$C(R^6)$—$N(R^6)$, $C(R^6)$—$C(R^6)$=N, $C(R^6)$—N $(R^6)$—$C(R^6)_2$, C=N—$C(R^6)_2$, $C(R^6)$—N=$C(R^6)$, $C(R^6)$—$N(R^6)$—$N(R^6)$, C—N—$N(R^6)$, N—$C(R^6)_2$—C $(R^6)_2$, N—$C(R^6)$=$C(R^6)$, N—$C(R^6)_2$—$N(R^6)$, N—C $(R^6)$=N,N—$N(R^6)$—$C(R^6)_2$ and N—N=$C(R^6)$;

Q is independently selected from:
(1) =$C(R^{7a})$—,
(2) —$C(R^{7a})_2$—,
(3) —C(=O)—,
(4) —$S(O)_m$—,
(5) =N—, and
(6) —$N(R^{7a})$—;

T is independently selected from:
(1) =$C(R^{7b})$—,
(2) —$C(R^{7b})_2$—,
(3) —C(=O)—,
(4) —$S(O)_m$—,
(5) =N—, and
(6) —$N(R^{7b})$—;

$R^3$ is independently selected from H, substituted or unsubstituted $C_1$-$C_3$ alkyl, F, CN and $CO_2R^4$;
$R^{7a}$ and $R^{7b}$ are each independently selected from $R^2$, where $R^{7a}$ and $R^{7b}$ and the atom or atoms to which they are attached optionally join to form a ring selected from $C_{3-6}$ cycloalkyl, aryl, heterocycle, and heteroaryl, which ring is unsubstituted or substituted with 1-10 substituents each independently selected from $R^6$;
p is 0 to 2q+1, for a substituent with q carbons;
m is 0, 1 or 2;
n is 0 or 1;
s is 1, 2 or 3;
and pharmaceutically acceptable salts and individual diastereomers thereof.

Further embodiments of the invention are CGRP antagonists of Formula I which include compounds of the Formula Ia:

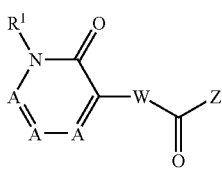

Ia wherein:
A is independently selected from N and C(R²);
R¹, W, and Z are as defined in Formula I;
and pharmaceutically acceptable salts and individual stereoisomers thereof.

Additional embodiments of the invention are CGRP antagonists of Formula I which include compounds of the Formula Ib:

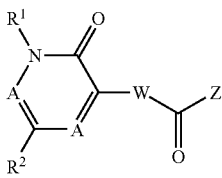

Ib wherein:
A is independently selected from N and C(R²);
R¹, R², W, and Z are as defined in Formula I;
and pharmaceutically acceptable salts and individual stereoisomers thereof.

Additional embodiments of the invention are CGRP antagonists of Formula I which include compounds of the Formula Ic:

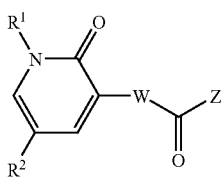

Ic wherein:
R¹, R², W, and Z are as defined in Formula I;
and pharmaceutically acceptable salts and individual stereoisomers thereof.

Additional embodiments of the invention are CGRP antagonists of Formula I which include compounds of the Formula Id:

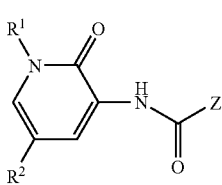

Id wherein:
R¹, R², and Z are as defined in Formula I;
and pharmaceutically acceptable salts and individual stereoisomers thereof.

Additional embodiments of the invention are CGRP antagonists of Formula I which include compounds of the Formula Ie:

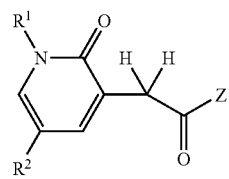

Ie wherein:
R¹, R², and Z are as defined in Formula I;
and pharmaceutically acceptable salts and individual stereoisomers thereof.

Further embodiments of the invention are CGRP antagonists of Formulae Ia-Ie,
wherein:
R¹ is selected from:
1) H, $C_1$-$C_6$ alkyl, $C_{3-6}$ cycloalkyl and heterocycle, unsubstituted or substituted with one or more substituents each independently selected from:
  a) $C_{1-6}$ alkyl,
  b) $C_{3-6}$ cycloalkyl,
  c) aryl, unsubstituted or substituted with 1-5 substituents where the substituents are independently selected from $R^4$,
  d) heteroaryl, unsubstituted or substituted with 1-5 substituents each independently selected from $R^4$,
  e) heterocycle, unsubstituted or substituted with 1-5 substituents each independently selected from $R^4$,
  f) $(F)_p C_{1-3}$ alkyl,
  g) halogen,
  h) $OR^4$,
  i) $O(CH_2)_s OR^4$,
  j) $CO_2 R^4$,
  k) CN,
  l) $NR^{10}R^{11}$, and
  m) $O(CO)R^4$; and
2) aryl or heteroaryl, unsubstituted or substituted with one or more substituents independently selected from:
  a) $C_{1-6}$ alkyl,
  b) $C_{3-6}$ cycloalkyl
  c) $(F)_p C_{1-3}$ alkyl,
  d) halogen,
  e) $OR^4$,
  f) $CO_2 R^4$.
  g) $(CO)NR^{10}R^{11}$
  h) $SO_2 NR^{10}R^{11}$,
  i) $N(R^{10})SO_2 R^{11}$.
  j) $S(O)_m R^4$,
  k) CN,
  l) $NR^{10}R^{11}$, and,
  m) $O(CO)R^4$;
R² is selected from:
1) H, $C_1$-$C_6$ alkyl, $C_2$-$C_6$ alkynyl, $C_{3-6}$ cycloalkyl and heterocycle, unsubstituted or substituted with one or more substituents each independently selected from:
  a) $C_{1-6}$ alkyl,
  b) $C_{3-6}$ cycloalkyl, c) aryl, unsubstituted or substituted with 1-5 substituents where the substituents are independently selected from $R^4$,
d) heteroaryl, unsubstituted or substituted with 1-5 substituents each independently selected from $R^4$,
e) heterocycle, unsubstituted or substituted with 1-5 substituents each independently selected from $R^4$,
f) $(F)_p C_{1-3}$ alkyl,
g) halogen,
h) $OR^4$,
i) $O(CH_2)_s OR^4$,
j) $CO_2 R^4$,
k) $S(O)_m R^4$,
l) CN,
m) $NR^{10} R^{11}$, and
n) $O(CO)R^4$; and
2) aryl or heteroaryl, unsubstituted or substituted with one more substituents independently selected from:
   a) $C_{1-6}$ alkyl,
   b) $C_{3-6}$ cycloalkyl,
   c) $(F)_p C_{1-3}$ alkyl,
   d) halogen,
   e) $OR^4$,
   f) $CO_2 R^4$,
   g) $(CO)NR^{10}R^{11}$,
   h) $SO_2 NR\ OR^{11}$,
   i) $N(R^{10})SO_2 R^{11}$,
   j) $S(O)_m R^4$,
   k) CN,
   l) $NR^{10}R^{11}$, and
   m) $O(CO)R^4$,
where $R^1$ and $R^2$, or any two independent $R^2$, on adjacent atoms optionally join to form a ring selected from: $C_{5-7}$ cycloalkyl, heterocycle, aryl, and heteroaryl, in which the ring is unsubstituted or substituted with 1-10 substituents each independently selected from $R^6$;
$R^{10}$ and $R^{11}$ are independently selected from: H, $C_{1-6}$ alkyl, $(F)_p C_{1-6}$ alkyl, $C_{3-6}$ cycloalkyl, aryl, heteroaryl and benzyl, unsubstituted or substituted with halogen, hydroxy or $C_1$-$C_6$ alkoxy, where $R^{10}$ and $R^{11}$ optionally join to form a ring selected from: azetidinyl, pyrrolidinyl, piperidinyl, piperazinyl and morpholinyl, which ring is unsubstituted or substituted with 1-5 substituents each independently selected from $R^4$;
$R^4$ is independently selected from: H, $C_{1-6}$ alkyl, $(F)_p C_{1-6}$ alkyl, $C_{3-6}$ cycloalkyl, aryl, heteroaryl and benzyl, unsubstituted or substituted with halogen, hydroxy or $C_1$-$C_6$ alkoxy;
W is O, $NR^4$ or $C(R^4)_2$;
$R^6$ is independently selected from H and:
   a) $C_{1-6}$ alkyl,
   b) $C_{3-6}$ cycloalkyl,
   c) $(F)_p C_{1-3}$ alkyl,
   d) halogen,
   e) $OR^4$,
   f) $CO_2 R^4$,
   g) $(CO)NR^{10}R^{11}$,
   h) $SO_2 NR^{10}R^{11}$,
   i) $N(R^{10})SO_2 R^{11}$,
   j) $S(O)_m R^4$,
   k) CN,
   l) $NR^{10}R^{11}$ and
   m) $O(CO)R^4$; and
J is a bond, $C(R^5)_2$, O, or $NR^5$, and V is a bond, $C(R^6)_2$, O, $S(O)_m$, $NR^6$, $C(R^6)_2$—$C(R^6)_2$, $C(R^6)$=$C(R^6)$, $C(R^6)_2$—$N(R^6)$, $C(R^6)$=$N$, $N(R^6)$—$C(R^6)_2$, $N$=$C(R^6)$ or $N(R^6)$—$N(R^6)$, such that when:

J is a bond, V is a bond and Z is Z1 the following structure forms:

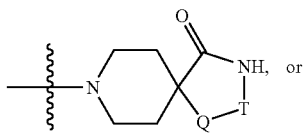

J is a bond, V is a bond, Z is Z1 and T is —C(=O)—, the following structure forms:

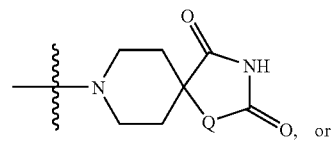

J is a bond and Z is Z1 the following structure forms:

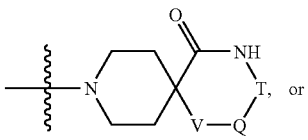

V is a bond and Z is Z1 the following structure forms:

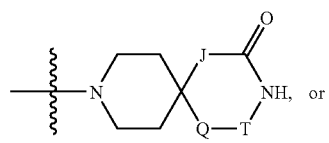

G-L is N, and Z is Z2 the following structure forms:

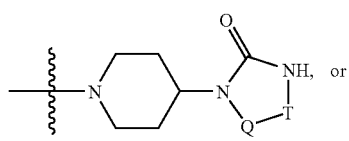

G-L is N—$C(R^6)_2$, and Z is Z2 the following structure forms:

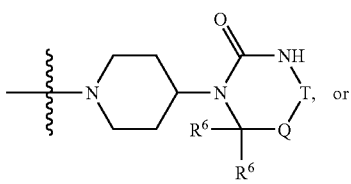

G-L is C=C(R⁶), and Z is Z2 the following structure forms:

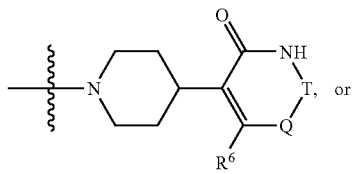

G-L is C=N, and Z is Z2 the following structure forms:

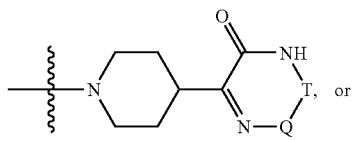

G-L is N—C(R⁶)₂—C(R⁶)₂, and Z is Z2 the following structure forms:

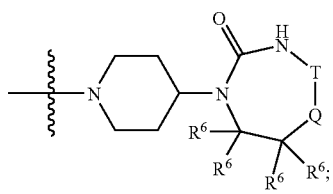

Q is independently selected from:
 (1) =C(R⁷ᵃ)—,
 (2) —C(R⁷ᵃ)₂,
 (3) —C(=O)—,
 (4) —S(O)ₘ—,
 (5) =N—, and
 (6) —N(R⁷ᵃ)—;
T is independently selected from:
 (1) =C(R⁷ᵇ),
 (2) —C(R⁷ᵇ)₂—,
 (3) —C(=O)—,
 (4) —S(O)ₘ—,
 (5) =N—, and
 (6) —N(R⁷ᵇ)—;
R³ is independently selected from H, substituted or unsubstituted $C_1$-$C_3$ alkyl, F, CN and $CO_2R^4$;
R⁷ᵃ and R⁷ᵇ are each independently selected from R², where R⁷ᵃ and R⁷ᵇ and the atom or atoms to which they are attached optionally join to form a ring selected from $C_{3-6}$cycloalkyl, aryl, heterocycle, and heteroaryl, which ring is unsubstituted or substituted with 1-10 substituents each each independently selected from R⁶;
p is 0 to 2q+1, for a substituent with q carbons
m is 0 to 2;
s is 1 to 3;
and pharmaceutically acceptable salts and individual stereoisomers thereof.

Still further embodiments of the invention are CGRP antagonists of Formulae Ia-Ib,
wherein:
R¹ is selected from:
 1) H, $C_1$-$C_6$ alkyl, $C_{3-6}$ cycloalkyl and heterocycle, unsubstituted or substituted with one or more substituents each independently selected from:
  a) $C_{1-6}$ alkyl,
  b) $C_{3-6}$ cycloalkyl,
  c) phenyl, unsubstituted or substituted with 1-5 substituents each independently selected from R⁴,
  d) heteroaryl, unsubstituted or substituted with 1-5 substituents each independently selected from R⁴, and where heteroaryl is selected from:
   imidazole, isoxazole, oxazole, pyrazine, pyrazole, pyridazine, pyridine, pyrimidine, and thiazole;
  e) heterocycle, unsubstituted or substituted with 1-5 substituents each independently selected from R⁴, and where heterocycle is selected from: azetidine, dioxane, dioxolane, morpholine, oxetane, piperazine, piperidine, pyrrolidine, tetrahydrofuran, and tetrahydropyran;
  f) (F)ₚ$C_{1-3}$ alkyl,
  g) halogen,
  h) OR⁴,
  i) O($C_{1-2}$)ₛOR⁴,
  j) $CO_2R^4$,
  k) CN,
  l) NR¹⁰R¹¹,
  m) O(CO)R⁴;
 2) aryl or heteroaryl, selected from: phenyl, imidazole, isoxazole, oxazole, pyrazine, pyrazole, pyridazine, pyridine, pyrimidine, and thiazole,
  unsubstituted or substituted with one or more substituents each independently selected from:
  a) $C_{1-6}$ alkyl,
  b) $C_{3-6}$ cycloalkyl,
  c) (F)ₚ$C_{1-3}$ alkyl,
  d) halogen,
  e) OR⁴,
  f) $CO_2R^4$,
  g) (CO)NR¹⁰R¹¹,
  h) $SO_2NR^{10}R^{11}$.
  i) N(R¹⁰)$SO_2R^{11}$,
  j) S(O)ₘR⁴,
  k) CN,
  l) NR¹⁰R¹¹, and
  m) O(CO)R⁴;
R² is selected from:
 1) H, $C_1$-$C_6$ alkyl, $C_{3-6}$ cycloalkyl and heterocycle, unsubstituted or substituted with one or more substituents each independently selected from:
  a) $C_{1-6}$ alkyl,
  b) $C_{3-6}$ cycloalkyl,
  c) phenyl, unsubstituted or substituted with 1-5 substituents each independently selected from R⁴,
  d) heteroaryl, unsubstituted or substituted with 1-5 substituents each independently selected from R⁴,
   and where heteroaryl is selected from: benzimidazole, benzothiophene, furan, imidazole, indole, isoxazole, oxazole, pyrazine, pyrazole, pyridazine, pyridine, pyrimidine, pyrrole, thiazole, thiophene, and triazole;
  e) heterocycle, unsubstituted or substituted with 1-5 substituents where the substituents are independently selected from R⁴, and where heterocycle is selected from: azetidine, imidazolidine, imidazoline, isoxazoline, isoxazolidine, morpholine, oxazoline, oxazolidine, oxetane, pyrazolidine, pyrazoline, pyrroline, tetrahydrofuran, tetrahydropyran, thiazoline, and thiazolidine;
  f) (F)ₚ$C_{1-3}$ alkyl,
  g) halogen,
  h) OR⁴, i) O(CH$_2$)$_s$OR$^4$,
j) CO$_2$R$^4$,
k) CN,
l) NR$^{10}$R$^{11}$, and
m) O(CO)R$^4$; and
2) aryl or heteroaryl, selected from:
   phenyl, benzimidazole, benzothiophene, furan, imidazole, indole, isoxazole, oxazole, pyrazine, pyrazole, pyridazine, pyridine, pyrimidine, pyrrole, thiazole, thiophene, and triazole, unsubstituted or substituted with one or more substituents each independently selected from:
   a) C$_{1-6}$ alkyl,
   b) C$_{3-6}$ cycloalkyl,
   c) (F)$_p$C$_{1-3}$ alkyl,
   d) halogen,
   e) OR$^4$,
   f) CO$_2$R$^4$,
   g) (CO)NR$^{10}$R$^{11}$,
   h) SO$_2$NR$^{10}$R$^{11}$,
   i) N(R$^{10}$) SO$_2$R$^{11}$,
   j) S(O)$_m$R$^4$,
   k) CN,
   l) NR$^{10}$R$^{11}$, and
   m) O(CO)R$^4$,
where R$^1$ and R$^2$, or any two independent R$^2$, on adjacent atoms optionally join to form a ring selected from: C$_{5-7}$ cycloalkyl, heterocycle, aryl, and heteroaryl, in which the ring is unsubstituted or substituted with 1-10 substituents each independently selected from R$^6$;
R$^{10}$ and R$^{11}$ are independently selected from: H, C$_{1-6}$ alkyl, (F)$_p$C$_{1-6}$ alkyl, C$_{3-6}$ cycloalkyl, aryl, heteroaryl and benzyl, unsubstituted or substituted with halogen, hydroxy or C$_1$-C$_6$ alkoxy, where R$^{10}$ and R$^{11}$ optionally join to form a ring selected from: azetidinyl, pyrrolidinyl, piperidinyl, piperazinyl and morpholinyl, which ring is unsubstituted or substituted with 1-5 substituents each independently selected from R$^4$;
R$^4$ is independently selected from: H, C$_{1-6}$ alkyl, (F)$_p$C$_{1-6}$ alkyl, C$_{3-6}$ cycloalkyl, aryl, heteroaryl and phenyl, unsubstituted or substituted with hydroxy or C$_1$-C$_6$ alkoxy;
W is NR$^4$ or C(R$^4$)$_2$;
R$^6$ is independently selected from H and:
   a) C$_{1-6}$ alkyl,
   b) C$_{3-6}$ cycloalkyl,
   c) (F)$_p$C$_{1-3}$ alkyl,
   d) halogen,
   e) OR$^4$,
   f) CO$_2$R$^4$,
   g) (CO)NR$^{10}$R$^{11}$,
   h) SO$_2$NR$^{10}$R$^{11}$,
   i) N(R$^{10}$)SO$_2$R$^{11}$,
   j) S(O)$_m$R$^4$,
   k) CN,
   l) NR$^{10}$R$^{11}$, and
   m) O(CO)R$^4$;

J is a bond, V is a bond, Z is Z1, Q is —N(R$^{7a}$)—, and T is —C(=O)—, such that the following structure forms:

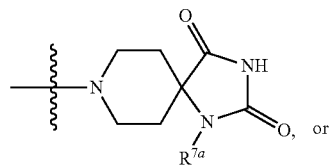

J is a bond, V is a bond, Z is Z1, Q is —C(R$^{7a}$)$_2$—, and T is —C(=O)—, such that the following structure forms:

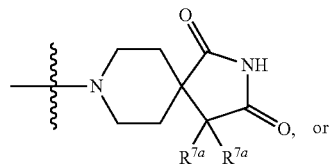

J is a bond, V is a bond, Z is Z1, Q is —N=, and T is =C(R$^{7b}$)—, such that the following structure forms:

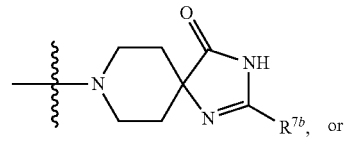

J is a bond, V is a bond, Z is Z1, Q is —C(R$^{7a}$)$_2$—, and T is —C(R$^{7b}$)$_2$—, such that the following structure forms:

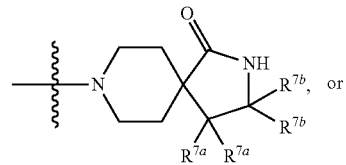

J is a bond, V is a bond, Z is Z1, Q is C(R$^{7a}$)=, T is —C(R$^{7b}$)—, and the atoms to which R$^{7a}$ and R$^{7b}$ are attached are joined together to form a benzene, pyridine, or diazine ring such that one of the following structures form:

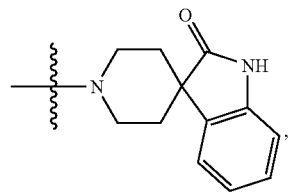

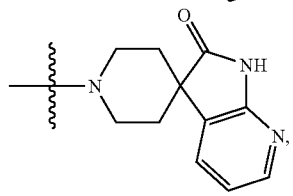

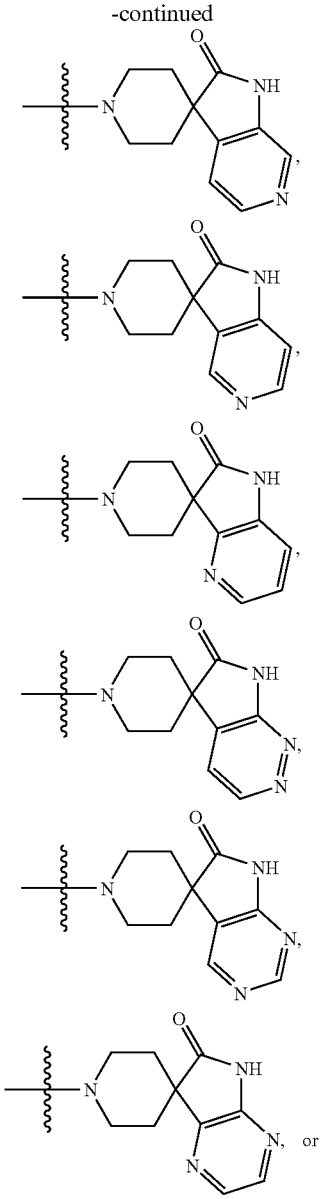

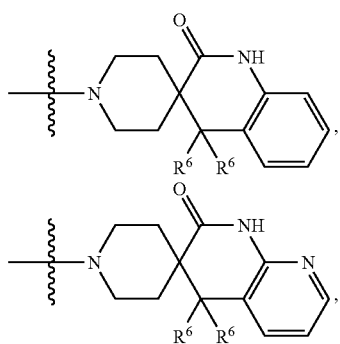

J is a bond, V is C(R$^{62}$, Z is Z1, Q is —C(R$^{7a}$)=, T is =C(R$^{7b}$)—, and the atoms to which R$^{7a}$ and R$^{7b}$ are attached are joined together to form a benzene, or pyridine ring such that one the following structures form:

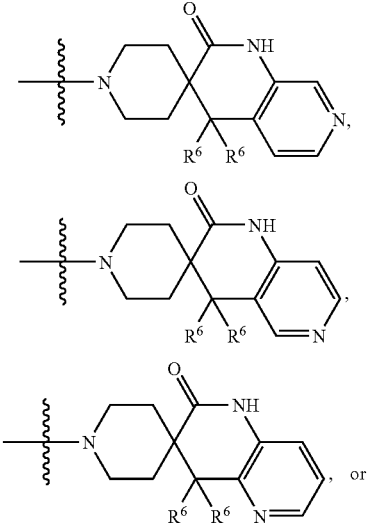

J is O, V is a bond, Z is Z1, Q is —C(R$^{7a}$)=, T is =C(R$^{7b}$)—, and the atoms to which R$^{7a}$ and R$^{7b}$ are attached are joined together to form a benzene, or pyridine ring such that one of the following structures form:

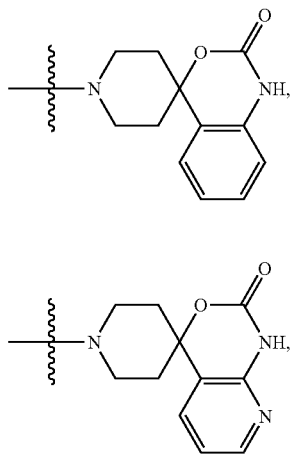

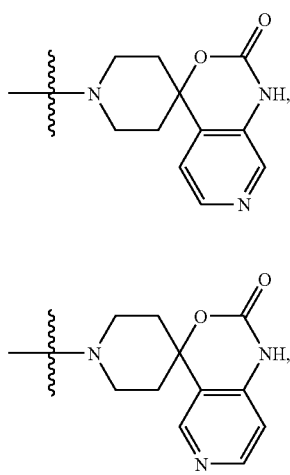

-continued

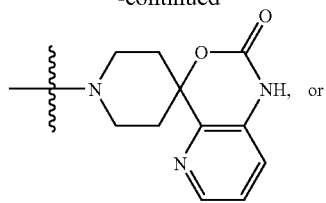

G-L is N, Z is Z2, Q is —C(R$^{7a}$)$_2$—, and T is —C(R$^{7b}$)$_2$—, such that the following structure forms:

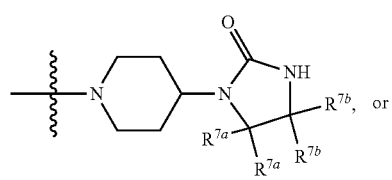

G-L is N, Z is Z2, Q is —C(R$^{7a}$)= and T is =C(R$^{7b}$)— such that the following structure forms:

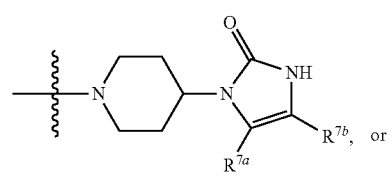

G-L is N, Z is Z2, Q is —N=, and T is =C(R$^{7b}$)—, such that the following structure forms:

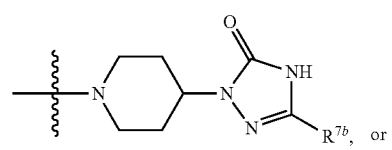

G-L is N, Z is Z2, Q is —C(R$^{7a}$)$_2$—, and T is —C(O)—, such that the following structure forms:

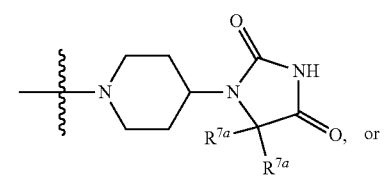

G-L is C=C(R$^6$), Z is Z2, Q is —C(R$^{7a}$)= and T is =C(R$^{7b}$)—, such that the following structure forms:

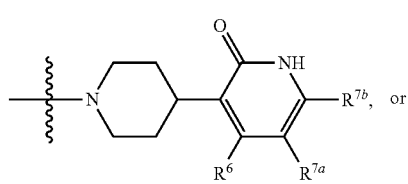

G-L is C=C(R$^6$), Z is Z2, Q is —C(R$^{7a}$)= and T is =N—, such that the following structure forms:

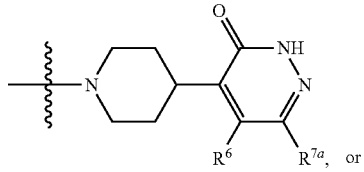

G-L is C=C(R$^6$), Z is Z2, Q is —N= and T is =C(R$^{7b}$)—, such that the following structure forms:

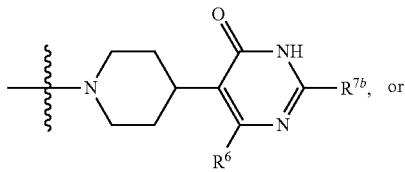

G-L is C—N, Z is Z2, Q is —C(R$^{7a}$)= and T is =C(R$^{7b}$)—, such that the following structure forms:

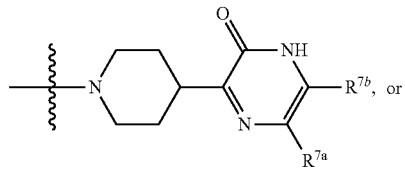

G-L is N, Z is Z2, Q is —C(R$^{7a}$)=, and T is =C(R$^{7b}$)—, and the atoms to which R$^{7a}$ and R$^{7b}$ are attached are joined together to form a benzene, pyridine, or diazine ring such that one of the following structures form:

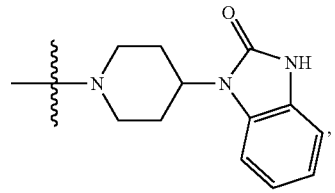

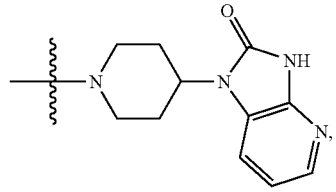

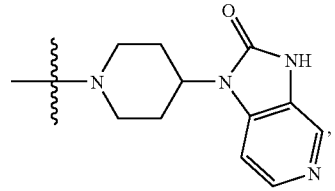

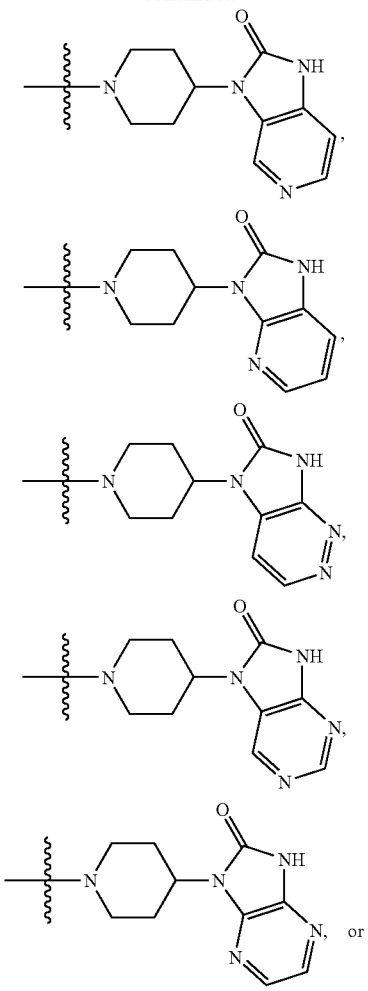

G-L is N—C(R⁶)₂, Z is Z2, Q is —C(R⁷ᵃ)=, and T is =C(R⁷ᵇ)—, and the atoms to which R⁷ᵃ and R⁷ᵇ are attached are joined together to form a benzene, or pyridine ring such that one of the following structures form:

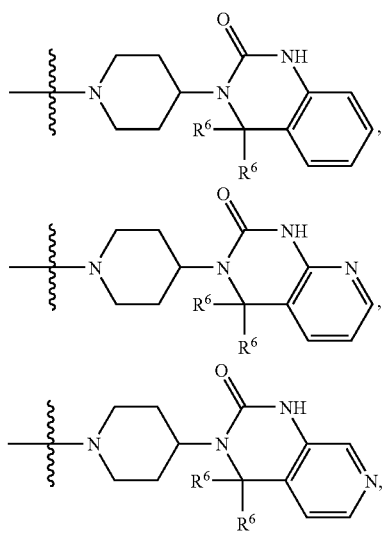

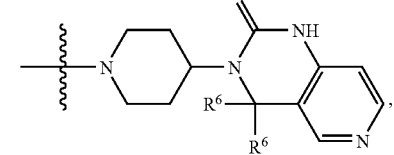

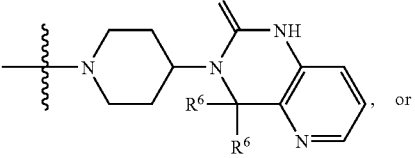

G-L is C=N, Z is Z2, Q is —C(R⁷ᵃ)=, and T is =C(R⁷ᵇ)—, and the atoms to which R⁷ᵃ and R⁷ᵇ are attached are joined together to form a benzene ring such that the following structure forms:

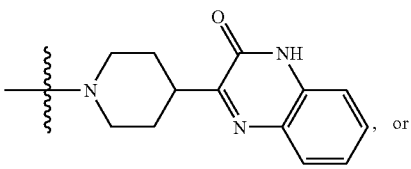

G-L is C=C(R⁶), Z is Z2, Q is —C(R⁷ᵃ)=, and T is =C(R⁷ᵇ)—, and the atoms to which R⁷ᵃ and R⁷ᵇ are attached are joined together to form a benzene ring such that the following structure forms:

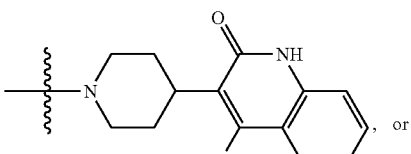

G-L is N—C(R⁶)₂—C(R⁶)₂, Z is Z2, Q is —C(R⁷ᵃ)=, and T is =C(R⁷ᵇ)—, and the atoms to which R⁷ᵃ and R⁷ᵇ are attached are joined together to form a benzene ring such that the following structure forms:

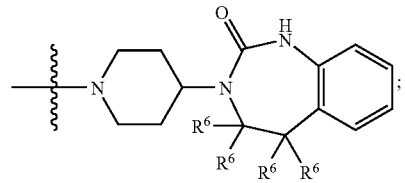

R³ is independently selected from H, substituted or unsubstituted C₁-C₃ alkyl, F, CN and CO₂R⁴;

R⁷ᵃ and R⁷ᵇ are each independently selected from R², where R⁷ᵃ and R⁷ᵇ and the atom or atoms to which they are attached optionally join to form a ring selected from C₃₋₆cycloalkyl, aryl, heterocycle, and heteroaryl which is unsubstituted or substituted with 1-10 substituents each each independently selected from R⁶;

p is 0 to 2q+1, for a substituent with q carbons m is 0 to 2;

s is 1 to 3;

and pharmaceutically acceptable salts and individual stereoisomers thereof.

It is to be understood that where one or more of the above recited structures or substructures recite multiple substituents having the same designation each such variable may be the same or different from each similarly designated variable. For example, $R^2$ is recited four times in formula I, and each $R^2$ in formula I may independently be any of the substructures defined under $R^2$. The invention is not limited to structures and substructures wherein each $R^2$ must be the same for a given structure. The same is true with respect to any variable appearing multiple time in a structure or substructure.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As will be appreciated by those of skill in the art, not all of the $R^{10}$ and $R^{11}$ substituents are capable of forming a ring structure. Moreover, even those substituents capable of ring formation may or may not form a ring structure.

Also as appreciated by those of skill in the art, halo or halogen as used herein are intended to include chloro, fluoro, bromo and iodo.

As used herein, "alkyl" is intended to mean linear, branched and cyclic structures having no double or triple bonds. Thus $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl and hexyl. "Cycloalkyl" is an alkyl, part or all of which which forms a ring of three or more atoms. $C_0$ or $C_0$alkyl is defined to identify the presence of a direct covalent bond.

The term "alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

The term "alkynyl" means linear or branched structures and combinations thereof, of the indicated number of carbon atoms, having at least one carbon-to-carbon triple bond. Thus $C_{2-6}$alkynyl is defined to identify the group as having 2, 3, 4, 5 or 6 carbons in a linear or branched arrangement, such that $C_{2-6}$alkynyl specifically includes 2-hexynyl and 2-pentynyl.

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term "heterocycle" or "heterocyclic", as used herein except where noted, represents a stable 5- to 7-membered monocyclic- or stable 8- to 11-membered bicyclic heterocyclic ring system which is either saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic groups include, but are not limited to, azetidine, chroman, dihydrofuran, dihydropyran, dioxane, dioxolane, hexahydroazepine, imidazolidine, imidazolidinone, imidazoline, imidazolinone, indoline, isochroman, isoindoline, isothiazoline, isothiazolidine, isoxazoline, isoxazolidine, morpholine, morpholinone, oxazoline, oxazolidine, oxazolidinone, oxetane, 2-oxohexahydroazepin, 2-oxopiperazine, 2-oxopiperidine, 2-oxopyrrolidine, piperazine, piperidine, pyran, pyrazolidine, pyrazoline, pyrrolidine, pyrroline, quinuclidine, tetrahydrofuran, tetrahydropyran, thiamorpholine, thiazoline, thiazolidine, thiomorpholine and N-oxides thereof.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

The term "alkoxy," as in $C_1$-$C_6$ alkoxy, is intended to refer to include alkoxy groups of from 1 to 6 carbon atoms of a straight, branched and cyclic configuration. Examples include methoxy, ethoxy, propoxy, isopropoxy, cyclopropyloxy, cyclohexyloxy and the like.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The number of certain variables present in certain instances is defined in terms of the number of carbons present. For example, variable "p" is occasionally defined as follows: "p is 0 to 2q+1, for a substituent with q carbons". Where the substituent is "$(F)_p C_{1-3}$ alkyl" this means that when there is one carbon, there are 2(1)+1=3 fluorines. When there are two carbons, there are 2(2)+1=5 fluorines, and when there are three carbons there are 2(3)=1=7 fluorines.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The subject compounds are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as antagonists of CGRP receptor activity may be demonstrated by methodology known in the art. Inhibition of the binding of $^{125}$I-CGRP to receptors and functional antagonism of CGRP receptors were determined as follows:

NATIVE RECEPTOR BINDING ASSAY: The binding of $^{125}$I-CGRP to receptors in SK-N-MC cell membranes was carried out essentially as described (Edvinsson et al. (2001) *Eur. J. Pharmacol.* 415, 39-44). Briefly, membranes (25 µg) were incubated in 1 ml of binding buffer [10 mM HEPES, pH 7.4, 5 mM $MgCl_2$ and 0.2% bovine serum albumin (BSA)] containing 10 µM $^{125}$I-CGRP andantagonist. After incubation at room temperature for 3 h, the assay was terminated by filtration through GFB glass fibre filter plates (Millipore) that had been blocked with 0.5% polyethyleneimine for 3 h. The filters were washed three times with ice-cold assay buffer, then the plates were air dried. Scintillation fluid (50 µl) was added and the radioactivity was counted on a Topcount (Packard Instrument). Data analysis was carried out by using Prism and the $K_i$ was determined by using the Cheng-Prusoff equation (Cheng & Prusoff (1973) *Biochem. Pharmacol.* 22, 3099-3108).

NATIVE RECEPTOR FUNCTIONAL ASSAY: SK-N-MC cells were grown in minimal essential medium (MEM) supplemented with 10% fetal bovine serum, 2 mM L-glutamine, 0.1 mM non-essential amino acids, 1 mM sodium pyruvate, 100 units/ml penicillin and 100 μg/ml streptomycin at 37° C., 95% humidity, and 5% $CO_2$. For cAMP assays, cells were plated at 5×10⁵ cells/well in 96-well poly-D-lysine-coated plates (Becton-Dickinson) and cultured for ~18 h before assay. Cells were washed with phosphate-buffered saline (PBS, Sigma) then pre-incubated with 300 μM isobutylmethylxanthine in serum-free MEM for 30 min at 37° C. Antagonist was added and the cells were incubated for 10 min before the addition of CGRP. The incubation was continued for another 15 min, then the cells were washed with PBS and processed for cAMP determination according to the manufacturer's recommended protocol. Maximal stimulation over basal was defined by using 100 nM CGRP. Dose-response curves were generated by using Prism. Dose-ratios (DR) were calculated and used to construct full Schild plots (Arunlakshana & Schild (1959) *Br. J. Pharmacol.* 14, 48-58).

RECOMBINANT RECEPTOR: Human CRLR (Genbank accession number L76380) was subcloned into the expression vector pIREShyg2 (BD Biosciences Clontech) as a 5'NheI and 3' PmeI fragment. Human RAMP1 (Genbank accession number AJ001014) was subcloned into the expression vector pIRESpuro2 (BD Biosciences Clontech) as a 5'NheI and 3'NotI fragment. 293 cells (human embryonic kidney cells; ATCC #CRL-1573) were cultured in DMEM with 4.5 g/L glucose, 1 mM sodium pyruvate and 2 mM glutamine supplemented with 10% fetal bovine serum (FBS), 100 units/mL penicillin and 100 ug/ml streptomycin, and maintained at 37° C. and 95% humidity. Cells were subcultured by treatment with 0.25% trypsin with 0.1% EDTA in HBSS. Stable cell line generation was accomplished by co-transfecting 10 ug of DNA with 30 ug Lipofectamine 2000 (Invitrogen) in 75 cm² flasks. CRLR and RAMP1 expression constructs were co-transfected in equal amounts. Twenty-four hours after transfection the cells were diluted and selective medium (growth medium+300 ug/ml hygromycin and 1 ug/ml puromycin) was added the following day. A clonal cell line was generated by single cell deposition utilizing a FACS Vantage SE (Becton Dickinson). Growth medium was adjusted to 150 ug/ml hygromycin and 0.5 ug/ml puromycin for cell propagation.

RECOMBINANT RECEPTOR BINDING ASSAY: Cells expressing recombinant human CRLR/RAMP1 were washed with PBS and harvested in harvest buffer containing 50 mM HEPES, 1 mM EDTA and Complete protease inhibitors (Roche). The cell suspension was disrupted with a laboratory homogenizer and centrifuged at 48,000 g to isolate membranes. The pellets were resuspended in harvest buffer plus 250 mM sucrose and stored at −70° C. For binding assays, 10 ug of membranes were incubated in 1 ml binding buffer (10 mM HEPES, pH 7.4, 5 mM $MgCl_2$, and 0.2% BSA) for 3 hours at room temperature containing 10 pM $^{125}$I-hCGRP (Amersham Biosciences) and antagonist. The assay was terminated by filtration through 96-well GFB glass fiber filter plates (Millipore) that had been blocked with 0.05% polyethyleneimine. The filters were washed 3 times with ice-cold assay buffer (10 mM HEPES, pH 7.4). Scintillation fluid was added and the plates were counted on a Topcount (Packard). Non-specific binding was determined and the data analysis was carried out with the apparent dissociation constant ($K_i$) determined by using a non-linear least squares fitting the bound CPM data to the equation below:

$$Y_{obsd} = \frac{(Y_{max} - Y_{min})(\%I_{max} - \%I_{min}/100) +}{1 + ([\text{Drug}]/K_i(1+[\text{Radiolabel}]/K_d)^{nH}}$$

Where Y is observed CPM bound, $Y_{max}$ is total bound counts, Y min is non specific bound counts, (Y max−Y min) is specific bound counts, % I max is the maximum percent inhibition, % I min is the minimum percent inhibition, radiolabel is the probe, and the $K_d$ is the apparent dissociation constant for the radioligand for the receptor as determined by Hot saturation experiments.

RECOMBINANT RECEPTOR FUNCTIONAL ASSAY: Cells were plated in complete growth medium at 85,000 cells/well in 96-well poly-D-lysine coated plates (Corning) and cultured for ~19 h before assay. Cells were washed with PBS and then incubated with inhibitor for 30 min at 37° C. and 95% humidity in Cellgro Complete Serum-Free/Low-Protein medium (Mediatech, Inc.) with L-glutamine and 1 g/L BSA. Isobutyl-methylxanthine was added to the cells at a concentration of 300 μM and incubated for 30 min at 37° C. Human α-CGRP was added to the cells at a concentration of 0.3 nM and allowed to incubate at 37° C. for 5 min. After α-CGRP stimulation the cells were washed with PBS and processed for cAMP determination utilizing the two-stage assay procedure according to the manufacturer's recommended protocol (cAMP SPA direct screening assay system; RPA 559; Amersham Biosciences). Dose response curves were plotted and $IC_{50}$ values determined from a 4-parameter logistic fit as defined by the equation $y=((a-d)/(1+(x/c)^b)+d$, where y=response, x=dose, a=max response, d=min response, c=inflection point and b=slope.

In particular, the compounds of the following examples had activity as antagonists of the CGRP receptor in the aforementioned assays, generally with a $K_1$ or $IC_{50}$ value of less than about 50 μM. Such a result is indicative of the intrinsic activity of the compounds in use as antagonists of CGRP receptors.

The ability of the compounds of the present invention to act as CGRP antagonists makes them useful pharmacological agents for disorders that involve CGRP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; psoriasis; encephalitis; brain trauma; epilepsy; neurodegenerative diseases; skin diseases; neurogenic cutaneous redness, skin rosaceousness and erythema; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with an an anti-migraine agent, such as ergotamine and dihydroergotamine, or other serotonin agonists, especially a 5-$HT_{1B/1D}$ agonist, for example sumatriptan, naratriptan, zolmitriptan, eletriptan, almotriptan, frovatriptan, donitriptan, and rizatriptan, a 5-$HT_{1D}$ agonist such as PNU-142633 and a 5-$HT_{1F}$ agonist such as LY334370; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as ibuprofen, ketoprofen, fenoprofen, naproxen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or glucocorticoids. Similarly, the instant compounds may be administered with an analgesic such as aspirin, acetaminophen, phenacetin, fentanyl, sufentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist; an NR2B antagonist; a bradykinin-1 receptor antagonist; an adenosine A1 receptor agonist; a sodium channel blocker, for example lamotrigine; an opiate agonist such as levomethadyl acetate or methadyl acetate, a lipoxygenase inhibitor, such as an inhibitor of 5-lipoxygenase; an alpha receptor antagonist, for example indoramin; an alpha receptor agonist; a vanilloid receptor antagonist; a renin inhibitor; a granzyme B inhibitor; a substance P antagonist; an endothelin antagonist; a norepinephrin precursor; anti-anxiety agents such as diazepam, alprazolam, chlordiazepoxide and chlorazepate; serotonin $5HT_2$ receptor antagonists; opiod agonists such as codeine, hydrocodone, tramadol, dextropropoxyphene and febtanyl; an mGluR5 agonist, antagonist or potentiator; a GABA A receptor modulator, for example acamprosate calcium; nicotinic antagonists or agonists including Inicotine; muscarinic agonists or antagonists; a selective serotonin reuptake inhibitor, for example fluoxetime, paroxetine, sertraline, duloxetine, escitalopram, or citalopram; anantidepressant, for example amitriptyline, nortriptyline, clomipramine, imipramine, venlafaxine, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with gap junction inhibitors; neuronal calcium channel blockers such as civamide; AMPA/KA antagonists such as LY293558; sigma receptor agonists; and vitamin B2.

Also, the present compounds may be used in conjunction with ergot alkaloids other than ergotamine and dihydroergotamine, for example ergonovine, ergonovine, methylergonovine, metergoline, ergoloid mesylates, dihydroergocornine, dihydroergocristine, dihydroergocryptine, dihydro-α-ergocryptine, dihydro-β-ergocryptine, ergotoxine, ergocornine, ergocristine, ergocryptine, α-ergocryptine, β-ergocryptine, ergosine, ergostane, bromocriptine, or methysergide.

Additionally, the present compounds may be used in conjunction with a beta-adrenergic antagonist such as timolol, propanolol, atenolol, metoprolol or nadolol, and the like; a MAO inhibitor, for example phenelzine; a calcium channel blocker, for example flunarizine, diltiazem, amlodipine, felodipine, nisolipine, isradipine, nimodipine, lomerizine, verapamil, nifedipine, or prochlorperazine; neuroleptics such as olanzapine, droperidol, prochlorperazine, chlorpromazine and quetiapine; an anticonvulsant such as topiramate, zonisamide, tonabersat, carabersat, levetiracetam, lamotrigine, tiagabine, gabapentin, pregabalin or divalproex sodium; an anti-hypertensive such as an angiotensin II antagonist, for example losartan, irbesartin, valsartan, eprosartan, telmisartan, olmesartan, medoxomil, candesartan and candesartan cilexetil, an angiotensin I antagonist, an angiotensin converting enzyme inhibitor such as lisinopril, enalapril, captopril, benazepril, quinapril, perindopril, ramipril and trandolapril; or botulinum toxin type A or B.

The present compounds may be used in conjunction with a potentiator such as caffeine, an H2-antagonist, simethicone, aluminum or magnesium hydroxide; a decongestant such as oxymetazoline, epinephrine, naphazoline, xylometazoline, propylhexedrine, or levo-desoxy-ephedrine; an antitussive such as caramiphen, carbetapentane, or dextromethorphan; a diuretic; a prokinetic agent such as metoclopramide or domperidone; a sedating or non-sedating antihistamine such as acrivastine, azatadine, bromodiphenhydramine, brompheniramine, carbinoxamine, chlorpheniramine, clemastine, dexbrompheniramine, dexchlorpheniramine, diphenhydramine, doxylamine, loratadine, phenindamine, pheniramine, phenyltoloxamine, promethazine, pyrilamine, terfenadine, triprolidine, phenylephrine, phenylpropanolamine, or pseudoephedrine. The present compounds also may be used in conjunction with anti-emetics.

In a particularly preferred embodiment the present compounds are used in conjunction with an anti-migraine agent, such as: ergotamine or dihydroergotamine; a 5-HT, agonist, especially a 5-$HT_{1B/1D}$ agonist in particular, sumatriptan, naratriptan, zolmitriptan, eletriptan, almotriptan, frovatriptan, donitriptan, avitriptan and rizatriptan, and other serotonin agonists; and a cyclooxygenase inhibitor, such as a selective cyclooxygenase-2 inhibitor, in particular, rofecoxib, etoricoxib, celecoxib, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetaniol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require antagonism of CGRP receptor activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of headache, migraine, cluster headache, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes. The synthesis of intermediates and final compounds may be conducted as described in Schemes 1-12.

REACTION SCHEMES

Diamino heterocycles, such as 2,3-diaminopyridine 1, can be reductively alkylated with ketones such as 2 to give the monalkylated product 3 (Scheme 1). Ring closure with carbonyldiimidazole furnishes imidazolone 4. Final deprotection under standard conditions gives the intermediate 5.

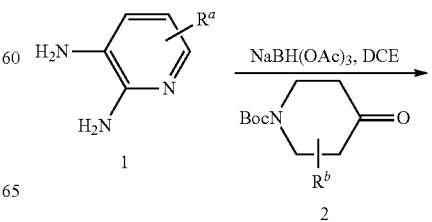

SCHEME 1

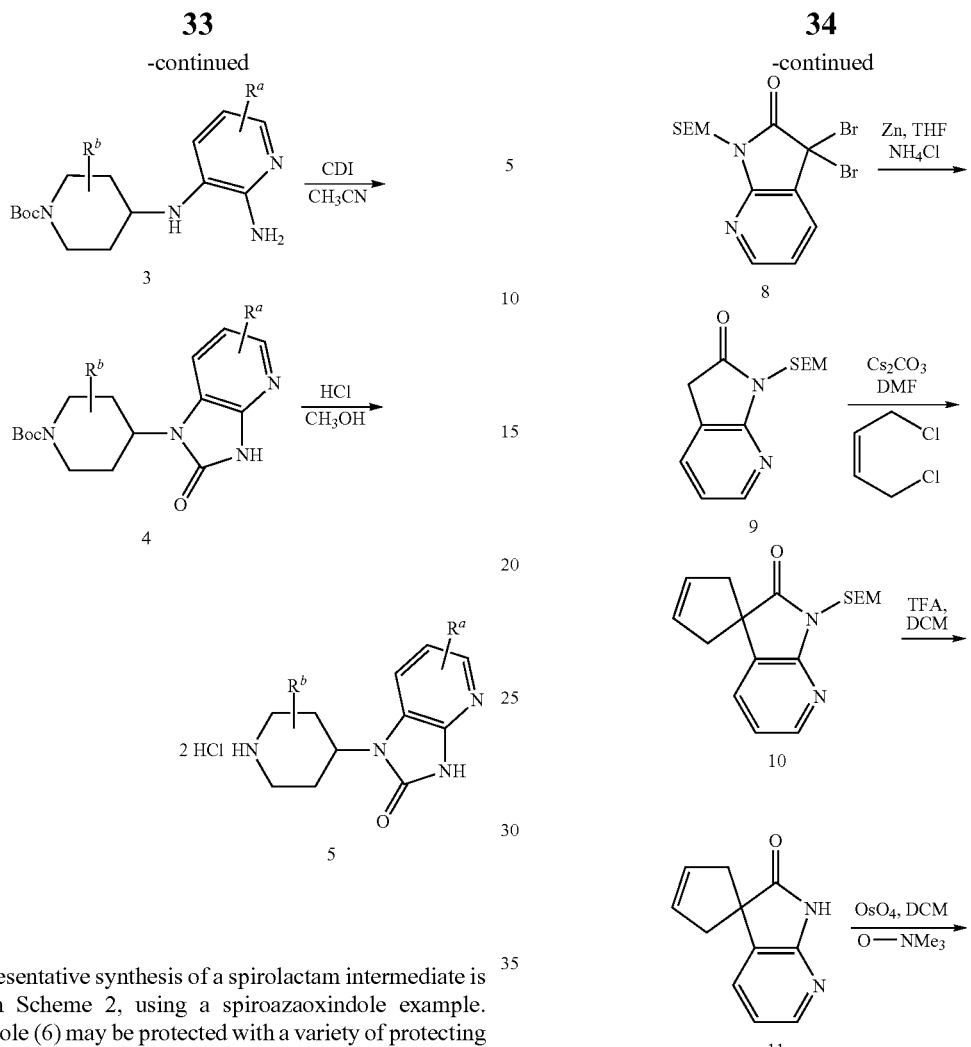

A representative synthesis of a spirolactam intermediate is shown in Scheme 2, using a spiroazaoxindole example. 7-Azaindole (6) may be protected with a variety of protecting groups, such as the (trimethylsilyl)ethoxymethyl group shown in Scheme 2. Following the method of Marfat and Carter (*Tetrahedron Lett.*, 1987, 28, 40274030), treatment of 7 with pyridine hydrobromide perbromide provides the dibromoazaoxindole 8, which may be reduced to the corresponding azaoxindole 9 by reaction with zinc. Alkylation of 9 with cis-1,4-dichloro-2-butene is carried out using cesium carbonate in DMF to afford the spiroazaoxindole 10. Removal of the SEM protecting group under standard conditions followed by osmium tetroxide catalyzed dihydroxylation provides the diol intermediate 12. Periodate oxidative cleavage of the diol, followed by a double reductive amination (*Org. Lett.*, 2000, 26, 4205-4208) affords the spiropiperidine 13. The methodology shown in Scheme 2 is not limited to azaoxindoles such as 9, but may be applied to a variety of suitably protected heterocyclic systems to give the corresponding spiro compounds.

SCHEME 2

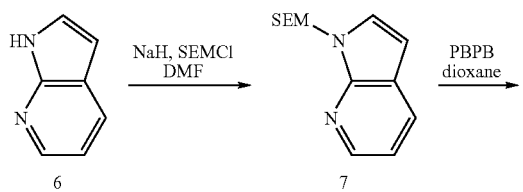

Triazolinones can be prepared according to Scheme 3. For example, a 4-piperidinone 14 can be reductively aminated with a carbazate which, after reduction of hydrazone X, gives the monoalkylated product 16. Deprotection to afford hydrazine 17 and condensation/ring closure with a benzothioyl carbamate such as 18 furnishes triazolinone 19. Filial deprotection under standard conditions gives the product 20.

SCHEME 3

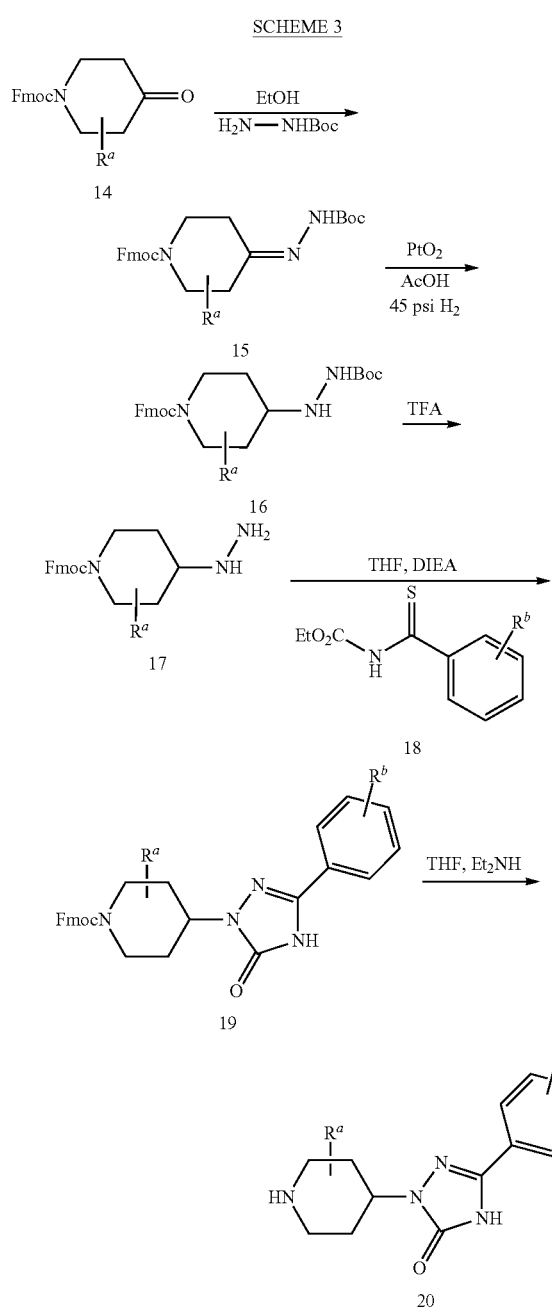

The intermediate 26 can be prepared according to the general method described by Takai et al., *Chem. Pharm. Bull.* 1985, 33, 1116-1128 illustrated in Scheme 4.

SCHEME 4

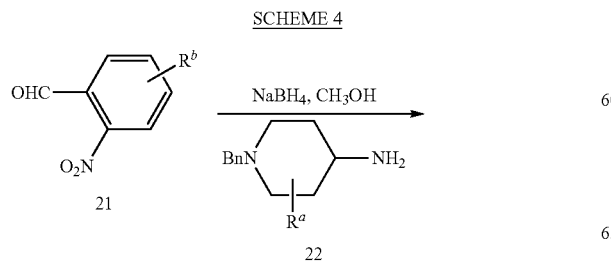

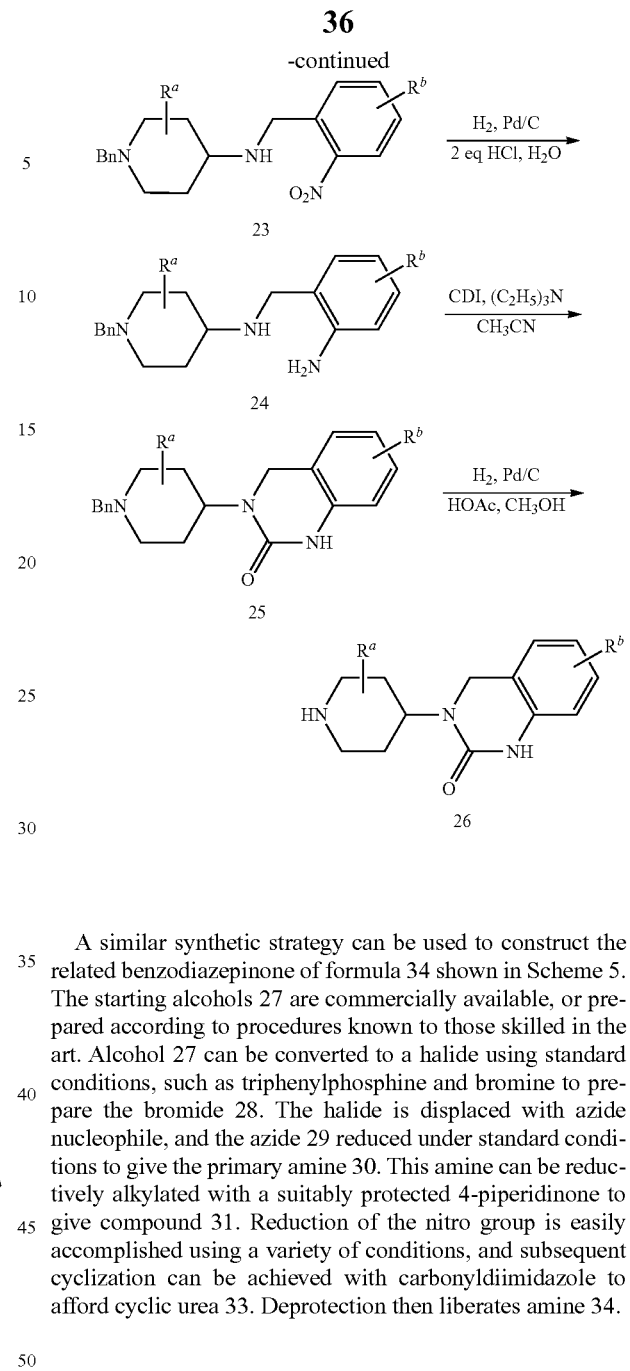

A similar synthetic strategy can be used to construct the related benzodiazepinone of formula 34 shown in Scheme 5. The starting alcohols 27 are commercially available, or prepared according to procedures known to those skilled in the art. Alcohol 27 can be converted to a halide using standard conditions, such as triphenylphosphine and bromine to prepare the bromide 28. The halide is displaced with azide nucleophile, and the azide 29 reduced under standard conditions to give the primary amine 30. This amine can be reductively alkylated with a suitably protected 4-piperidinone to give compound 31. Reduction of the nitro group is easily accomplished using a variety of conditions, and subsequent cyclization can be achieved with carbonyldiimidazole to afford cyclic urea 33. Deprotection then liberates amine 34.

SCHEME 5

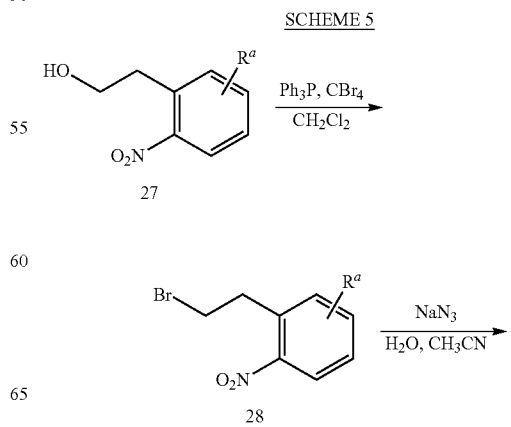

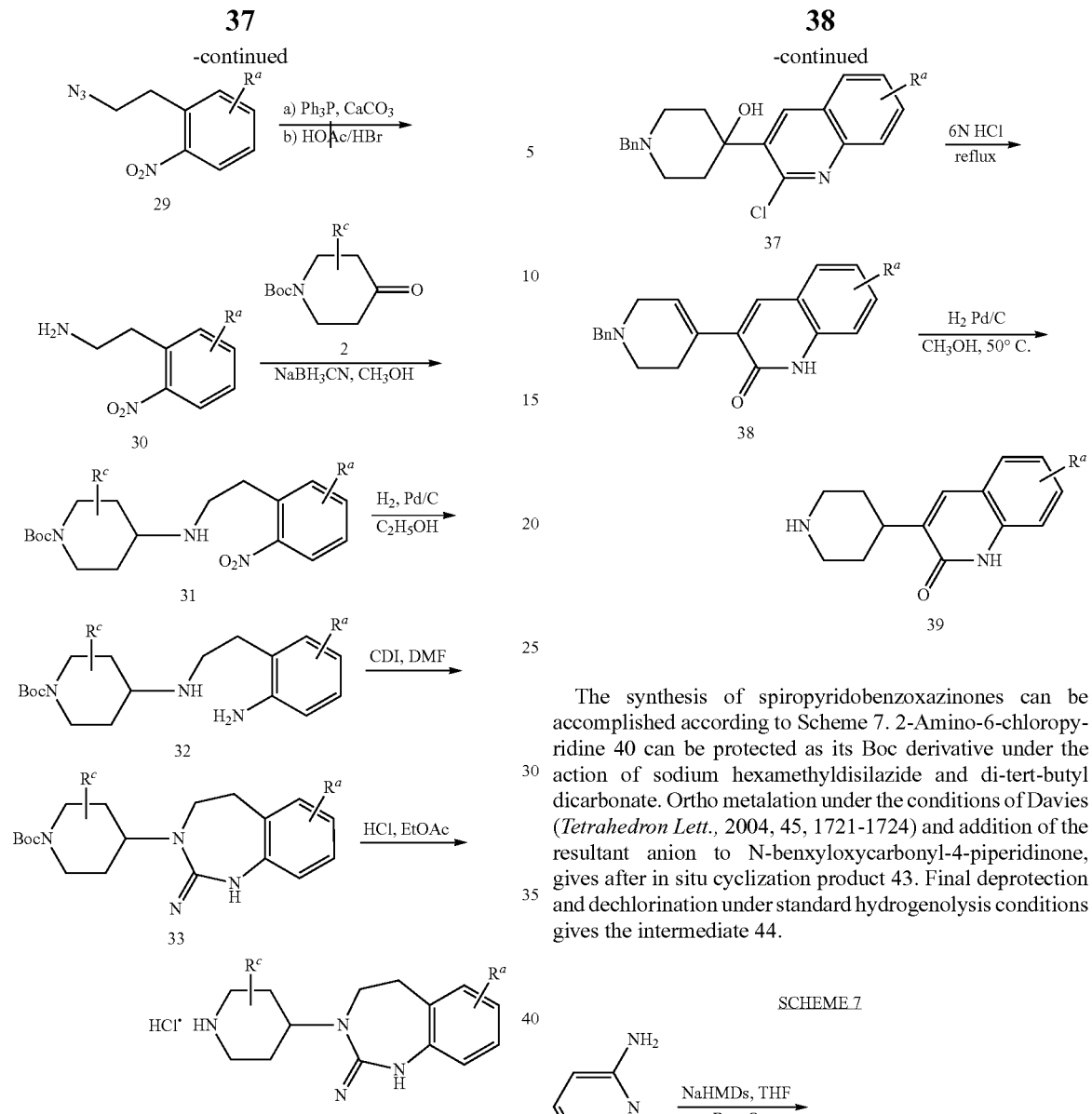

Quinolone 39 can be prepared by reaction of the anion derived from 2-chloroquinoline and lithium diisopropylamide, with piperidone 36 (Scheme 6). Concommitant elimination of the tertiary alcohol and hydrolysis of the chloroquinoline is accomplished with aqueous hydrochloric acid. Removal of the piperidine N-benzyl protective group by catalytic hydrogenation also reduces the olefin formed in the previous step and results in amine 39.

The synthesis of spiropyridobenzoxazinones can be accomplished according to Scheme 7. 2-Amino-6-chloropyridine 40 can be protected as its Boc derivative under the action of sodium hexamethyldisilazide and di-tert-butyl dicarbonate. Ortho metalation under the conditions of Davies (*Tetrahedron Lett.*, 2004, 45, 1721-1724) and addition of the resultant anion to N-benxyloxycarbonyl-4-piperidinone, gives after in situ cyclization product 43. Final deprotection and dechlorination under standard hydrogenolysis conditions gives the intermediate 44.

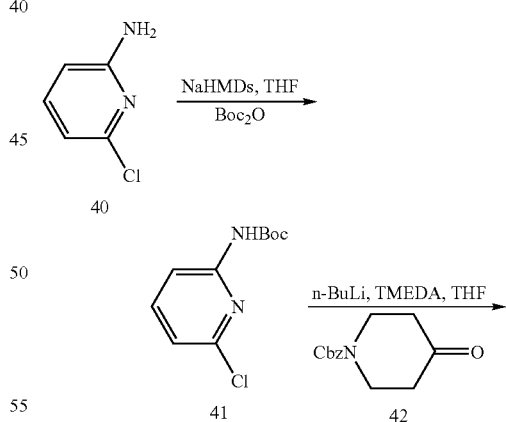

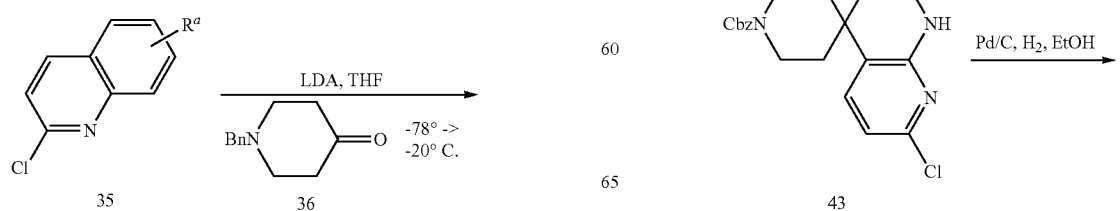

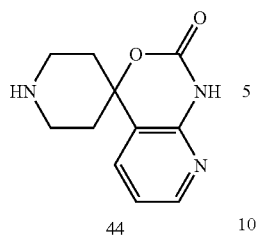

44

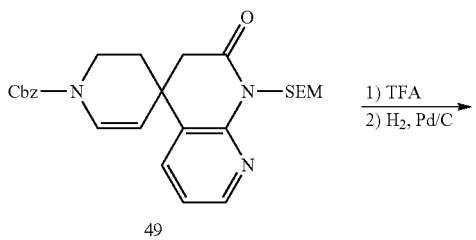

49

In Scheme 8, Wittig reaction of the 4-ketopiperidine 42 gives the α,β-unsaturated ester 45. The resulting product can be isomerized to the β,γ-unsaturated ester 46 under basic conditions (*Tetrahedron Lett,* 2004, 44014404). Trimethylaluminum mediated amidation with 2-amino-3-bromopyridine followed by amide alkylation with 2-trimethylsilyl) ethoxymethyl chloride affords the product 48. The key palladium-mediated spirocyclization can be affected through the Fu modification (*J. Amer. Chem. Soc.,* 2001, 6989-7000) of the Heck reaction. A two-stage deprotection with concomitant double bond reduction under standard conditions gives the desired spironaphthyridinone 50.

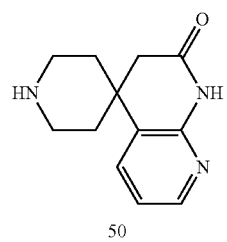

50

Amino-pyridinones are prepared as outlined in Scheme 9. Commercially available hydroxypyridine 51 can be selectively N-alkylated using various electrophiles with cesium carbonate. Reduction of the nitro group with tin(II) chloride gives the primary amine 53. Urea formation is accomplished by activation of the amine, in this case with p-nitrophenyl chloroformate, and coupling with the desired substituted piperidines affording 54. Palladium-mediated cross coupling with different aryl, heteroaryl, and alkyl groups affords the substituted pyridinones 55.

SCHEME 8

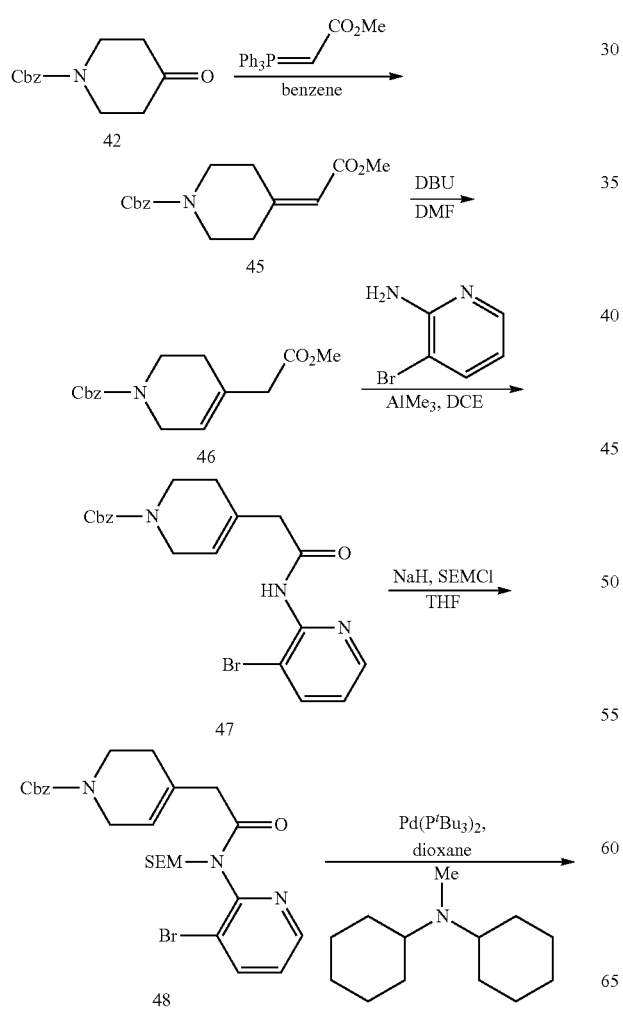

SCHEME 9

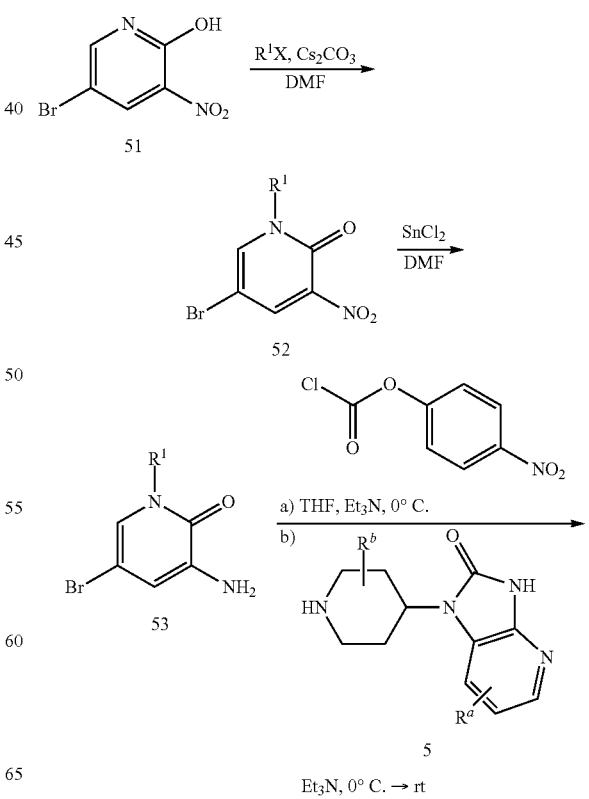

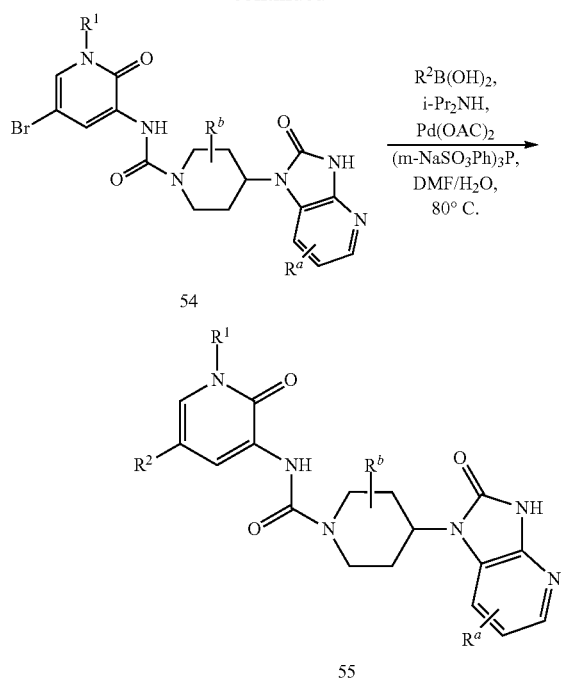

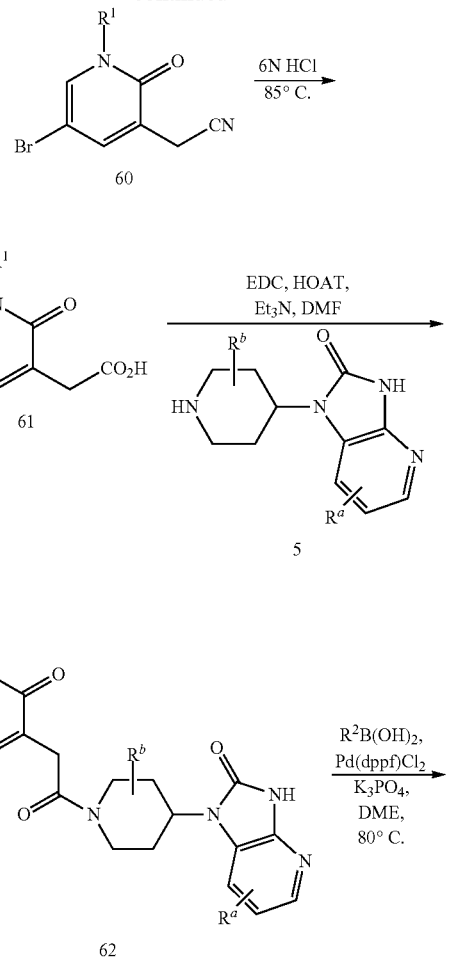

Acetyl-linked pyridinones are prepared as shown in Scheme 10. Commercially available 3-methyl-2-pyridinone can be selectively N-alkylated using various electrophiles with cesium carbonate. Treatment with NBS in the absence of light yields the mono-bromo pyridinone 58. Further treatment with NBS in the presence of AIBN affords the bis-bromominated product 59. After reaction with sodium cyanide then acidic hydrolysis, acid 61 is coupled with various substituted piperidines under standard conditions to give amide 62. Palladium-mediated cross coupling with different aryl, heteroaryl, and alkyl groups affords the substituted pyridinones 63.

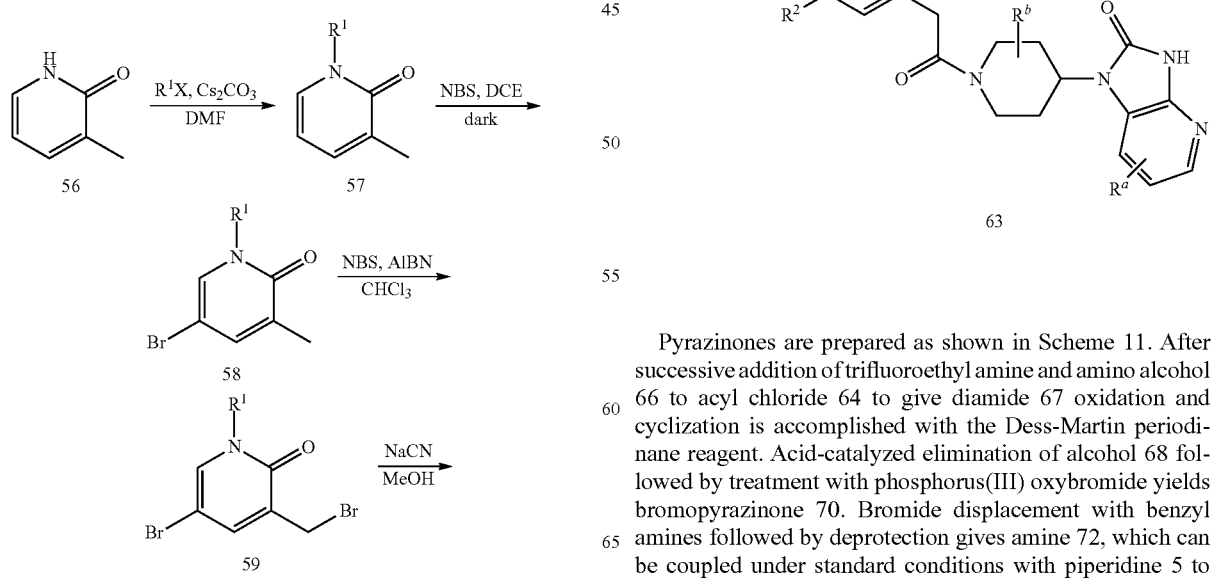

Pyrazinones are prepared as shown in Scheme 11. After successive addition of trifluoroethyl amine and amino alcohol 66 to acyl chloride 64 to give diamide 67 oxidation and cyclization is accomplished with the Dess-Martin periodinane reagent. Acid-catalyzed elimination of alcohol 68 followed by treatment with phosphorus(III) oxybromide yields bromopyrazinone 70. Bromide displacement with benzyl amines followed by deprotection gives amine 72, which can be coupled under standard conditions with piperidine 5 to afford pyrazinone 73.

SCHEME 11

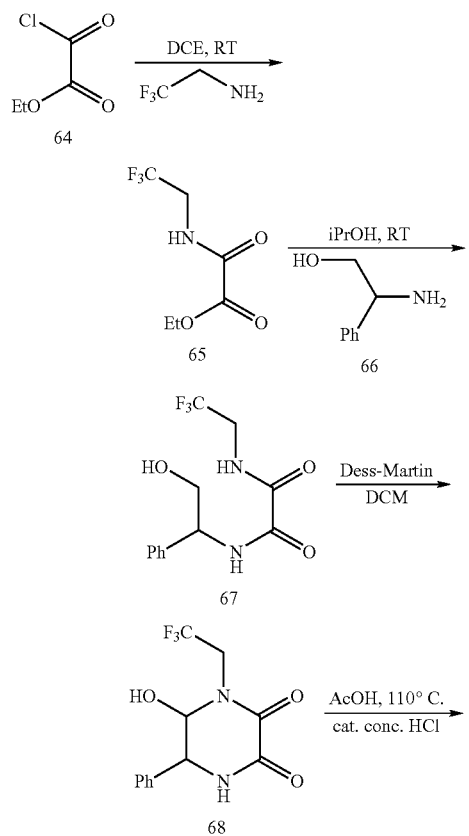

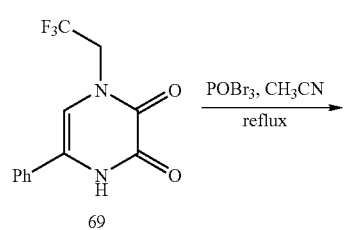

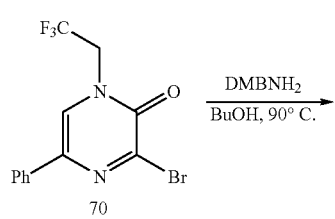

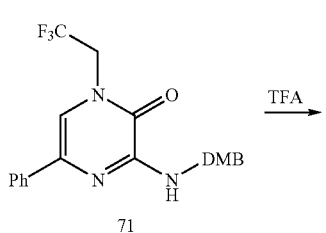

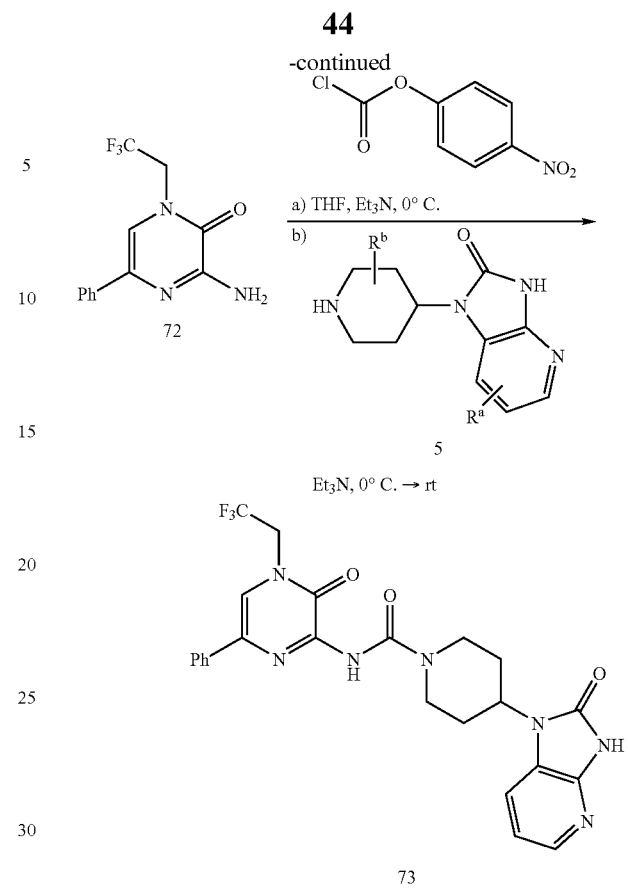

INTERMEDIATES AND EXAMPLES

The following examples are provided so that the invention might be more fully understood. These examples are illustrative only and should not be construed as limiting the invention in any way.

INTERMEDIATE 1

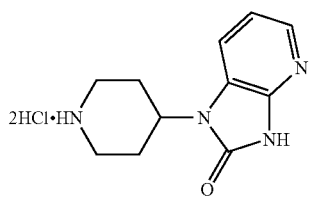

2-Oxo-1-(4-piperidinyl)-2,3-dihydro-1H-imidazo[4,5-b]pyridine dihydrochloride

Step A. 2-Amino-3-[(1-tert-butoxycarbonylpiperidin-4-yl)amino)pyridine

Sodium triacetoxyborohydride (14.5 g, 68.7 mmol) was added to a solution of 2,3-diaminopyridine (5.00 g, 45.8 mmol) and N-(tert-butoxycarbonyl)-4-piperidone (9.58 g, 48.1 mmol) in dichloroethane (75 mL) at room temperature. After 5 h, additional sodium triacetoxyborohydride was added (1.8 g) and again after another 2.5 h. The reaction was stirred overnight, and quenched with 5% aqueous sodium hydroxide. This was extracted with methylene chloride, and washed with 5% aqueous sodium hydroxide, water and saturated sodium chloride solution. After drying over sodium sulfate, the solution was filtered and evaporated to give the crude product. This was purified by chromatography (silica gel, 3 to 5% methanol in methylene chloride gradient elution), which gave the title compound (4.44 g). MS 293 (M+1) ¹H NMR (500 MHz, CD₃OD) δ 7.32 (dd, J=5, 1 Hz, 1H), 6.85 (dd, J=8, 1 Hz, 1H), 6.59 (dd, J=8, 5 Hz, 1H), 4.04 (d, J=13 Hz, 2H), 3.46 (m, 1H), 2.98 (br s, 2H), 2.01 (dd, J=12, 2 Hz, 2H), 1.46 (s, 9H), 1.37 (qd, J=12, 4 Hz, 2H).

Step B. 2-Oxo-1-(1-tert-butoxycarbonylpiperidin-4-yl)-2,3-dihydro-1H-imidazo[4,5-b]pyridine Carbonyldiimidazole (0.70 g, 4.33 mmol) was added to a solution of 2-amino-3-[(1-tert-butoxycarbonylpiperidin-4-yl)amino]pyridine (1.15 g, 3.93 mmol) in acetonitrile (150 mL) at room temperature. After several hours, an additional amount of carbonyldiimidazole was added (0.81 g), and the reaction stirred overnight. The acetonitrile was evaporated in vacuo, the residue partitioned between water and chloroform, and the organic phase washed with saturated brine and dried over magnesium sulfate. The crude product was purified by chromatography (silica gel, 1.2 to 2.5% methanol in methylene chloride gradient elution), which gave the title compound (1.09 g). ¹H NMR (500 MHz, CDCl₃) δ 9.39 (br s, AH), 8.04 (dd, J=5, 1 Hz, 1H), 7.33 (dd, J=8, 1 Hz, 1H), 6.99 (dd, J=8, 5 Hz, 1H), 4.50 (m, 1H), 4.32 (br s, 2H), 2.86 (br s, 2H), 2.20 (m, 2H), 1.86 (d, J=12 Hz, 2H), 1.50 (s, 9H).

Step C. 2-Oxo-1-(4-piperidinyl)-2,3-dihydro-1H-imidazo[4,5-b]pyridine dihydrochloride 2-Oxo-1-(1-tert-butoxycarbonylpiperidin-4-yl)-2,3-dihydro-1H-imidazo[4,5-b]pyridine (1.03 g, 3.23 mmol) was dissolved ill methanol (25 mL) and a solution of 2 N hydrochloric acid in ether (8 mL) was added at room temperature. After 2 h, the volatiles were removed in vacuo, to give the title compound (0.92 g). MS 219 (M+1). ¹H NMR (500 MHz, CD₃OD) δ 8.01 (dd, J=6, 1 Hz, 1H), 7.83 (d, J=8 Hz, 1H), 7.28 (dd, J=8, 6 Hz, 1H), 4.60 (m, 1H), 3.59 (d, J=12 Hz, 2H), 3.21 (t, J=12 Hz, 2H), 2.70 (dq, J=13, 4 Hz, 2H), 2.12 (d, J=13 Hz, 2H).

INTERMEDIATE 2

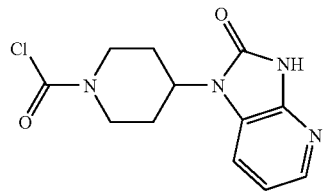

4-(2-Oxo-2,3-dihydro-1H-imidazo[4,5-b]pyridin-1-yl)piperidine-1-carbonyl chloride Phosgene (20% wt. in toluene; 1.8 mL, 3.43 mmol) was added to a suspension of 2-oxo-1-piperidinium-4-yl-2,3-dihydro-1H-imidazo[4,5-b]pyridin-4-ium dichloride (100 mg, 0.343 mmol) and 2,6-lutidine (0.50 mL, 4.293 mmol) in dichloromethane (5 mL) at 0° C. After 2 h, the solution was added to saturated aqueous sodium bicarbonate and extracted with ethyl acetate. The organic layer was washed with water (2×), saturated brine, dried over magnesium sulfate, filtered and concentrated. Dichloromethane (10 mL) was added, and the mixture was filtered to give the title compound as a solid (48 mg). MS 281 (M+1). ¹H NMR (500 MHz, (CD₃)₂SO) δ 11.58 (s, 1H), 7.90 (d, J=5.1 Hz, 1H), 7.67 (d, J=7.6 Hz, 1H), 7.01-6.99 (m, 1H), 4.52-4.46 (m, 1H), 4.31-4.23 (m, 2H), 3.38-3.33 (m, 1H), 3.19-3.14 (m, 1H), 2.32-2.24 (m, 2H), 1.84-1.81 (m, 2H).

INTERMEDIATE 3

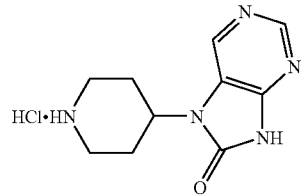

7-Piperidin-4-yl-7,9-dihydro-8H-purin-8-one hydrochloride

Step A. 4-Amino-5-[(1-tert-butoxycarbonylpiperidin-4-yl)amino)pyrimidine

A mixture of 4,5-diaminopyrimidine (1.0 g, 9.1 mmol), N-(tert-butoxycarbonyl)-4-piperidone (3.0 g, 15 mmol) and sodium triacetoxyborohydride (1.2 g, 5.6 mmol) in dichloroethane (60 mL) was stirred at room temperature for 3 d. The reaction was partitioned between chloroform (200 mL) and 3 N sodium hydroxide (30 mL). After drying over magnesium sulfate, the organic phase was concentrated to give the title compound as a tan gum. MS 294 (M+1)

Step B. 7-(1-Benzylpiperidin-4-yl)-7,9-dihydro-8H-purin-8-one

The crude product from Step A, 4-amino-5-[(1-tert-butoxycarbonylpiperidin-4-yl)amino)pyrimidine, was refluxed with carbonyldiimidazole (3.0 g, 18 mmol) in tetrahydrofuran (250 mL) for 2 d, cooled and concentrated. The crude product was dissolved in ethyl acetate (25-50 mL), which in four crops gave the title compound as a white crystalline solid (1.3 g). MS 320 (M+1)

Step C. 7-Piperidin-4-yl-7,9-dihydro-8H-purin-8-one hydrochloride

A mixture of 7-(1-benzylpiperidin-4-yl)-7,9-dihydro-8H-purin-8-one (1.2 g, 3.7 mmol) in 4 N hydrogen chloride in dioxane (50 mL), was stirred vigorously at room temperature for 3 h. The reaction was concentrated in vacuo to give the title compound as a white solid. MS 220 (M+1)

INTERMEDIATE 4

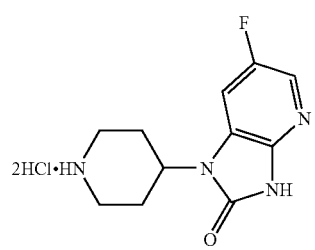

4-Fluoro-2-oxo-1-(4-piperidinyl)-2,3-dihydro-1H-imidazo[4,5-b]pyridine

Step A.
N-(5-Fluoropyridin-2-yl)-2,2-dimethylpropanamide

To a 0° C. solution of 2-amino-5-fluoropyridine (1.00 g, 8.92 mmol) and triethylamine (1.35 g, 13.4 mmol) in dichloromethane (30 mL) was added trimethylacetyl chloride (1.29 g, 10.7 mmol) and DMAP (0.11 g, 0.89 mmol). The solution was allowed to warm to room temperature. After 4 h, saturated aqueous $NaHCO_3$ was added, the layers separated and the aqueous phase backwashed with DCM. The combined organics were dried over magnesium sulfate, filtered and concentrated and the residue purified by silica gel chromatography (5%→40% EtOAc/hexanes) to give the title compound (1.34 g). MS 197.3 (M+1).

Step B. N-(3-Azido-5-fluoropyridin-2-yl)-2,2-dimethylpropanamide

To a –78° C. solution of N-(5-fluoropyridin-2-yl)-2,2-dimethylpropanamide (1.34 g, 6.83 mmol) in tetrahydrofuran (25 mL) was added tert-butyllithium (1.31 mL of a 1.7 M solution, 20.5 mmol) dropwise. After 3 h at –78° C., 4-dodecylbenzenesulfonyl azide (3.60 g, 10.2 mmol) was added at the reaction was allowed to warm to room temperature. After 1 h, saturated aqueous $NH_4Cl$ was added, and the tetrahydrofuran was removed via rotary evaporator. Dichloromethane was added, the layers separated and the aqueous phase backwashed with DCM. The combined organics were dried over magnesium sulfate, filtered and concentrated and the residue purified by two successive silica gel chromatographies (10%→80% EtOAc/hexanes, then 5%→42% EtOAc/hexanes) to give the title compound (0.275 g).
MS 234.0 (M+1).

Step C. 3-Azido-5-fluoropyridin-2-amine

N-(3-Azido-5-fluoropyridin-2-yl)-2,2-dimethylpropanamide (275 mg, 1.16 mmol) in 3 N HCl (5 mL) was heated to 100° C. After 2 h, the volatiles were removed in vacuo, to give the title compound as its HCl salt (180 mg). MS 154.2 (M+1).

Step D. 5-Fluoropyridine-2,3-diamine

The HCl salt of 3-azido-5-fluoropyridin-2-amine (1.90 g, 10.0 mmol) was dissolved in tetrahydrofuran (100 mL) and treated with MP-Carbonate (Argonaut, 11.5 g). After 1 h, the mixture was filtered, rinsed with more tetrahydrofuran, and concentrated. This residue was dissolved in ethanol (50 mL), purged with argon, and 10% palladium on carbon was added (0.15 g). Hydrogen was introduced (1 atm) and the reaction stirred until complete. The catalyst was filtered and the solvent evaporated from the filtrate to give the title compound (1.18 g). MS 128.0 (M+1)

Step E. tert-Butyl 4-[(2-amino-5-fluoropyridin-3-yl)amino]piperidine-1-carboxylate Sodium triacetoxyborohydride (2.95 g, 13.9 mmol) was added to a solution of 5-fluoropyridine-2,3-diamine (1.18 g, 9.28 mmol), acetic acid (0.56 g, 9.28 mmol) and 1-(t-butoxycarbonyl)-4-piperidone (1.85 g, 9.28 mmol) in 1,2-dichloroethane (20 mL) at room temperature. After 1 h, the reaction was quenched with water (20 mL) and extracted with dichloromethane. After drying over sodium sulfate, the solution was filtered and evaporated to give the crude product. This was purified by chromatography, (silica gel, 5%→15% MeOH/DCM; then C-18, 95% water/acetonitrile→5% water/acetonitrile with 0.1% trifluoroacetic acid) to give the title compound (0.73 g). MS 311.2 (M+1).

Step F. tert-Butyl 4-(6-fluoro-2-oxo-2,3-dihydro-1H-imidazo[4,5-b]pyridin-1-yl)piperidine-1-carboxylate Carbonyldiimidazole (1.53 g, 9.41 mmol) was added to a solution of tert-butyl 4-[(2-amino-5-fluoropyridin-3-yl)amino]piperidine-1-carboxylate (0.73 g, 2.35 mmol) in acetonitrile (10 mL) at room temperature. The reaction was stirred until all the starting material was consumed (approximately 2 h) and then the solvent was evaporated in vacuo. The residue was diluted with water, extracted with dichloromethane (3×), dried over magnesium sulfate and then concentrated. The crude product was purified by chromatography (silica gel, 1% to 10% methanol in methylene chloride gradient elution), which gave the title compound (0.309 g). MS 337.2 (M+1)

Step G. 4-Fluoro-2-oxo-1-(4-piperidinyl)-2,3-dihydro-1H-imidazo[4,5-b]pyridine tert-Butyl 4-(6-fluoro-2-oxo-2,3-dihydro-1H-imidazo[4,5-b]pyridin-1-yl)piperidine-1-carboxylate (340 mg, 1.01 mmol) was dissolved in dichloromethane (5 mL) and trifluoroacetic acid (5 mL) was added. After 2 h, the reaction was concentrated, diluted with dichlormethane (5 mL) and a solution of 1 N hydrochloric acid in 1,4-dioxane (2 mL) was added at room temperature. Concentration afforded the title compound (302 mg). MS 237.2 (M+1) $^1$H NMR (500 MHz, $CD_3OD$) δ 7.92 (br s, 1H), 7.70 (dd, 1H), 4.60 (m, 1H), 3.60 (s, 2H), 3.25 (dd, 2H), 2.70 (m, 2H), 2.10 (d, 2H).

INTERMEDIATE 5

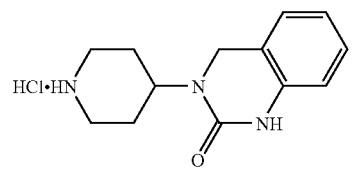

3-(4-Piperidinyl-3,4-dihydroquinazolin-2(1H)-one hydrochloride

The title compound was prepared according to the procedure described by H. Takai et al., in Chem. Pharm. Bulletin 1985, 33(3) 1116-1128. $^1$H NMR (500 MHz, DMSO-$d_6$) δ 9.31 (s, 1H), 8.79 (br s, 1H), 8.58 (br s, 1H), 7.13 (t, J=8 Hz, 2H), 6.88 (t, J=8 Hz, 1H), 6.77 (d, J=8 Hz, 1H), 4.37 (tt, J=12, 4 Hz, 1H), 4.29 (s, 2H), 3.00 (q, J=11 Hz, 2H), 2.06 (dq, J=4, 12 Hz, 2H), 1.73 (d, J=12 Hz, 2H).

INTERMEDIATE 6

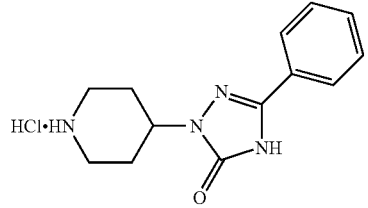

5-Phenyl-1-piperidin-4-yl-2,4-dihydro-3H-1,2,4-triazol-3-one hydrochloride

Step A: 9H-Fluoren-9-ylmethyl 4-[(t-butoxacarbonyl)hydrazono]piperidine-1-carboxylate A solution of 1-[(9H-fluoren-9-yl)methyloxycarbonyl]-4-piperidone (16.0 g, 50.0 mmol) and tert-butyl carbazate 7.25 g, 55.5 mmol) in ethanol (250 mL) was refluxed for 1 h. The solution was cooled and concentrated. Addition of ether (100 mL) produced the title compound as a white precipitate (21.0 g). $^1$H NMR (500 MHz, CDCl$_3$) δ 7.77 (d, J=7 Hz, 2H), 7.57 (d, J=7 Hz, 2H), 7.40 (t, J=7 Hz, 2H), 7.32 (t, J=7 Hz, 2H), 4.50 (br s, 2H), 4.24 (t, J=6 Hz, 1H), 3.4-3.7 (br m, 4H), 2.47 (br s, 2H), 2.2-2.1 (br m, 2H), 1.56 (s, 9H).

Step B: 9H-Fluoren-9-ylmethyl 4-[(t-butoxycarbonyl)hydrazino]piperidine-1-carboxylate A solution of 9H-fluoren-9-ylmethyl 4-[(t-butoxycarbonyl)hydrazono]piperidine-1-carboxylate (10.0 g, 22.9 mmol) in acetic acid (150 mL) was shaken with platinum oxide (1.0 g) under 45 psi hydrogen on a Parr apparatus for 2 h. The solution was filtered and concentrated to give the title compound.

Step C: 9H-Fluoren-9-ylmethyl 4-hydrazinopiperidine-1-carboxylate

A solution of 9H-fluoren-9-ylmethyl 4-[(tert-butoxycarbonyl)hydrazino]piperidine-1-carboxylate (20 g, 45.7 mmol) was dissolved in trifluoroacetic acid (100 mL) and stirred at room temperature for 1.5 h. The reaction was concentrated and the residue dissolved in methanol and purified by reverse phase HPLC. Pure fractions were isolated and combined to give the trifluoroacetic acid salt of the title compound (3.01 g). $^1$H NMR (500 Mz, DMSO-d$_6$) δ 7.89 (d, J=8 Hz, 2H), 7.61 (d, J=8 Hz, 2H), 7.40 (t, J=8 Hz, 2H), 7.32 (t, J=8 Hz, 2H), 4.33 (d, J=6 Hz, 2H), 4.25 (t, J=6 Hz, 1H), 4.0-3.5 (br s, 6H), 3.05 (br s, 1H), 2.80 (br s, 2M, 1.89 (br s, 2H), 1.2 (br s, 2H).

Step D: 9H-Fluoren-9-ylmethyl 4-(5-oxo-3-phenyl-4,5-dihydro-1H-1,2,4-triazol-1-yl)piperidine-1-carboxylate A solution of 9H-fluoren-9-ylmethyl 4-hydrazinopiperidine-1-carboxylate trifluoroacetic acid salt (2.95 g, 6.54 mmol) was refluxed for 2 h with ethyl N-benzothioyl carbamate (1.50 g, 7.1 mmol) (prepared by the procedure of E. P. Papadopoulus, *J. Org. Chem.*, 1976, 41(6) 962-965) in tetrahydrofuran (30 mL) with diisopropylethyl amine (1.25 mL, 7.1 mmol). The reaction was cooled and concentrated, then dissolved with heating in acetonitrile. A white solid crystallized upon cooling, giving the title compound (2.06 g). $^1$H NMR (500 MHz, CDCl$_3$) δ 7.80 (d, J=7 Hz, 2H), 7.77 (d, J=7 Hz, 2H), 7.61 (d, J=7 Hz, 2H), 7.48 (m, 3H), 7.40 (t, J=7 Hz, 2H), 7.33 (t, J=7 Hz, 2H), 4.46 (d, J=6 Hz, 2H), 4.36 (m, 2H), 4.27 (t, J=6 Hz, 1H), 4.26 (br s, 1H), 3.02 (br s, 2H), 2.04 (br s, 2H), 1.94 (br m, 2H).

Step E: 5-Phenyl-1-piperidin-4-yl-2,4-dihydro-3H-1,2,4-triazol-3-one hydrochloride A solution of 9H-fluoren-9-ylmethyl 4-(5-oxo-3-phenyl-4,5-dihydro-1H-1,2,4-triazol-1-yl)piperidine-1-carboxylate (2.06 g, 4.41 mmol) and diethylamine (15 mL) in tetrahydrofuran (15 mL) was stirred at room temperature for 2 h. The reaction was concentrated and the crude product purified by column chromatography (silica gel, 0 to 10% {5% ammonium hydroxide/methanol} in dichloromethane gradient elution), giving the title compound as a white solid (0.95 g). $^1$H NMR (500 MHz, CDCl$_3$) δ 7.84 (d, J=7 Hz, 2H), 7.47 (m, 31), 4.30 (m, 1H), 3.25 (d, J=13 Hz, 2H), 2.79 (t, J=13 Hz, 2H), 2.04 (d, J=4, 12 Hz, 2), 1.93 (br d, J=10 Hz, 2H).

INTERMEDIATE 7

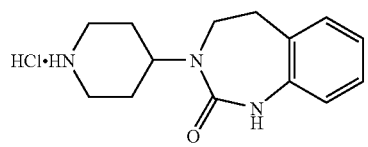

3-(4-Piperidinyl)-1,3,4,5-tetrahydro-2H-1,3-benzodiazapin-2-one hydrochloride

Step A. 2-(2-Bromoethyl)nitrobenzene

Triphenylphosphine (39.2 g, 0.150 mol) and carbon tetrabromide (49.5 g, 0.150 mol) were added sequentially to a solution of 2-(2-hydroxyethyl)-nitrobenzene (25.0 g, 0.150 mol) in methylene chloride (400 mL) at 0° C. The reaction was stirred overnight and quenched with saturated sodium bicarbonate solution. The methylene chloride phase was washed with saturated brine and dried over magnesium sulfate. The crude product was treated with ethyl acetate, and the precipitated triphenylphosphine oxide removed by filtration. Further purification by flash chromatography by (silica gel, 0-10% ethyl acetate in hexane gradient elution) produced the title compound (27.9 g).

Step B. 2-(2-Azidoethyl)nitrobenzene

Sodium azide (22.8, 0.351 mol) in water (60 mL) was added to a solution of 2-(2-bromoethyl)-nitrobenzene (27.9 g, 0.121 mol) in acetonitrile (120 mL). The reaction was refluxed for 4 h, cooled, and partitioned between methylene chloride and water. The organic phase was washed with saturated brine, and dried over magnesium sulfate. The title compound was obtained as an oil (22.8 g).

Step C. 2-(2-Aminoethyl)nitrobenzene

Triphenylphosphine (31.1 g; 0.118 mol) and calcium carbonate (50 mg, 0.5 mmol) were added to a solution of 2-(2-azidoethyl)nitrobenzene (22.8 g, 0.118 mol) in benzene (500 mL). The reaction was stirred at room temperature until complete. The solvent was removed in vacuo, and the residue treated with acetic acid (100 mL) and 48% hydrogen bromide (100 mL) at 100° C. for 1 h. The reaction was cooled and concentrated. Water was added and the solution extracted with methylene chloride. The aqueous layer was made basic by the addition of 5% aqueous sodium hydroxide solution, then extracted with ethyl acetate. The organic phase was washed with saturated brine and dried over sodium sulfate. The title compound was obtained as all oil (8.0 g). MS 167 (M+1).

Step D. t-Butyl 4-{[2-(2-nitrophenyl)ethyl]amino}piperidine-1 carboxylate

A solution of 2-(2-aminoethyl)nitrobenzene (8.00 g, 48.1 mmol) and 1-t-butoxycarbonyl-4-piperidinone (9.59 g, 48.1 mmol) in methanol (100 mL) was brought to pH 5 by the addition of acetic acid. Sodium cyanoborohydride (4.53 g, 72.2 mmol) was added and the reaction stirred for 3 h. Methanol was removed in vacuo, and the residue partitioned between ethyl acetate and saturated sodium bicarbonate solution. The organic phase was washed with saturated brine and dried over sodium sulfate. The title compound was obtained as an oil (19.27 g). MS 350 (M+1).

Step E. t-Butyl 4-{[2-(2-aminophenyl)ethyl] amino}piperidine-1-carboxylate tert-Butyl 4-{[2-(2-nitrophenyl)ethyl]amino}piperidine-1-carboxylate and 10% palladium on carbon (1.9 g) were stirred in ethanol (250 mL) overnight under one atmosphere hydrogen. Catalyst was filtered from the solution and solvent removed in vacuo to provide the title compound (17.2 g). MS 320 (M+1)

Step F. 3-(1-t-Butoxycarbonyl-4-piperidinyl)-1,3,4,5-tetrahydro-2H-1,3-benzodiazapin-2-one Carbonyldiimidazole (8.73 g, 53.8 mmol) was added to a solution of tert-butyl 4-{[2-(2-aminophenyl)ethyl]amino}piperidine-1-carboxylate (17.2 g, 53.8 mmol) in dimethylformamide (200 mL), and stirred at room temperature for 2 h. The reaction was diluted with ethyl acetate and extracted with water, then saturated brine. The crude product was purified by chromatography (silica gel, 0-30% ethyl acetate in methylene chloride gradient elution). The title compound was obtained as a dark solid (4.8 g).

Step G. 3-(4-Piperidinyl)-1,3,4,5-tetrahydro-2H-1,3-benzodiazapin-2-one hydrochloride A solution of 3-(1-t-butoxycarbonyl-4-piperidinyl)-1,3,4, 5-tetrahydro-2H-1,3-benzodiazapin-2-one (4.80 g, 13.9 mmol) in ethyl acetate (300 mL) was saturated with hydrogen chloride gas at 0° C. The reaction was allowed to warm to room temperature and stirred overnight. The solid was filtered and washed with ethyl acetate. The ethyl acetate filtrate was concentrated for a second crop. The title compound was obtained as a solid (2.94 g). MS 246 (M+1). $^1$H NMR (500 Mz, CD$_3$OD) δ 7.10 (m, 2H), 6.94 (d, J=8 Hz, 11H), 6.91 (t, J=8 Hz, 11), 4.35 (tt, J=10, 1 Hz, 11H), 3.52 (m, 4H), 3.12 (t, J=12 Hz, 211), 3.05 (m, 2H), 2.07 (qd, J=12, 4 Hz, 2H), 1.99 (m, 2H).

INTERMEDIATE 8

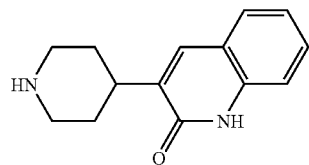

3-(4-Piperidinyl)quinolin-2-(1H)-one

Step A. 3-(1-Benzyl-4-hydroxypiperidin-4-yl)-2-chloroquinioline

A solution of n-butyllithium in hexane (1.6 M, 38.2 mL, 61.1 mmol) was added to a solution of diisopropylamine (8.6 mL, 61.1 mmol) in tetrahydrofuran (140 mL) at −78° C. under argon. After 1 h, a solution of 2-chloroquinoline (10.00 g, 61.1 mmol) in tetrahydrofuran (30 mL) was added via syringe. After 1 h, a solution of 1-benzyl-4-piperidinone (11.3 mL, 61.1 mmol) was added, and the reaction stirred for an additional 40 min at −78° C., then allowed to warm to room temperature. The reaction was cooled to −20° C. and quenched with water. The reaction solution was extracted with ethyl acetate, and the organic phase washed with saturated brine and dried over magnesium sulfate. Chromatographic purification (silica gel, 0 to 10% {5% ammonium hydroxide/methanol} in methylene chloride gradient elution) gave the title compound, 11.3 g. MS 353 (M+1). $^1$H NMR (500 MHz, CDCl$_3$) δ 8.33 (s, 1H), 8.00 (d, J=8 Hz, 1H), 7.82 (d, J=8 Hz, 1H), 7.72 (dt, J=11 Hz, 1H), 7.57 (dt, J=1.8 Hz, 1H), 7.39-7.26 (m, 5H), 3.61 (s, 2H), 2.85 (d, J=11 Hz, 2H), 2.59 (t, J=12 Hz, 2H), 2.48 (dt, J=413 Hz, 2H), 2.13 (d, J=12 Hz, 2H).

Step B. 3-(1-Benzyl-1,2,3,6-tetrahydropyridin-4-yl) quinolin-2-(1H)-one 3-(1-Benzyl-4-hydroxypiperidin-4-yl)-2-chloroquinoline (11.0 g, 31.1 mmol) was refluxed in 6 N hydrochloric acid for 8 h. The solution was cooled and water (100 mL) added. The precipitated solid was collected and dried to give the title compound, 7.9 g. MS 317 (M+1). $^1$H NMR (500 MHz, CD$_3$OD) δ 7.97 (s, 1H), 7.70 (d, J=7 Hz, 1H), 7.60 (m, 2H), 7.55 (m, 4H), 7.35 (d, J=9 Hz, 1H), 7.27 (t, J=8 Hz, 1H), 6.50 (m, 1H), 4.49 (ABq, I=13 Hz, Δv=16 Hz, 2H), 3.92 (m, 2H), 3.76 (dt, J=12.4 Hz, 1H), 3.40 (m, 1H), 2.96 (m, 2H).

Step C. 3-(4-Piperidinyl)quinolin-2-(1)-one

A solution of 3-(1-benzyl-1,2,3,6-tetrahydropyridin-4-yl) quinolin-2-(1H)-one (4.00 g, 12.6 mmol) in methanol (500 mL) was degassed with argon, and 10% palladium on carbon (1.2 g) added. The reaction was placed under 1 atm hydrogen and heated to 50° C. for 5.5 h. The reaction was cooled and filtered through celite. Concentration provided the title compound, 2.7 g. MS 229 (M+1). $^1$H NMR (500 MHz, CD$_3$OD) δ 7.80 (s, 1H), 7.67 (d, J=8 Hz, 1H), 7.51 (t, J=8 Hz, 1H), 7.33 (d, J=8 Hz, 1H), 7.25 (t, J=8 Hz, 1H), 3.52 (t, J=12 Hz, 2H), 3.17 (dt, J=3, 13 Hz, 211), 3.15 (m, overlaps with o 3.17 peak, 1H), 2.18 (d, J=14 Hz, 2H), 1.91 (dq, J=3, 12 Hz, 2H).

INTERMEDIATE 9

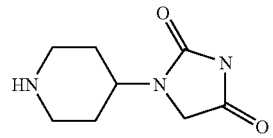

1-Piperidin-4-ylimidazolidine-2,4-dione

Step A: tert-Butyl 4-[(2-ethoxy-2-oxoethyl)amino]piperidine-1 carboxylate

Sodium cyanoborohydride (189 mg, 3.01 mmol) was added to a solution of 1-boc-4-piperidone (500 mg, 2.51 mmol) and glycine ethyl ester hydrochloride (350 mg, 2.51 mmol) in methanol (12.5 mL). After 16 h, the mixture was quenched with saturated ammonium chloride solution, concentrated, and partitioned between dichloromethane and saturated sodium bicarbonate solution. The organic layer was washed with brine, dried over magnesium sulfate, filtered, and concentrated. Purification by silica gel chromatography [100% dichloromethane→95% dichloromethane/5% (10% ammonium hydroxide/methanol)] gave the title compound (600 mg).

Step B: tert-Butyl 4(2,4-dioxoimidazolidin-1-yl) piperidine-1-carboxylate

Potassium cyanate (31 mg, 0.384 mmol) was added to a solution of tert-butyl 4-[(2-ethoxy-2-oxoethyl)amino]piperidine-1-carboxylate (100 mg, 0.384 mmol) in water (2 mL). Acetic acid was then added to adjust pH of reaction to 4-5 and the mixture was heated at 40° C. After 16 h, the reaction was cooled to ambient temperature and purified by reverse phase HPLC(C-18, 95% water/acetonitrile→5% water/acetonitrile with 0.1% trifluoroacetic acid) to give the title compound (33 mg).

Step C: 1-Piperidin-4-ylimidazolidine-2,4-dione

Trifluoroacetic acid (0.300 mL) was added to a solution of tert-butyl 4-(2,4-dioxoimidazolidin-1-yl)piperidine-1-carboxylate (32 mg, 0.113 mmol) in dichloromethane (1 mL). After 4 h, the reaction was concentrated to give the title compound. MS184.04 (M+1).

INTERMEDIATE 10

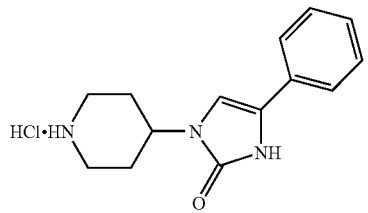

4-Phenyl-1-piperidin-4-yl-1,3-dihydro-2H-1-imidazol-2-one hydrochloride

4-Phenyl-1-piperidin-4-yl-1,3-dihydro-2H-imidazol-2-one hydrochloride was prepared according to the procedure described in U.S. Pat. No. 6,344,449 B1.

INTERMEDIATE 11

Spiro[piperine-4,3'-pyrrolo[2,3-b]pyridin]-2'(1'H)-one dihydrochloride

Step A. 1-{[2-Trimethylsilyl)ethoxy]methyl}-1H-pyrrolo[2,3-b]pyridine

Sodium hydride (60% dispersion in mineral oil; 16.2 g, 0.404 mol) was added in portions over 25 min to a solution of 7-azaindole (39.8 g, 0.337 mol) in DMF (200 mL) at 0° C. and the mixture was stirred for 1 h. 2-(Trimethylsilyl)ethoxymethyl chloride (71.8 mL, 0.404 mol) was then added slowly over 15 min, keeping the temperature of the reaction mixture below 10° C. After 1 h, the reaction was quenched with $H_2O$ (500 mL) and the mixture was extracted with $CH_2Cl_2$ (5×300 mL). The combined organic layers were washed with brine, dried over $MgSO_4$, filtered, concentrated and dried under high vacuum to give the title compound. MS: m/z=249 (M+1).

Step B. 3,3-Dibromo-1-{[2-(trimethylsilyl)ethoxy] methyl}-1,3-dihydro-2H-pyrrolo[2,3-b]pyridin-2-one A solution of 1-{[2-(trimethylsilyl)ethoxy]methyl}-1H-pyrrolo[2,3-b]pyridine from Step A (43.1 g, 0.174 mol) in dioxane (300 mL) was added dropwise over 30 min to a suspension of pyridine hydrobromide perbromide (277 g, 0.868 mol) in dioxane (300 mL). The reaction was stirred at ambient temperature using an overhead mechanical stirrer. After 60 min, the biphasic reaction mixture was quenched with $H_2O$ (300 mL) and extracted with EtOAc. The aqueous layer was washed with EtOAc (2×300 mL) and the combined organic layers were washed with $H_2O$ (4×300 mL; the final wash was pH 5-6), then brine (300 mL), then dried over $MgSO_4$, filtered and concentrated under reduced pressure. The crude product was immediately dissolved in $CH_2Cl_2$ and the solution filtered through a plug of silica, eluting with $CH_{12}Cl_2$ until the dark red color had completely eluted from the plug. The filtrate was washed with saturated aqueous $NaHCO_3$ (400 mL), then brine (400 mL), dried over $MgSO_4$ and concentrated in vacuo to give the title compound. MS: m/z=423 (M+1).

Step C. 1-{[2-(Trimethylsilyl)ethoxy]methyl}-1,3-dihydro-2H-pyrrolo[2,3-b]pyridin-2-one Zinc (100 g, 1.54 mol) was added to a solution of 3,3-dibromo-1-{[2-(trimethylsilyl)ethoxy]methyl}-1,3-dihydro-2H-pyrrolo[2,3-b]pyridin-2-one from Step B (65 g, 0.154 mol) in THF (880 mL) and saturated aqueous ammonium chloride (220 mL). After 3 h, the reaction was filtered and concentrated in vacuo. The residue was partitioned between EtOAc and $H_2O$ which resulted in the formation of a white precipitate. Both layers were filtered through a Celite pad and the layers were separated. The aqueous layer was washed with EtOAc (2×) and the combined organic layers were washed with $H_2O$, dried over $MgSO_4$, filtered, and concentrated. The crude product was filtered through a plug of silica gel eluting with $CH_2Cl_2$:EtOAc-90:10 and the eluant was concentrated under reduced pressure to provide the title compound. MS: m/z=265 (M+1).

Step D. spiro[cylopent-3-ene-1,3'-pyrrolo[2,3-b] pyridin]-2'(1'H)-one

To a solution of cis-1,4-dichloro-2-butene (1.98 g, 15.8 mmol) and 1-{[2-(trimethylsilyl)ethoxy]methyl}-1,3-dihydro-2H-pyrrolo[2,3-b]pyridin-2-one (3.49 g, 13.2 mmol) in DMF (175 mL) was added cesium carbonate (10.7 g, 32.9 mmol). After 24 h the reaction mixture was partitioned between $Et_2O$ (200 mL) and $H_2O$ (200 mL). The aqueous layer was extracted further with $Et_2O$ (2×200 mL). The combined organic layers were washed with $H_2O$ (2×100 mL), then brine (100 mL), dried over $MgSO_4$, filtered, and concentrated under reduced pressure. To a solution of this material in dichloromethane (150 mL) was added trifluoroacetic acid (150 mL). After 1 h, the reaction was concentrated, dissolved in EtOH (150 mL) and 2N HCl (150 mL) was added. This mixture was heated at 45° C. for 48 h. The mixture was concentrated, diluted with saturated aqueous $NaHCO_3$, and extracted with dichloromethane (2×). The combined organic layers were dried and concentrated. The crude product was purified by silica gel chromatography, eluting with a gradient of 0 to 5% methanol:dichloromethane to give the title compound (0.62 g). MS: m/z=187.1 (M+1).

Step E. 3,4-dihydroxyspiro[cyclopentane-1,3'-pyrrolo[2,3-b]pyridin]-2'(1'H)-one

To a mixture of trimethylamine-N-oxide dihydrate (408 mg, 3.67 mmol) and spiro[cyclopent-3-ene-1,3'-pyrrolo[2,3-b]pyridin]-2'(1'H)-one (622 mg, 3.34 mmol) in dichloromethane (115 mL) was added osmium tetroxide (25 uL of 2.5% solution in 2-methyl-2-propanol). After 24 h the reaction mixture was concentrated. The crude product was loaded onto a silica gel chromatography column with a minimal amount of methanol and eluted with a gradient of 5 to 20% methanol: dichloromethane to give the title compound (0.63 g). MS: m/z=221.0 (M+1).

Step F. tert-butyl 2'-oxo-1',2'-dihydro-1H-spiro[piperidine-4,3'-pyrrolo[2,3-b]pyridine]-1-carboxylate To a mixture of 3,4-dihydroxyspiro[cyclopentane-1,3'-pyrrolo[2,3-b]pyridin]-2'(1'H)-one (640 mg, 2.91 mmol) in 3:1 ethanol:water (160 mL) was added sodium periodate (622 mg, 2.91 mmol). Upon consumption of the starting material, ammonium hydroxide (50 mL) was slowly added to the reaction mixture. Palladium hydroxide (200 mg, 20%) was added and the reaction was hydrogenated at 50 psi. After 24 b, 200 mg of palladium hydroxide was added and the hydrogenation continued for an additional 24 h. The reaction mixture was filtered through celite and concentrated. This material was dissolved in DMF (10 mL) and di-tert-butyl dicarbonate (635 mg, 2.91 mmol) was added followed by triethylamine (0.811 mL, 5.82 mmol). After 24 h, the reaction was diluted with saturated aqueous NaHCO₃ and extracted with ether (3×). The combined organic layers were washed with water (3×), dried and concentrated. The crude product was purified by silica gel chromatography, eluting with a gradient of 0 to 10% methanol: dichloromethane to give the title compound (489 mg). MS: m/z=304.1 (M+1).

Step G. Spiro[piperidine-4,3'-pyrrolo[2,3-b]pyridin]-2'(1'H)-one dihydrochloride tert-Butyl 2'-oxo-1',2'-dihydro-1H-spiro[piperidine-4,3'-pyrrolo[2,3-b]pyridine]-1-carboxylate (451 mg, 1.49 mmol) was dissolved in ethyl acetate (3 mL) and a solution of 4N hydrochloric acid in dioxane (7.5 mmol) was added at room temperature. After 24 h, the volatiles were removed in vacuo, to give the title compound (404 mg). MS 204.1 (M+1). ¹H NMR (500 MHz, CD₃OD) δ 8.31 (d, J=7.1 Hz, 1H), 8.20 (d, J=6.1 Hz, 1H), 7.45 (dd, J=6.8, 6.8 Hz, 1H), 3.74 (brdd, 2H), 3.47 (brdd, 2H), 2.35 (brddd, 2H), 2.21 (brd, 2H).

Spiro[piperidine-4,4'-pyrido[2,3-d][1,3]oxazin]-2' (1'H)-one

Step A. tert-Butyl (6-chloropyridin-2-yl)carbamate

To a solution of 2-amino-6-chloropyridine (5.24 g, 40.8 mmol) and sodium hexamethyldisilazide (1.0 M, 89.8 mL, 89.8 mmol) in THF (35 mL) was added a solution of di-tert-butyl dicarbonate (9.80 g, 44.9 mmol) in THF (35 mL). After 24 h the reaction was concentrated and the residue was partitioned between EtOAc (30 mL) and 1N HCl (100 mL). The aqueous layer was extracted further with EtOAc (2×). The combined organic layers were washed with NaHCO₃, dried over MgSO₄, filtered, and concentrated under reduced pressure. The crude product was purified by silica gel chromatography, eluting with a gradient of 20 to 100% dichloromethane: hexane to give the title compound (7.73 g). MS: m/z 173.0 (M-ᵗBu).

Step B. Benzyl 7'-chloro-2'-oxo-1',2'-dihydro-H-spiro[piperidine-4,4'-pyrido[2,3-d][1,3]oxazine]-1-carboxylate To a −20° C. solution of N,N,N',N'-tetramethylethylenediamine (0.335 g, 2.89 mmol) in THF (1 mL) was added n-butyllithium (2.5M, 1.15 mL, 2.89 mmol) over 10 min. After 30 min, the mixture was cooled to −78° C. and tert-butyl (6-chloropyridin-2-yl)carbamate (0.300 g, 1.31 mmol) in THF (0.8 mL) was added over 15 min. After 1 h, the reaction was warmed to −50° C., stirred for 2 h and then N-benxyloxycarbonyl-4-piperidinone (0.459 g, 1.97 mmol) in THF (1 mL) was added over 10 min. The reaction was allowed to warm to room temperature and then stirred for 24 h. A solution of saturated aqueous NaHCO₃ was added and the mixture extracted with EtOAc (3×). The combined organic layers were washed with H₂O, brine, dried over MgSO₄, filtered, and concentrated under reduced pressure. The crude product was purified by silica gel chromatography, eluting with a gradient of 25 to 50% ethyl acetate:hexane to give the title compound (0.160 g). MS: m/z=338.0 (M+1).

Step C. Spiro[piperidine-4,4'-pyrido[2,3-d][1,3]oxazin]-2'(1'H-one

10% Palladium on carbon (300 mg) was added to a solution of benzyl 7'-chloro-2'-oxo-1',2'-dihydro-1H-spiro[piperidine-4,4'-pyrido[2,3-d][1,3]oxazine]-1-carboxylate (1.85 g, 1.77 mmol) in EtOH (250 mL). The reaction vessel was evacuated and back-filled with nitrogen (3×), then back-filled with hydrogen (1 atm). After 24 h, the mixture was filtered though celite and concentrated to give the title compound (1.07 g). MS 220.1 (M+1). ¹H NMR (500 MHz, CD₃OD) δ 8.26 (dd, J=1.7, 5.0 Hz, 1H), 7.69 (dd, J=1.6, 7.7 Hz, 1H), 7.16 (dd, J=5.0, 7.7 Hz, 1H), 3.49-3.42 (m, 4H), 2.38-2.25 (m, 4H).

INTERMEDIATE 12

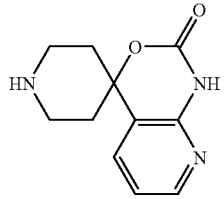

INTERMEDIATE 13

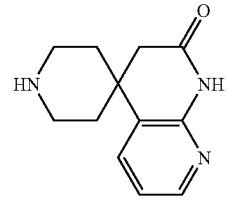

1H-Spiro[1,8-naphthyridine-4,4'-piperidin]-2(3H)-one

Step A. Benzyl 4-(2-methoxy-2-oxoethylidene)piperidine-1-carboxylate

A solution of N-benxyloxycarbonyl-4-piperidinone (5.0 g, 21.4 mol) and methyl (triphenylphosphoranylidene)acetate (10.0 g, 30.0 mmol) in benzene (100 mL) was heated at 75° C. for 48 h. The reaction was concentrated, diluted with ether, the precipitate filtered off, and the rinsate concentrated. The crude product was purified by silica gel chromatography, eluting with a gradient of 20 to 60% ethyl acetate:hexanes to give the title compound (5.25 g). MS: m/z=290.1 (M+1).

Step B. Benzyl 4-(2-methoxy-2-oxoethyl)-3,6-dihydropyridine-1(2H)-carboxylate A solution of benzyl 4-(2-methoxy-2-oxoethylidene)piperidine-1-carboxylate (5.25 g, 18.1 mol) and 1,8-diazabicyclo[5.4.0]undec-7-ene (2.71 mL, 18.1 mol) in DMF (120 mL) was stirred at room temperature. After 3 d the reaction was diluted with water and extracted with ether (4×). The organic washes were combined, dried over MgSO$_4$, filtered and concentrated under reduced pressure. The crude product was purified by silica gel chromatography, eluting with a gradient of 5 to 30% ethyl acetate:hexanes to give the title compound (2.44 g). MS: m/z=290.1 (M+1). $^1$H NMR (500 MHz, CDCl$_3$) δ 7.30-7.25 (m, 5H), 5.5 (brs, 1H), 5.2 (s, 2H), 4.0 (brs, 2H), 3.7 (s, 3H), 3.6 (brs, 21), 3.0 (s, 2H), 2.2 (brs, 2H).

Step C. Benzyl 4-{2-[(3-bromopyridin-2-yl)amino]-2-oxoethyl}-3,6-dihydropyridine-1(2H)-carboxylate Timethylaluminum (2.0 M, 2.05 mL, 4.10 mol) was added slowly to a 0° C. solution of benzyl 4-(2-methoxy-2-oxoethyl)-3,6-dihydropyridine-1(2H)-carboxylate (0.79 g, 2.73 mol) and 2-amino-3-bromopyridine (0.520 g, 3.00 mmol) in 1,2-dichloroethane (15 mL). After 30 min, the reaction was heated to 55° C. for 48 h. The reaction was quenched by the careful addition of saturated aqueous sodium bicarbonate and the mixture extracted with dichlormethane (4×). The combined organic layers were washed with 1N sodium potassium tartrate, brine, dried over MgSO$_4$, filtered, and concentrated. The crude product was purified by silica gel chromatography, eluting with a gradient of 50 to 100% ethyl acetate:hexanes to give the title compound (2.44 g). MS: m/z=430.0 (M+1).

Step D. Benzyl 4-[2-((3-bromopyridin-2-yl){[2-(trimethylsilyl)ethoxy]methyl}amino)-2-oxoethyl]-3,6-dihydropyridine-1(2H)-carboxylate Sodium hydride (60% dispersion in mineral oil; 117 mg, 4.88 mol) was added in portions over 10 min to a solution of benzyl 4-{2-[(3-bromopyridin-2-yl)amino]-2-oxoethyl}-3,6-dihydropyridine-1(2H)-carboxylate (1.91 g, 4.43 mol) in THF (15 mL) at 0° C. After 0.5 h, 2-trimethylsilyl)ethoxymethyl chloride (0.861 mL, 4.88 mol) was then added slowly, keeping the temperature of the reaction mixture below 10° C. After 4 h, sodium hydride (60 mg) and 2-(trimethylsilyl)ethoxymethyl chloride (0.45 ml) were added and the reaction allowed to warm to room temperature overnight. The reaction was quenched with saturated aqueous ammonium chloride and the mixture was extracted with CH$_2$Cl$_2$ (3×). The combined organic layers were dried over MgSO$_4$, filtered, and concentrated. The crude product was purified by silica gel chromatography, eluting with a gradient of 40 to 70% ethyl acetate: hexanes to give the title compound (1.51 g). MS: m/z=560.2 (M+1).

Step E. Benzyl 2-oxo-1-{[2-(trimethylsilyl)ethoxy]methyl}-2,2',3,3'-tetrahydro-1H,1'H-spiro[1,8-naphthyridine-4,4'-pyridine]-1'-carboxylate To a mixture of N-methyldicyclohexyl amine (0.042 mg, 0.20 mmol) and benzyl 4-[2-((3-bromopyridin-2-yl){([2-(trimethylsilyl)ethoxy]methyl}amino)-2-oxoethyl]-3,6-dihydropyridine-1(2H)-carboxylate (100 mg, 0.178 mmol) in dioxane (2 mL) was added bis(tri-tert-butylphosphine) palladium(0) (9 mg, 0.018 mmol). After 5 min, the reaction was heated to 50° C. After 90 min, bis(tri-tert-butylphosphine) palladium(0) (9 mg) was added. After an additional 30 min at 50° C., the reaction mixture was diluted with water and extracted with ether (3×). The combined organic layers were dried over MgSO$_4$, filtered, and concentrated. The crude product was purified by silica gel chromatography, eluting with a gradient of 5 to 60% ethyl acetate:hexanes to give the title compound (68 mg). MS: m/z=480.2 (M+1).

Step F. 1H-Spiro[1,8-naphthyridine-4,4'-piperidin]-2(3H)-one

To a mixture of benzyl 2-oxo-1-{[2-(trimethylsilyl)ethoxy]methyl}-2,2',3,3'-tetrahydro-1H,1'H-spiro[1,8-naphthyridine-4,4'-pyridine]-1'-carboxylate (384 mg, 0.800 mmol) in dichloromethane (10 mL) was added trifluoroacetic acid (10 mL). After 3 h, the reaction was concentrated, diluted with dichloromethane (10 mL) and ethylenediamine (720 mg, 12.0 mmol) was added. After 18 h, the reaction was concentrated, the residue partitioned between saturated aqueous NaHCO$_3$ and dichloromethane, and the layers separated. The aqueous phase was extracted with further portions of dichloromethane (2×), the organic layers combined, dried, and concentrated. 10% Palladium on carbon (300 mg) was added to a solution of this material in EtOH (10 mL). The reaction vessel was evacuated and back-filled with nitrogen (3×), then back-filled with hydrogen (1 atm). After 24 h, the mixture was filtered though celite and concentrated to give the title compound (130 mg). MS 218.1 (M+1). $^1$H NMR (500 Mz, CD$_3$OD) δ 8.14 (dd, J=1.6, 5.0 Hz, 1H), 7.80 (dd, J=1.6, 7.7 Hz, 1H), 7.10 (dd, J=5.0, 7.7 Hz, 1H), 2.98-2.95 (m, 4H), 2.78 (s, 2H), 1.96-1.90 (m, 2H), 1.69 (brd, J=11.5 Hz, 2H).

Example 1

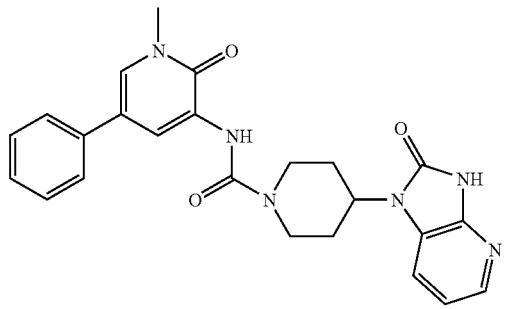

N-(1-Methyl-2-oxo-5-phenyl-1,2-dihydropyridin-3-yl)-4-(2-oxo-2,3-dihydro-1H-imidazo[4,5-b]pyridin-1-yl)piperidine-1-carboxamide Step A. 5-Bromo-1-methyl-3-nitropyridin-2(1H)-one Cesium carbonate (44.6 g, 137 mmol) was added to a solution of 5-bromo-2-hydroxy-3-nitropyridine (20.0 g, 91.3 mmol) and iodomethane (19.4 g, 137 mmol) in N,N-dimethylformamide (500 mL). After 18 h, the reaction mixture was quenched with water. The mixture was extracted with ethyl acetate (3×), and the combined organic extracts were washed with water, saturated brine, dried over sodium sulfate, filtered and concentrated. MS 233.1 (MI).

Step B3.
3-Amino-5-bromo-1-methylpyridin-2(1H)-one

Tin(II)chloride dihydrate (53.3 g, 236 mmol) was added to a solution of 5-bromo-1-methyl-3-nitropyridin-2(1R)-one (11.0 g, 47.2 mmol) in ethyl acetate (400 mL) at 80° C. After 1.5 h, the reaction mixture was quenched with saturated sodium bicarbonate. The mixture was extracted with ethyl acetate (3×), and the combined organic extracts were washed with water, saturated brine, dried over sodium sulfate, filtered and concentrated. MS 203.1 (M).

Step C. N-(5-Bromo-1-methyl-2-oxo-1,2-dihydropyridin-3-yl)-4-(2-oxo-2,3-dihydro-1H-imidazo[4-5-b]pyridin-1-yl)piperidine-1-carboxamide Triethylamine (21 µL, 0.15 mmol) was added to a solution of 3-amino-5-bromo-1-methylpyridin-2(1H)-one (30.0 mg, 0.15 mmol) and phosgene (20% wt. in toluene; 16.0 µL, 0.15 mmol) in tetrahydrofuran (1 mL) at 0° C. After 1 h, 1-piperidin-4-yl-1,3-dihydro-2H-imidazo[4,5-b]pyridin-2-one (32 mg, 0.15 mmol) and triethylamine (62 µL, 0.44 mmol) were sequentially added. The reaction mixture was allowed to warm to ambient temperature. After 18 h, the reaction mixture was filtered and concentrated. Purification by reverse phase HPLC(C-18, 95% water/acetonitrile. 5% water/acetonitrile with 0.1% trifluoroacetic acid) gave the title compound (26 mg). MS 447.1 (M).

Step D. N-(1-Methyl-2-oxo-5-phenyl-1,2-dihydropyridin-3-yl)-4-(2-oxo-2,3-dihydro-1H-imidazo[4,5-b]pyridin-1-yl)piperidine-1-carboxamide Diisopropylamine (0.15 mL, 1.07 mmol) was added to a solution of N-(5-bromo-1-methyl-2-oxo-1,2-dihydropyridin-3-yl)-4-(2-oxo-2,3-dihydro-1H-imidazo[4,5-b]pyridin-1-yl)piperidine-1-carboxamide (120 mg, 0.27 mmol), palladium acetate (18 mg, 0.08 mmol), 3,3',3'-phosphinidynetris (benzenesulfonic acid), trisodium salt (137 mg, 0.24 mmol) and phenyl boronic acid (65.0 mg, 0.54 mmol) in N,N-dimethylformamide (0.6 mL) and water (0.2 mL). The reaction mixture was heated to 80° C. After 18 h, the reaction mixture was filtered. Purification by reverse phase HPLC (C-18, 95% water/acetonitrile. 5% water/acetonitrile with 0.1% trifluoroacetic acid) gave the title compound as a trifluoroacetate salt (52 mg). MS 445.1 (M+1). $^1$H NMR (500 MHz, CDCl$_3$) δ 8.55 (d, J=2.4 Hz, 1H), 8.06 (s, 1H), 8.02 (d, J=5.1 Hz, 1H), 7.50 (d, J=7.3 Hz, 2H), 7.41 (t, J=7.6 Hz, 2H), 7.32 (d, J=8.3 Hz, 2H), 7.17 (d, J=2.2 Hz, 1H), 6.98 (dd, J=7.8, 5.1 Hz, 1H), 4.60-4.57 (m, 1H), 4.38 (d, J=14.2 Hz, 2H), 3.70 (s, 3H), 3.09 (t, J=12.2 Hz, 21), 2.31-2.36 (m, 21), 1.98 (d, J=10.0 Hz, 211).

Essentially following the procedures outlined for the preparation of Example 1, the Examples in Table 1 were prepared.

TABLE 1

| Examples | R$^1$ | R$^2$ | R$^3$ | MS (M + 1) |
|---|---|---|---|---|
| 2 | CH$_3$ | 3-cyanophenyl | 1H-imidazo[4,5-b]pyridin-3(2H)-on-1-yl | 470.1931 |
| 3 | CH$_3$ | 2-hydroxyphenyl | 1H-imidazo[4,5-b]pyridin-3(2H)-on-1-yl | 461.1934 |

TABLE 1-continued

| Examples | R¹ | R² | R³ | MS (M + 1) |
|---|---|---|---|---|
| 4 | CH₃ | 4-hydroxyphenyl | 1H-imidazo[4,5-b]pyridin-1-yl | 461.1917 |
| 5 | CH₃ | pyridin-3-yl | 1H-imidazo[4,5-b]pyridin-1-yl | 446.1921 |
| 6 | CH₃ | 1H-pyrazol-3-yl | 1H-imidazo[4,5-b]pyridin-1-yl | 435.1882 |
| 7 | CH₃ | 4-carboxyphenyl | 1H-imidazo[4,5-b]pyridin-1-yl | 489.1858 |
| 8 | CH₃ | 4-cyanophenyl | 1H-imidazo[4,5-b]pyridin-1-yl | 470.1921 |
| 9 | CH₃ | 4-(methoxycarbonyl)phenyl | 1H-imidazo[4,5-b]pyridin-1-yl | 503.2037 |

TABLE 1-continued
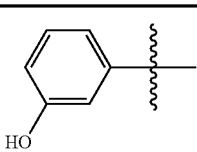
| Examples | R¹ | R² | R³ | MS (M + 1) |
|---|---|---|---|---|
| 10 | CH₃ | 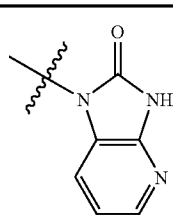 | 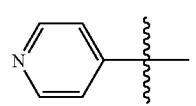 | 461.1918 |
| 11 | CH₃ | 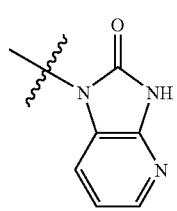 | 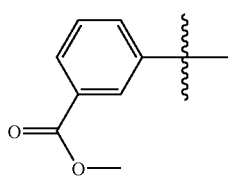 | 446.1923 |
| 12 | CH₃ | 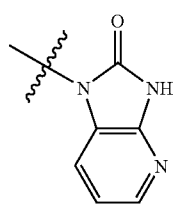 | 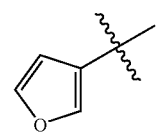 | 503.2044 |
| 13 | CH₃ | 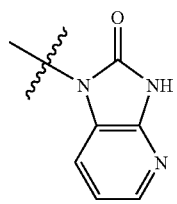 | 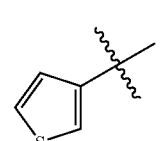 | 435.1772 |
| 14 | CH₃ | 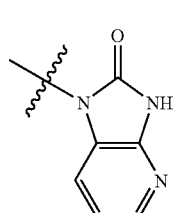 | 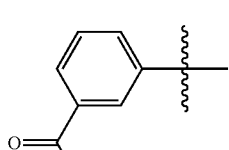 | 451.1541 |
| 15 | CH₃ | 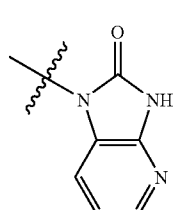 | | 489.1875 |

TABLE 1-continued

| Examples | R¹ | R² | R³ | MS (M + 1) |
|---|---|---|---|---|
| 16 | CH₃ | 2-pyrrolyl | 1H-imidazo[4,5-b]pyridin-1-yl | 434.1926 |
| 17 | CH₃ | 4-(methylsulfonyl)phenyl | 1H-imidazo[4,5-b]pyridin-1-yl | 523.1750 |
| 18 | CH₃ | benzo[b]thiophen-3-yl | 1H-imidazo[4,5-b]pyridin-1-yl | 501.1 |
| 19 | CH₃ | 4-methoxyphenyl | 1H-imidazo[4,5-b]pyridin-1-yl | 475.2056 |
| 20 | CH₃ | 1H-imidazol-4-yl | 1H-imidazo[4,5-b]pyridin-1-yl | 435.1860 |
| 21 | CH₃ | pyridin-2-yl | 1H-imidazo[4,5-b]pyridin-1-yl | 446.1914 |

TABLE 1-continued

| Examples | R¹ | R² | R³ | MS (M + 1) |
|---|---|---|---|---|
| 22 | CH₃ | pyrimidin-2-yl | 1H-imidazo[4,5-b]pyridin-1-yl (C=O) | 447.1 |
| 23 | CH₃ | pyrazin-2-yl | 1H-imidazo[4,5-b]pyridin-1-yl (C=O) | 447.1840 |
| 24 | CH₃OCH₂CH₂− | phenyl | 1H-imidazo[4,5-b]pyridin-1-yl (C=O) | 489.4 |
| 25 | CH₃OCH₂CH₂− | 2-fluorophenyl | 1H-imidazo[4,5-b]pyridin-1-yl (C=O) | 507.2113 |
| 26 | CH₃OCH₂CH₂− | 3-fluorophenyl | 1H-imidazo[4,5-b]pyridin-1-yl (C=O) | 507.2120 |
| 27 | CH₃OCH₂CH₂− | 5-fluoropyridin-2-yl | 1H-imidazo[4,5-b]pyridin-1-yl (C=O) | 507.2119 |

TABLE 1-continued

| Examples | R¹ | R² | R³ | MS (M + 1) |
|---|---|---|---|---|
| 28 | methoxyethyl | 4-hydroxyphenyl | imidazo[4,5-b]pyridin-1-yl | 505.2187 |
| 29 | methoxyethyl | thiophen-3-yl | imidazo[4,5-b]pyridin-1-yl | 495.1793 |
| 30 | methoxyethyl | pyridin-3-yl | imidazo[4,5-b]pyridin-1-yl | 490.2178 |
| 31 | methoxyethyl | pyridin-4-yl | imidazo[4,5-b]pyridin-1-yl | 490.2189 |
| 32 | methoxyethyl | 1H-pyrazol-3-yl | imidazo[4,5-b]pyridin-1-yl | 479.2122 |
| 33 | methoxyethyl | 2,3-difluorophenyl | imidazo[4,5-b]pyridin-1-yl | 525.2034 |

TABLE 1-continued

| Examples | R¹ | R² | R³ | MS (M + 1) |
|---|---|---|---|---|
| 34 | MeO-CH₂CH₂-C(CH₃)(wavy)- | 2,3-dimethoxyphenyl | 1H-imidazo[4,5-b]pyridin-1-yl (2-oxo) | 549.2471 |
| 35 | HO-CH₂CH₂-C(CH₃)(wavy)- | phenyl | 1H-imidazo[4,5-b]pyridin-1-yl (2-oxo) | 475.2 |
| 36 | HOOC-CH₂-C(CH₃)(wavy)- | phenyl | 1H-imidazo[4,5-b]pyridin-1-yl (2-oxo) | 489.2 |
| 37 | MeOOC-CH₂-C(CH₃)(wavy)- | phenyl | 1H-imidazo[4,5-b]pyridin-1-yl (2-oxo) | 503.4 |
| 38 | cyclopropyl-CH₂-C(CH₃)(wavy)- | phenyl | 1H-imidazo[4,5-b]pyridin-1-yl (2-oxo) | 485.2 |
| 39 | F₃C-CH₂-C(CH₃)(wavy)- | phenyl | 1H-imidazo[4,5-b]pyridin-1-yl (2-oxo) | 513.2 |

TABLE 1-continued
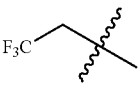
| Examples | R¹ | R² | R³ | MS (M + 1) |
|---|---|---|---|---|
| 40 | 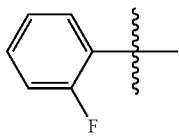 | 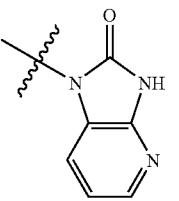 |  | 531.1750 |
| 41 | 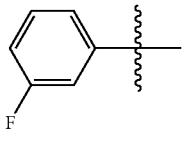 | 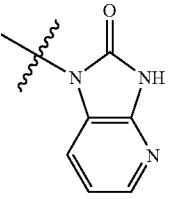 |  | 531.1790 |
| 42 | 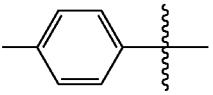 | 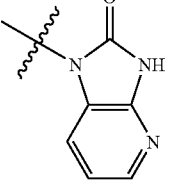 | 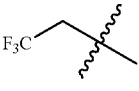 | 531.1773 |
| 43 | 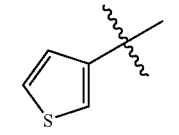 | 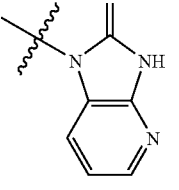 | 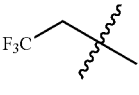 | 519.1400 |
| 44 | 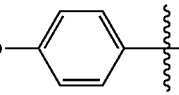 | 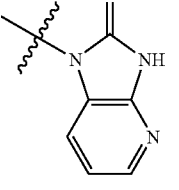 | 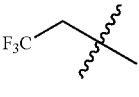 | 529.1814 |
| 45 | 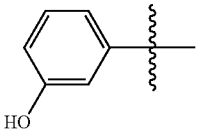 | 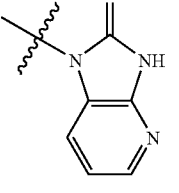 | | 529.1792 |

TABLE 1-continued

| Examples | R¹ | R² | R³ | MS (M + 1) |
|---|---|---|---|---|
| 46 | F₃C-CH₂-C(CH₃)₂- | 3-pyridyl | 3H-imidazo[4,5-b]pyridin-1-yl | 514.1794 |
| 47 | F₃C-CH₂-C(CH₃)₂- | 4-pyridyl | 3H-imidazo[4,5-b]pyridin-1-yl | 514.1809 |
| 48 | F₃C-CH₂-C(CH₃)₂- | 1H-pyrazol-3-yl | 3H-imidazo[4,5-b]pyridin-1-yl | 503.2 |
| 49 | F₃C-CH₂-C(CH₃)₂- | 2,3-difluorophenyl | 3H-imidazo[4,5-b]pyridin-1-yl | 549.1652 |
| 50 | F₃C-CH₂-C(CH₃)₂- | 1-methyl-1H-pyrazol-3-yl | 3H-imidazo[4,5-b]pyridin-1-yl | 517.1931 |
| 51 | F₃C-CH₂-C(CH₃)₂- | 1-methyl-1H-pyrazol-5-yl | 3H-imidazo[4,5-b]pyridin-1-yl | 517.1927 |

TABLE 1-continued

| Examples | R¹ | R² | R³ | MS (M + 1) |
|---|---|---|---|---|
| 52 | F₃C-C(CH₃)- | 2-(morpholine-4-carbonyl)phenyl | 3H-imidazo[4,5-b]pyridin-2(1H)-on-1-yl | 626.2340 |
| 53 | F₃C-C(CH₃)- | 2-phenylethyl-C(CH₃)- | 3H-imidazo[4,5-b]pyridin-2(1H)-on-1-yl | 541.2182 |
| 54 | MeO-(CH₂)₃-C(CH₃)- | phenyl | 3H-imidazo[4,5-b]pyridin-2(1H)-on-1-yl | 503.5 |
| 55 | iPrO-CH₂CH₂-C(CH₃)- | phenyl | 3H-imidazo[4,5-b]pyridin-2(1H)-on-1-yl | 517.2526 |
| 56 | phenyl-C(CH₃)- | phenyl | 3H-imidazo[4,5-b]pyridin-2(1H)-on-1-yl | 507 |
| 57 | 2-pyridyl-CH₂CH₂-C(CH₃)- | phenyl | 3H-imidazo[4,5-b]pyridin-2(1H)-on-1-yl | 536.2359 |

TABLE 1-continued
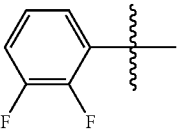
| Examples | R¹ | R² | R³ | MS (M + 1) |
|---|---|---|---|---|
| 58 | H | 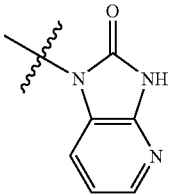 |  | 467 |
| 59 | 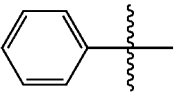 | 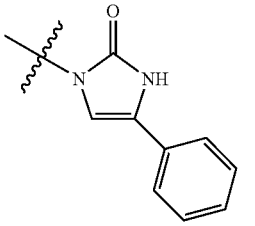 | 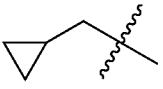 | 510.2 |
| 60 | 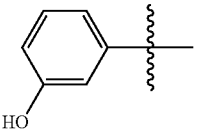 | 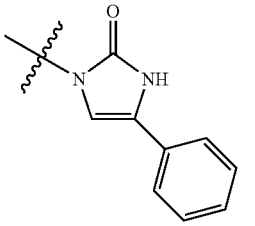 | 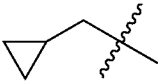 | 526.22 |
| 61 | 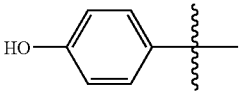 | 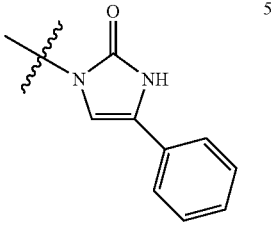 | 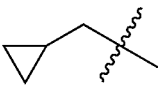 | 526.2439 |
| 62 | 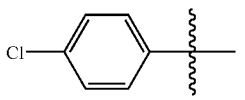 | 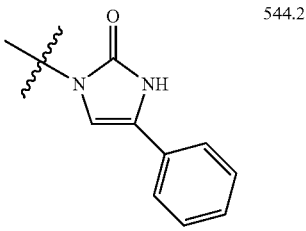 | | 544.2 |

TABLE 1-continued
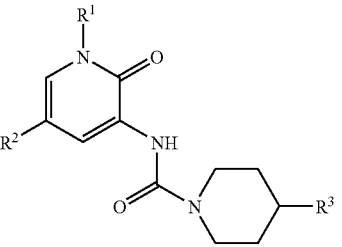
| Examples | R¹ | R² | R³ | MS (M + 1) |
|---|---|---|---|---|
| 63 | 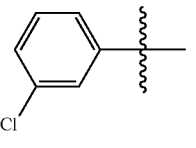 | 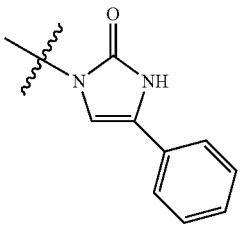 | 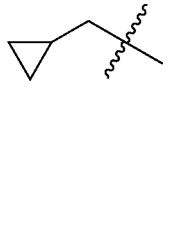 | 544.2 |
| 64 | 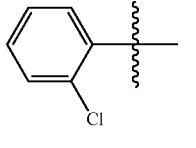 | 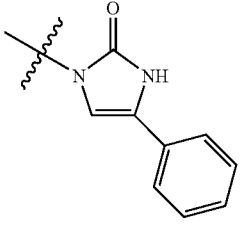 | 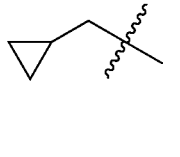 | 544.2 |
| 65 | 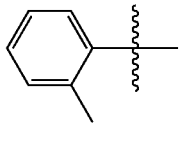 | 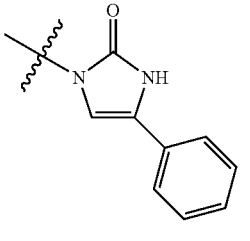 | 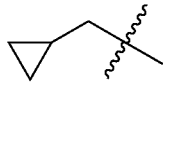 | 524.2 |
| 66 | 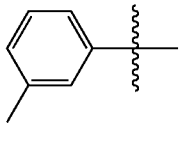 | 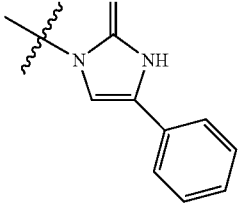 | 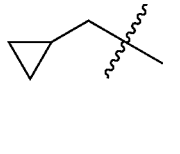 | 524.3 |
| 67 | 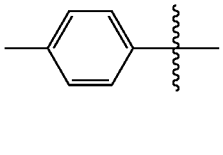 | 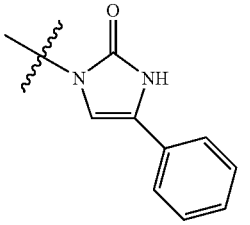 | | 524.3 |

TABLE 1-continued

| Examples | R¹ | R² | R³ | MS (M + 1) |
|---|---|---|---|---|
| 68 | cyclopropylmethyl-C(CH₃)- | pyridin-4-yl-C(CH₃)- | 4-phenyl-imidazol-2(3H)-one-1-yl | 511.2 |
| 69 | cyclopropylmethyl-C(CH₃)- | pyridin-3-yl-C(CH₃)- | 4-phenyl-imidazol-2(3H)-one-1-yl | 511.2 |
| 70 | benzyl-C(CH₃)- | phenyl-C(CH₃)- | 4-phenyl-imidazol-2(3H)-one-1-yl | 546.2511 |
| 71 | CH₃ | phenyl-C(CH₃)- | 4-phenyl-imidazol-2(3H)-one-1-yl | 470.2 |

TABLE 1-continued

| Examples | R¹ | R² | R³ | MS (M + 1) |
|---|---|---|---|---|
| 72 | tert-butyl ester group | H | N-phenyl imidazolone | 494.2 |
| 73 | CH₃ | phenyl | N-phenyl triazolone | 471.2150 |
| 74 | CH₃ | 3-cyanophenyl | N-phenyl triazolone | 496.2088 |
| 75 | CH₃ | 4-cyanophenyl | N-phenyl triazolone | 496.2090 |
| 76 | CH₃ | 4-pyridyl | N-phenyl triazolone | 472.2083 |

TABLE 1-continued
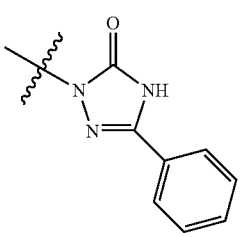
| Examples | R¹ | R² | R³ | MS (M + 1) |
|---|---|---|---|---|
| 77 | CH₃ | H | 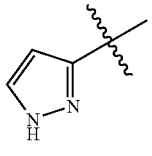 | 395.1823 |
| 78 | CH₃ | 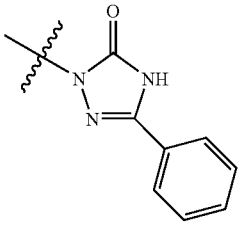 | 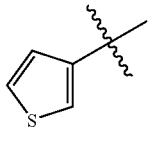 | 461.2046 |
| 79 | CH₃ | 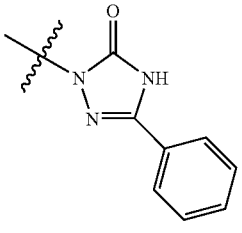 | 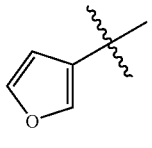 | 477.1694 |
| 80 | CH₃ | 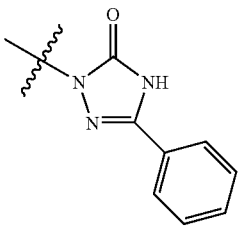 | 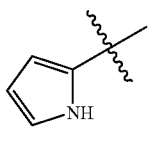 | 461.1926 |
| 81 | CH₃ | 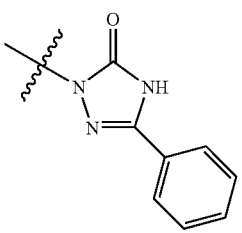 | | 460.2099 |

TABLE 1-continued

| Examples | R¹ | R² | R³ | MS (M + 1) |
|---|---|---|---|---|
| 82 | CH₃ | pyridin-3-yl (1-methylethyl linker) | 2-(5-oxo-3-phenyl-4,5-dihydro-1H-1,2,4-triazol-1-yl) | 472.2082 |
| 83 | CH₃ | pyrimidin-5-yl (1-methylethyl linker) | 2-(5-oxo-3-phenyl-4,5-dihydro-1H-1,2,4-triazol-1-yl) | 473.2036 |
| 84 | CH₃ | 4-hydroxyphenyl (1-methylethyl linker) | 2-(5-oxo-3-phenyl-4,5-dihydro-1H-1,2,4-triazol-1-yl) | 487.2084 |
| 85 | CH₃ | 3-hydroxypyridin-5-yl (1-methylethyl linker) | 2-(5-oxo-3-phenyl-4,5-dihydro-1H-1,2,4-triazol-1-yl) | 487.2082 |
| 86 | CH₃ | 2-hydroxyphenyl (1-methylethyl linker) | 2-(5-oxo-3-phenyl-4,5-dihydro-1H-1,2,4-triazol-1-yl) | 487.2073 |

TABLE 1-continued

| Examples | R¹ | R² | R³ | MS (M + 1) |
|---|---|---|---|---|
| 87 | CH₃ | 3-(methoxycarbonyl)phenyl | 3-oxo-5-phenyl-2,3-dihydro-1H-1,2,4-triazol-1-yl | 529.2173 |
| 88 | CH₃ | 3-carboxyphenyl | 3-oxo-5-phenyl-2,3-dihydro-1H-1,2,4-triazol-1-yl | 515.1 |
| 89 | CH₃ | 4-(methoxycarbonyl)phenyl | 3-oxo-5-phenyl-2,3-dihydro-1H-1,2,4-triazol-1-yl | 529.2188 |

Example 90

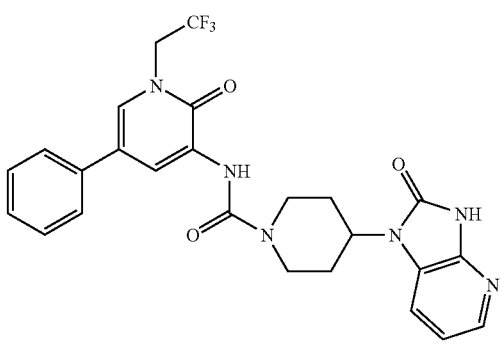

1-(1-{[2-Oxo-5-phenyl-1-(2,2,2-trifluoroethyl)-1,2-dihydropyridin-3-yl]acetyl}piperidin-4-yl)-1,3-dihydro-2H-imidazo[4,5-b]pyridin-2-one

Step A.
3-Methyl-1-(2,2,2-trifluoroethyl)pyridin-2(1H)-one

Cesium carbonate (11.4 g, 34.9 mmol) was added to a solution of 3-methylpyridin-2(1H)-one (3.81 g, 34.9 mmol) and 2,2,2-trifluoroethyl trichloromethanesulfonate (9.81 g, 34.9 mmol) in dichloromethane (80 mL). After 2 h, water was added. The mixture was extracted with ether (3×), and the combined organic extracts were dried over sodium sulfate, filtered and concentrated. Purification by silica gel chromatography (100% dichloromethane 25%→methanol/dichloromethane) gave the title compound (3.73 g). MS192.3 (M+1).

Step B. 5-Bromo-3-(bromomethyl)-1-(2,2,2-trifluoroethyl)pyridin-2(1H)-one

N-Bromosuccinimide (2.89 g, 16.2 mmol) was added to a solution of 3-methyl-1-(2,2,2-trifluoroethyl)pyridin-2(1H)-one (2.82 g, 14.8 mmol) in 1,2-dichloroethane (60 mL) and this mixture was heated to 85° C. in the dark (covered with Al foil). After 2 h, the reaction was removed from the dark and N-bromosuccinimide (2.89 g, 16.2 mmol) and AIBN (24 mg) were added. After 24 h at 85° C., the reaction was diluted with saturated aqueous NaHCO₃, extracted with dichloromethane (3×), and the combined organic extracts were dried over sodium sulfate, filtered and concentrated. Purification by silica gel chromatography (100% dichloromethane→5% methanol/dichloromethane) gave the title compound (2.89 g). MS 349.9 (M+1).

Step C. [5-Bromo-2-oxo-1-(2,2,2-trifluoroethyl)-1,2-dihydropyridin-3-yl]acetonitrile 5-Bromo-3-(bromomethyl)-1-(2,2,2-trifluoroethyl)pyridin-2(1H)-one (1.40 g, 4.01 mmol) was added in portions over 15 min to a solution of sodium cyanide (1.48 g, 30.1 mmol) in methanol (15 mL). After 1 h, the reaction was concentrated to dryness, diluted with water, extracted with dichloromethane (3×), and the combined organic extracts were dried over sodium sulfate, filtered and concentrated. Purification by silica gel chromatography (100% dichloromethane >5% methanol/dichloromethane) gave the title compound (0.740 g). MS 296.9 (M+1).

Step D. [5-Bromo-2-oxo-1-(2,2,2-trifluoroethyl)-1,2-dihydropyridin-3-yl]acetic acid

[5-Bromo-2-oxo-1-(2,2,2-trifluoroethyl)-1,2-dihydropyridin-3-yl]acetonitrile (223 mg, 0.756 mmol) was diluted with 6N HCl (10 mL) and heated to 85° C. After 24 h, the reaction was extracted with ethyl acetate (5×), and the combined organic extracts were dried over sodium sulfate, filtered and concentrated to give the title compound (0.231 g). MS 316.0 (M+1).

Step E. 1-(1-{[5-Bromo-2-oxo-1-(2,2,2-trifluoroethyl)-1,2-dihydropyridin-3-yl]acetyl}piperidin-4-yl)-1,3-dihydro-2H-imidazo[4,5-b]pyridin-2-One Triethylamine (410 µL, 2.94 mmol) was added to a solution of [5-bromo-2-oxo-1-(2,2,2-trifluoroethyl)-1,2-dihydropyridin-3-yl]acetic acid (231 mg, 0.736 mmol), 2-oxo-1-(4-piperidinyl)-2,3-dihydro-1H-imidazo[4,5-b]pyridine dihydrochloride (236 mg, 0.809 mmol), EDC (212 mg, 1.10 mmol), and HOAt (100 mg, 0.736 mmol) in DMF (13 mL). After 24 h, saturated aqueous sodium bicarbonate was added and the mixture was extracted with ethyl acetate (3×). The organic layers were dried over sodium sulfate, filtered and concentrated. Purification by silica gel chromatography [100% dichloromethane→90% dichloromethane/methanol] gave the title compound (0.192 g). MS 516.0 (M+1).

Step F. 1-(1-{[2-Oxo-5-phenyl-1-(2,2,2-trifluoroethyl)-1,2-dihydropyridin-3-yl]acetyl}piperidin-4-yl)-1,3-dihydro-2H-imidazo[4,5-b]pyridin-2-one 1,1'-Bis(diphenylphospino)ferrocene palladium(II)dichloride dichloromethane complex (5 mg, 0.006 mmol) was added to a solution of 1-(1-{[5-bromo-2-oxo-1-(2,2,2-trifluoroethyl)-1,2-dihydropyridin-3-yl]acetyl}piperidin-4-yl)-1,3-dihydro-2H-imidazo[4,5-b]pyridin-2-one (50 mg, 0.097 mmol), phenyl boronic acid (14 mg, 0.117 mmol), and potassium phosphate (45 mg, 0.214 mmol), in DME (2 mL) and heated to 85° C. After 24 h, water was added and the mixture was extracted with ethyl acetate (3×). The organic layers were dried over sodium sulfate, filtered and concentrated. Purification by silica gel chromatography [99%-85% dichloromethane/methanol] gave the title compound (25 mg). MS 512.1861 (M+1).

Essentially following the procedures outlined for the preparation of Example 90, the Examples in Table 2 were prepared.

TABLE 2

| Examples | $R^1$ | $R^2$ | MS (M + 1) |
|---|---|---|---|
| 91 | $F_3C$-CH₂- | 2,3-difluorophenyl | 548.1714 |
| 92 | $F_3C$-CH₂- | 2,3,4-trifluorophenyl | 566.1634 |
| 93 | $F_3C$-CH₂- | Br | 514.0689 (M) |
| 94 | $F_3C$-CH₂- | 2,3-dimethoxyphenyl | 572.2143 |
| 95 | $F_3C$-CH₂- | 2-cyanophenyl | 537.1884 |
| 96 | $F_3C$-CH₂- | 6-methoxypyridin-3-yl | 543.1966 |
| 97 | $F_3C$-CH₂- | 4-hydroxy-3,5-dimethylphenyl | 556.2159 |

TABLE 2-continued

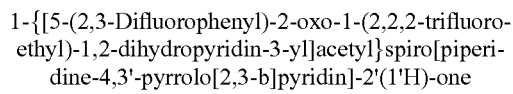

| Examples | R¹ | R² | MS (M + 1) |
|---|---|---|---|
| 98 | F₃C-CH₂- | 2-phenylphenyl | 588.2218 |
| 99 | F₃C-CH₂- | 2-bromophenyl | 590.0986 (M) |
| 100 | F₃C-CH₂- | H | 436.1571 |
| 101 | MeO-CH₂CH₂- | phenyl | 488.2329 |
| 102 | MeO-CH₂CH₂- | 2,3-difluorophenyl | 524.2073 |

Example 103

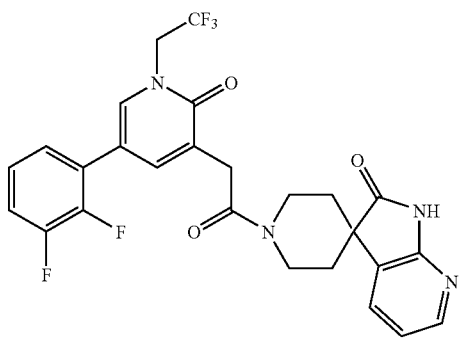

1-{[5-(2,3-Difluorophenyl)-2-oxo-1-(2,2,2-trifluoroethyl)-1,2-dihydropyridin-3-yl]acetyl}spiro[piperidine-4,3'-pyrrolo[2,3-b]pyridin]-2'(1'H)-one Prepared essentially following the procedure outlined for the preparation of Example 90.

MS 533.1586 (M+1).

Example 104

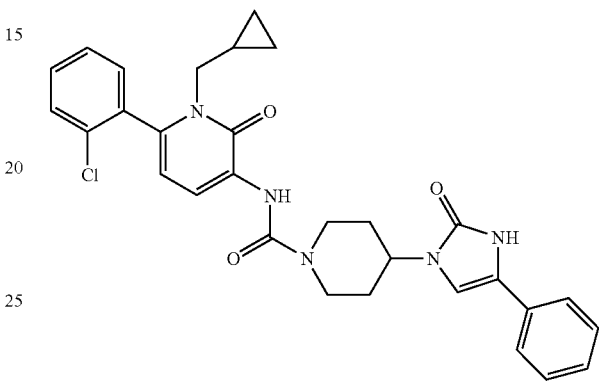

N-[6-(2-Chlorophenyl)-1-(cyclopropylmethyl)-2-oxo-1,2-dihydropyridin-3-yl]-4-(2-oxo-4-phenyl-2,3-dihydro-1H-imidazol-1-yl)piperidine-1-carboxamide Step A: Benzyl 6-(2-chlorophenyl)-1-(cyclopropylmethyl)-2-oxo-1,2-dihydropyridin-3-ylcarbamate Cesium carbonate (1.07 g, 3.30 mmol) was added to a solution of benzyl 6-(2-chlorophenyl)-2-oxo-1,2-dihydropyridin-3-ylcarbamate (*J. Med. Chem.* 1994, 37, 3303-3312) (585 mg, 1.65 mmol) and cyclopropylmethyl bromide (0.19 mL, 1.98 mmol) in N,N-dimethylformamide (5 mL). After 4 h, water was added, and the mixture was extracted with ethyl acetate. The organic layer was washed with water (2×), saturated brine, dried over magnesium sulfate, filtered and concentrated. Purification by silica gel chromatography (hexanes→30% ethyl acetate/hexanes) gave the title compound (258 mg). MS 409.0 (M+1).

Step B: 3-Amino-6-(2-chlorophenyl-)-1-(cyclopropylmethyl)pyridin-2(1H)-one

10% Palladium on carbon (80 mg) was added to a solution of benzyl 6-(2-chlorophenyl)-1-cyclopropylmethyl)-2-oxo-1,2-dihydropyridin-3-ylcarbamate (280 mg, 0.69 mmol) in ethanol (40 mL). The reaction vessel was evacuated and back-filled with nitrogen (3×), then back-filled with hydrogen (50 psi). After 5 h, the mixture was filtered and concentrated to give the title compound (17 mg). MS 274.9 (M+1).

Step C: N-[6-(2-Chlorophenyl)-1-(cyclopropylmethyl)-2-oxo-1,2-dihydropyridin-3-yl]-4-(2-oxo-4-phenyl-2,3-dihydro-1H-imidazol-1-yl)piperidine-1-carboxamide Triethylamine (9 μL, 0.062 mmol) was added to a solution of amino-6-(2-chlorophenyl)-1-(cyclopropylmethyl)pyridin-2(1H)one (17 mg, 0.062 mmol) and 4-nitrophenyl chloroformate (13 mg, 0.062 mmol) in tetrahydrofuran (2 mL) at 0° C. After 0.5 h, 4-(2-oxo-4-phenyl-2,3-dihydro-1H-imidazol-1-yl)piperidinium chloride (20 mg, 0.071 mmol) and triethylamine (0.030 mL, 0.215 mmol) were added and the mixture allowed to warm to ambient temperature. After 2 h, the mixture was concentrated in vacuo. Purification by silica gel chromatography (100% dichloromethane→95% dichloromethane/methanol) followed by reverse phase HPLC(C-18, 95% water/acetonitrile→5% water/acetonitrile with 0.1% trifluoroacetic acid) gave the title compound (5 mg). MS 544.2 (M+1).

Example 105

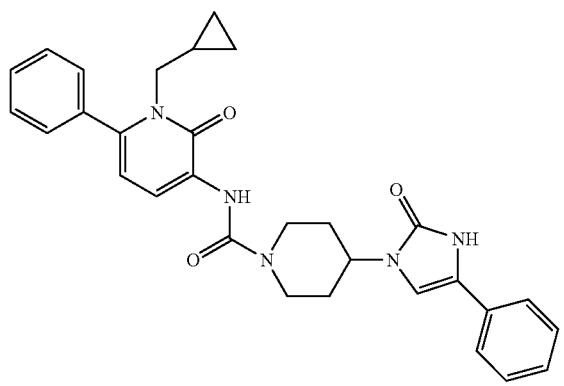

N-[1-(Cyclopropylmethyl)-2-oxo-6-phenyl-1,2-dihydropyridin-3-yl]-4-(2-oxo-4-phenyl-2,3-dihydro-1H-imidazol-1-yl)piperidine-1-carboxamide Prepared essentially following the procedure outlined for the preparation of Example 104. MS 510.2 (M+1).

Example 106

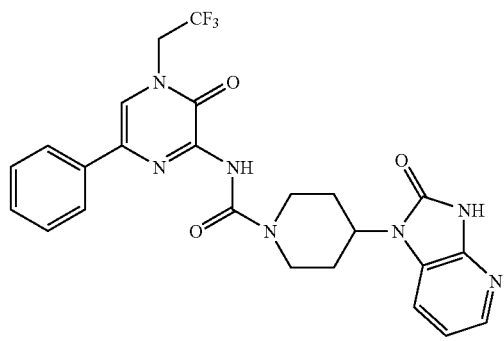

4-(2-Oxo-2,3-dihydro-1H-imidazo[4,5-b]pyridin-1-yl)-N-[3-oxo-6-phenyl-4-(2,2,2-trifluoroethyl)-3,4-dihydropyrazin-2-yl]piperidine-1-carboxamide Prepared by one skilled in the art following the route outlined in Scheme 12. MS 574.1829 (M+1).

Example 107

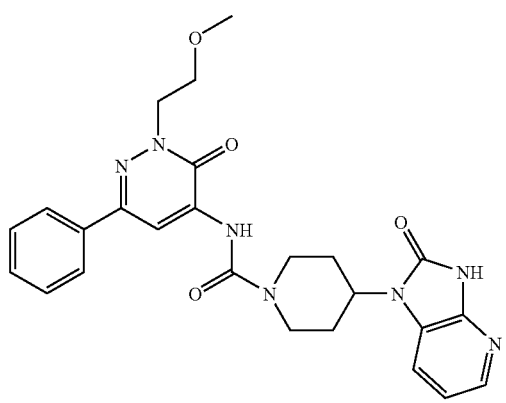

N-[2-(2-Methoxyethyl)-3-oxo-6-phenyl-2,3-dihydropyridazin-4-yl]-4-(2-oxo-2,3-dihydro-1H-imidazo[4,5-b]pyridin-1-yl)piperidine-1-carboxamide Prepared by one skilled in the art following the route outlined in Scheme 12. MS 490 (M+1).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A compound of the Formula I:

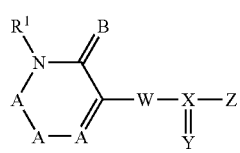

wherein:
Z is selected from:

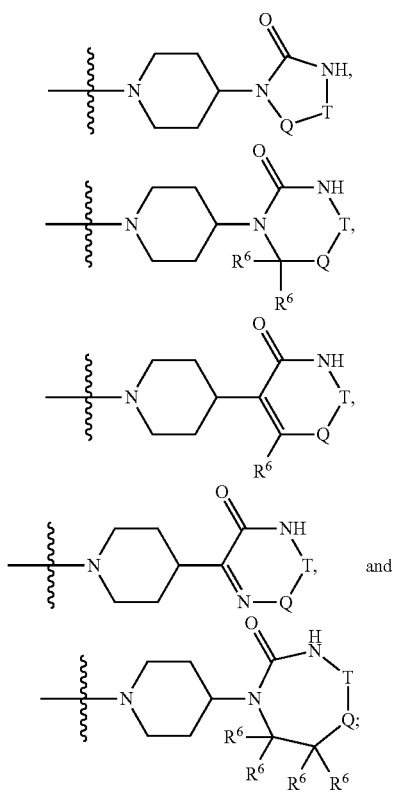

A is C(R²);
B is O or S;
R¹ is selected from:
1) H, $C_1$-$C_6$ alkyl, $C_{3-6}$ cycloalkyl and heterocycle, wherein the heterocycle is selected from azetidine, dioxane, dioxolane, morpholine, oxetane, piperazine, piperidine, pyrrolidine, tetrahydrofuran, and tetrahydropyran wherein said alkyl, cycloalkyl and heterocycle are unsubstituted or substituted with one or more substituents each independently selected from:
   a) $C_{1-6}$ alkyl,
   b) $C_{3-6}$ cycloalkyl,
   c) phenyl, unsubstituted or substituted with 1-5 substituents each independently selected from $R^4$,
   d) heteroaryl, unsubstituted or substituted with 1-5 substituents each independently selected from $R^4$, and where heteroaryl is selected from:
      imidazole, isoxazole, oxazole, pyrazine, pyrazole, pyridazine, pyridine, pyrimidine, and thiazole;
   e) heterocycle, unsubstituted or substituted with 1-5 substituents each independently selected from $R^4$, and where heterocycle is selected from: azetidine, dioxane, dioxolane, morpholine, oxetane, piperazine, piperidine, pyrrolidine, tetrahydrofuran, and tetrahydropyran;
   f) $(F)_p C_{1-3}$ alkyl,
   g) halogen,
   h) $OR^4$,
   i) $O(CH_2)_s OR^4$,
   j) $CO_2 R^4$,
   k) CN,
   l) $NR^{10} R^{11}$,
   m) $O(CO)R^4$;

2) aryl or heteroaryl, selected from: phenyl, imidazole, isoxazole, oxazole, pyrazine, pyrazole, pyridazine, pyridine, pyrimidine, and thiazole, unsubstituted or substituted with one or more substituents each independently selected from:
   a) $C_{1-6}$ alkyl,
   b) $C_{3-6}$ cycloalkyl,
   c) $(F)_p C_{1-3}$ alkyl,
   d) halogen,
   e) $OR^4$,
   f) $CO_2 R^4$,
   g) $(CO)NR^{10} R^{11}$,
   h) $SO_2 NR^{10} R^{11}$,
   i) $N(R^{10}) SO_2 R^{11}$,
   j) $S(O)_m R^4$,
   k) CN,
   l) $NR^{10} R^{11}$, and
   m) $O(CO)R^4$;

R² is selected from:
1) H, $C_1$-$C_6$ alkyl, $C_{3-6}$ cycloalkyl and heterocycle, wherein the heterocyle is selected from azetidine, imidazolidine, imidazoline, isoxazoline, isoxazolidine, morpholine, oxazoline, oxazolidine, oxetane, pyrazolidine, pyrazoline, pyrroline, tetrahydrofuran, tetrahydropyran, thiazoline, and thiazolidine: wherein said alkyl, cycloalkyl and heterocycle are unsubstituted or substituted with one or more substituents each independently selected from:
   a) $C_{1-6}$ alkyl,
   b) $C_{3-6}$ cycloalkyl,
   c) phenyl, unsubstituted or substituted with 1-5 substituents each independently selected from $R^4$,
   d) heteroaryl, unsubstituted or substituted with 1-5 substituents each independently selected from $R^4$,
      and where heteroaryl is selected from: benzimidazole, benzothiophene, furan, imidazole, indole, isoxazole, oxazole, pyrazine, pyrazole, pyridazine, pyridine, pyrimidine, pyrrole, thiazole, thiophene, and triazole;
   e) heterocycle, unsubstituted or substituted with 1-5 substituents where the substituents are independently selected from $R^4$, and where heterocycle is selected from: azetidine, imidazolidine, imidazoline, isoxazoline, isoxazolidine, morpholine, oxazoline, oxazolidine, oxetane, pyrazolidine, pyrazoline, pyrroline, tetrahydrofuran, tetrahydropyran, thiazoline, and thiazolidine;
   f) $(F)_p C_{1-3}$ alkyl,
   g) halogen,
   h) $OR^4$,
   i) $O(CH_2)_s OR^4$,
   j) $CO_2 R^4$,
   k) CN,
   l) $NR^{10} R^{11}$, and
   m) $O(CO)R^4$; and 2) aryl or heteroaryl, selected from:
   phenyl, benzimidazole, benzothiophene, furan, imidazole, indole, isoxazole, oxazole, pyrazine, pyrazole, pyridazine, pyridine, pyrimidine, pyrrole, thiazole, thiophene, and triazole, unsubstituted or substituted with one or more substituents each independently selected from:
   a) $C_{1-6}$ alkyl,
   b) $C_{3-6}$ cycloalkyl,
   c) $(F)_p C_{1-3}$ alkyl,
   d) halogen,
   e) $OR^4$, f) $CO_2R^4$,
g) $(CO)NR^{10}R^{11}$,
h) $SO_2NR^{10}R^{11}$,
i) $N(R^{10})SO_2R^{11}$,
j) $S(O)_mR^4$,
k) CN,
l) $NR^{10}R^{11}$, and
m) $O(CO)R^4$, where $R^1$ and $R^2$, or any two independent $R^2$, on adjacent atoms optionally join to form a ring selected from: $C_{5-7}$ cycloalkyl, heterocycle, aryl, and heteroaryl, in which the ring is unsubstituted or substituted with 1-10 substituents each independently selected from $R^6$;

$R^{10}$ and $R^{11}$ are independently selected from: H, $C_{1-6}$ alkyl, $(F)_pC_{1-6}$ alkyl, $C_{3-6}$ cycloalkyl, aryl, heteroaryl, and benzyl, wherein said alkyl, cycloalkyl, aryl, heteroaryl and benzyl are unsubstituted or substituted with halogen, hydroxy or $C_1$-$C_6$ alkoxy, where $R^{10}$ and $R^{11}$ optionally join to form a ring selected from: azetidinyl, pyrrolidinyl, piperidinyl, piperazinyl, or morpholinyl, which is ring is unsubstituted or substituted with 1-5 substituents each independently selected from $R^4$;

$R^4$ is independently selected from: H, $C_{1-6}$ alkyl, $(F)_pC_{1-6}$ alkyl, $C_{3-6}$ cycloalkyl, aryl, heteroaryl and benzyl, wherein said alkyl, cycloalkyl, aryl, heteroaryl and benzyl are unsubstituted or substituted with halogen, hydroxy or $C_1$-$C_6$ alkoxy;

W is O, $NR^4$ or $C(R^4)_2$;

X is C or S;

Y is $O,(R^4)_2$, NCN, $NSO_2CH_3$ or $NCONH_2$, or Y is $O_2$ when X is S;

$R^6$ is H;

Q is independently selected from:
(1) $=C(R^{7a})-$,
(2) $-C(R^{7a})_2-$,
(3) $-C(=O)-$,
(4) $-S(O)_m-$,
(5) $=N-$, and
(6) $-N(R^{7a})-$;

T is independently selected from:
(1) $=C(R^{7b})-$,
(2) $-C(R^{7b})_2-$,
(3) $-C(=O)-$,
(4) $-S(O)_m-$,
(5) $=N-$, and
(6) $-N(R^{7b})-$;

$R^{7a}$ and $R^{7b}$ are each independently selected from H and phenyl, and $R^{7a}$ and $R^{7b}$ on adjacent caron atoms and the atoms to which they are attached optionally join to form a ring selected from phenyl or pyridine, which ring is unsubstituted;

p is 0 to 2q+1, for a substituent with q carbons;

m is 0, 1 or 2;

n is 0 or 1;

s is 1, 2 or 3;

and pharmaceutically acceptable salts and individual diastereomers thereof.

2. The compound of claim 1 having the Formula Ia:

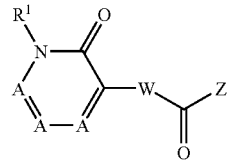

and pharmaceutically acceptable salts and individual stereoisomers thereof.

3. The compound of claim 1 having the Formula Id:

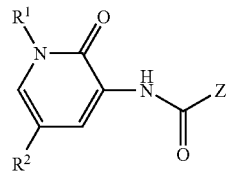

and pharmaceutically acceptable salts and individual stereoisomers thereof.

4. The compound of claim 1 having the Formula Ie:

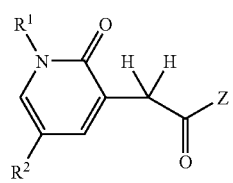

and pharmaceutically acceptable salts and individual stereoisomers thereof.

5. A compound of claim 1 of the formula:

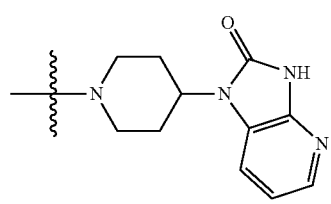

wherein:

Z is selected from:

103
-continued
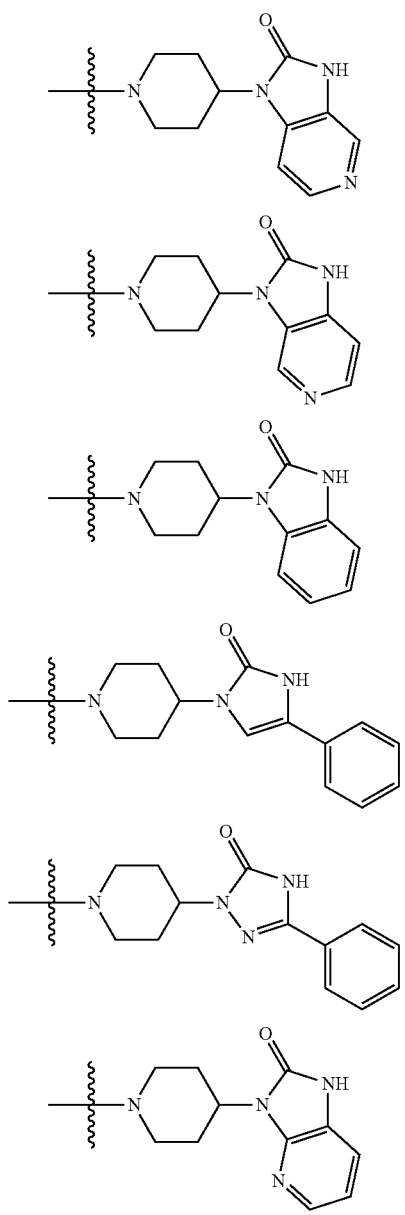
and pharmaceutically acceptable salts and individual stereoisomers thereof.
6. A compound selected from:
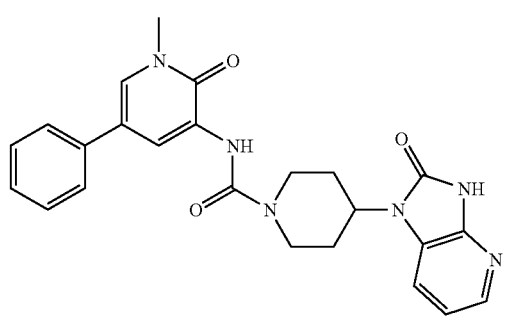
104
-continued
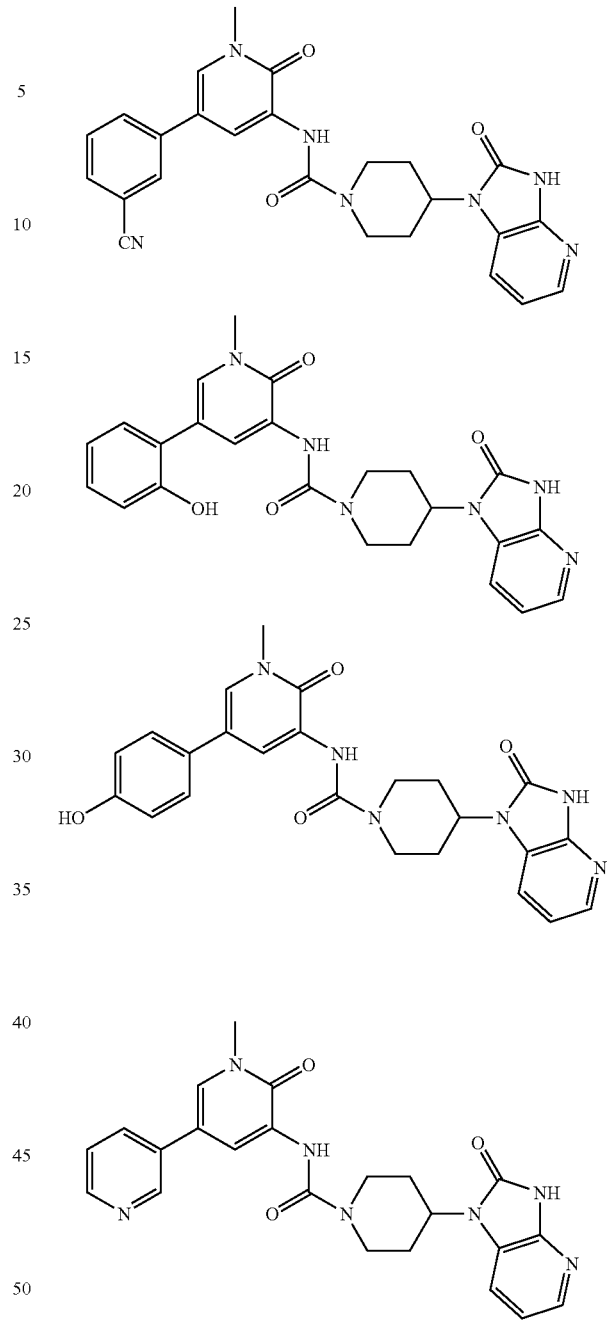
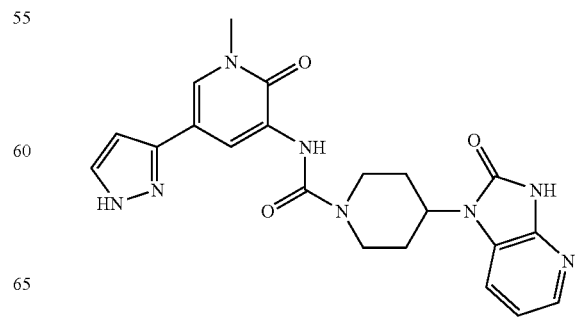

105
-continued
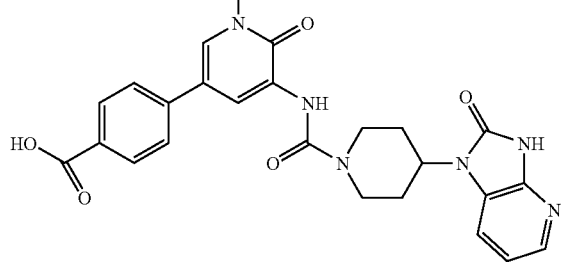
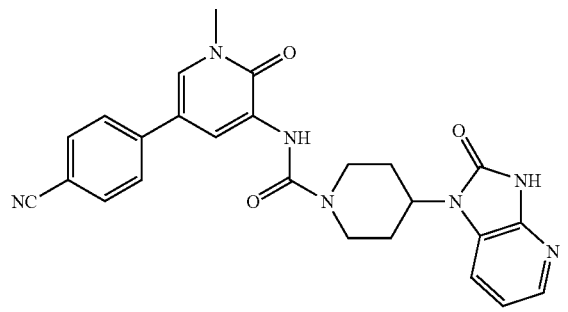
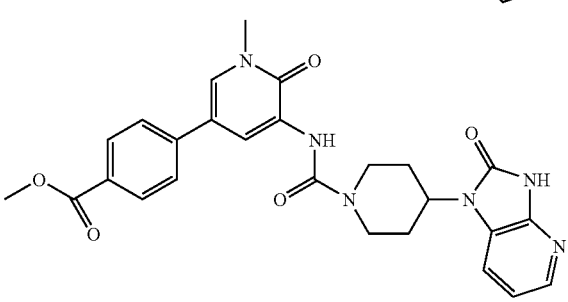
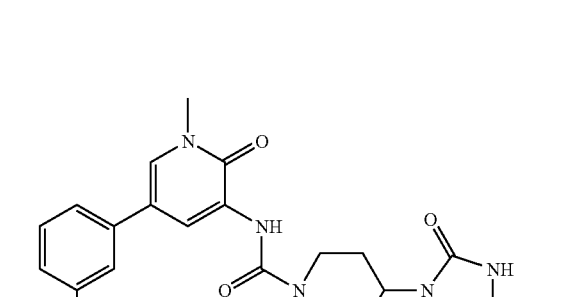
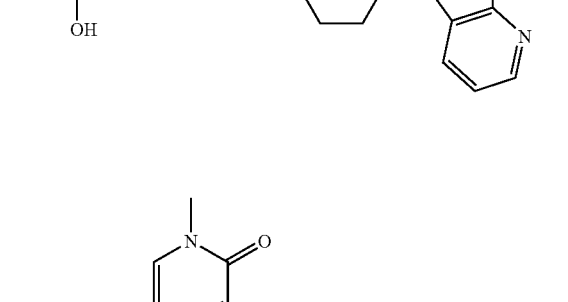
106
-continued
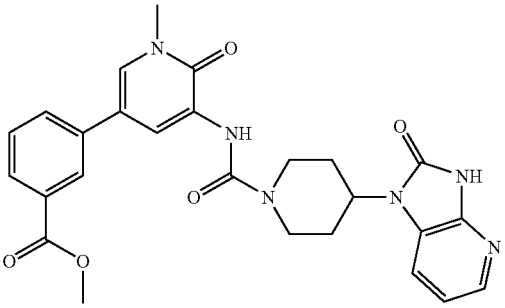
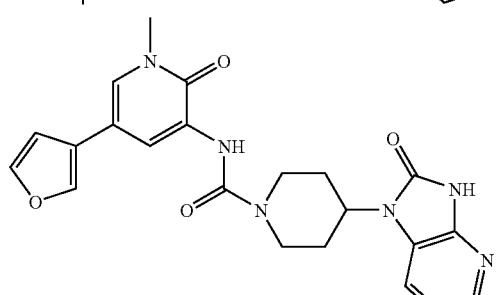
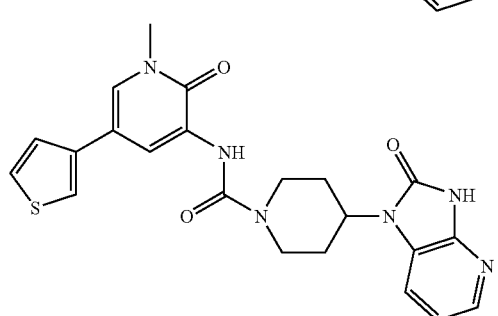
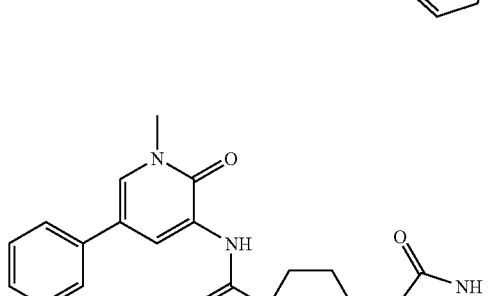
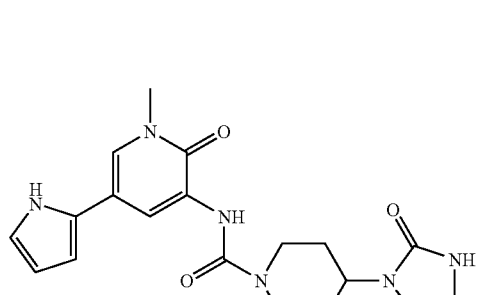

107
-continued
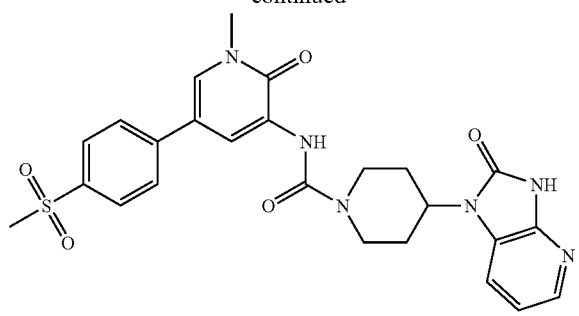
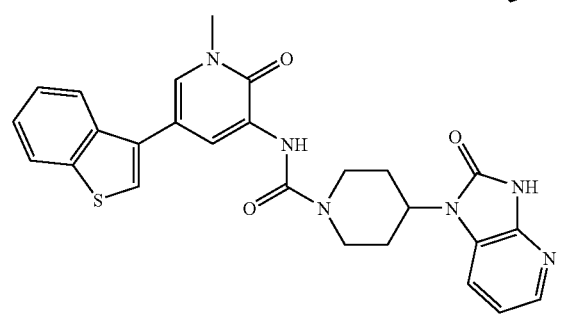
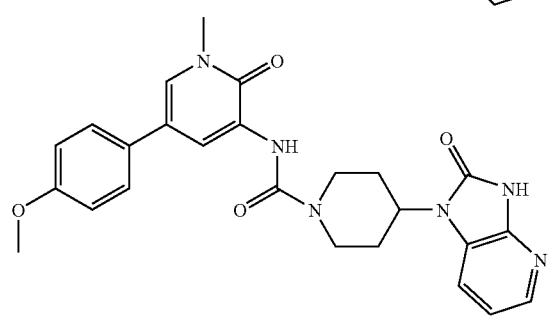
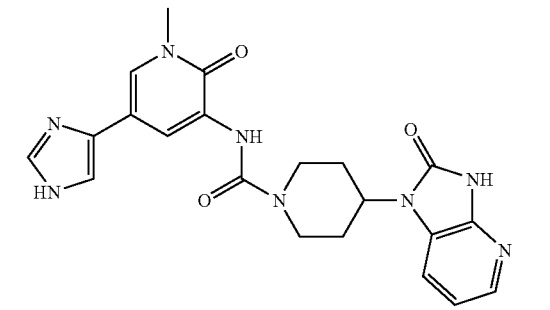
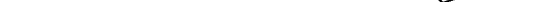
108
-continued
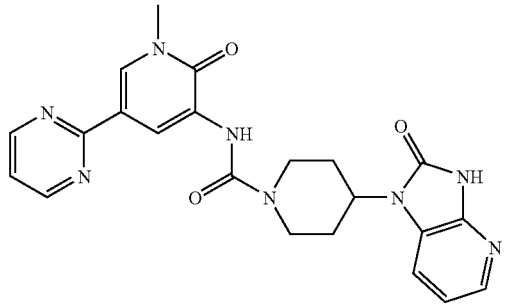
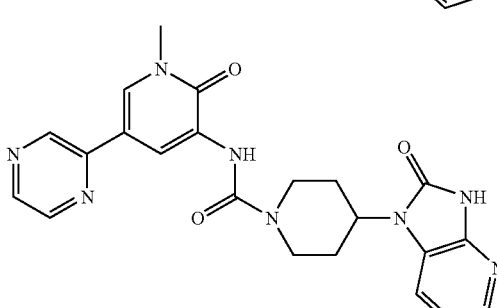
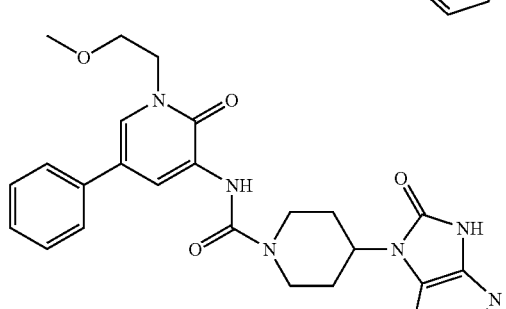
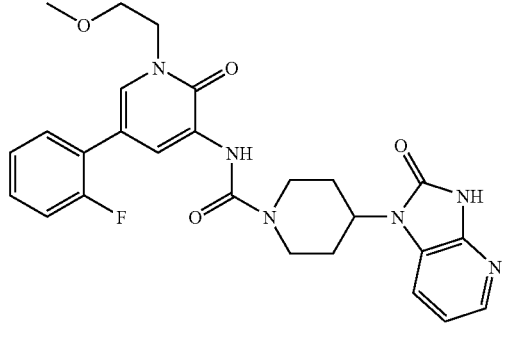
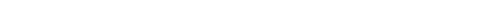

109
-continued
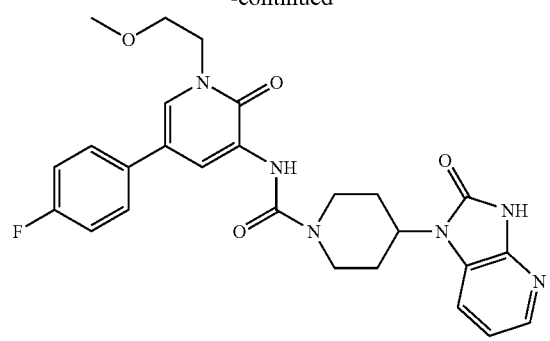
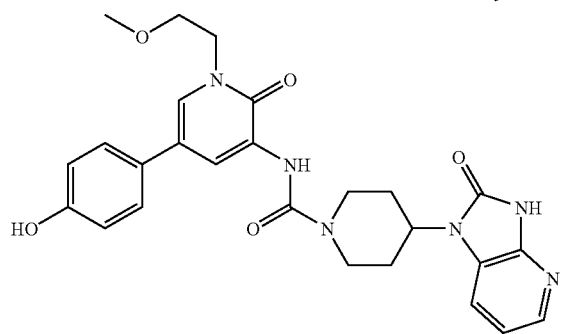
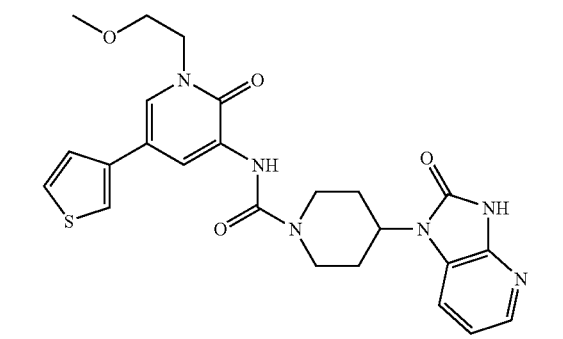
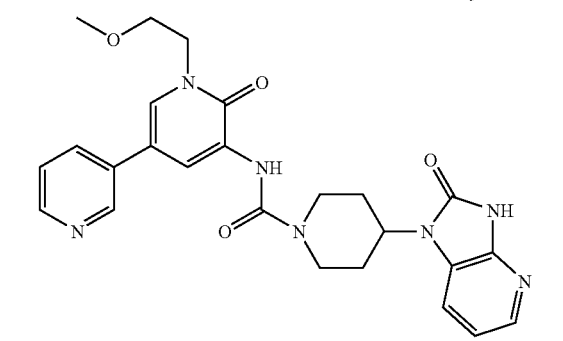
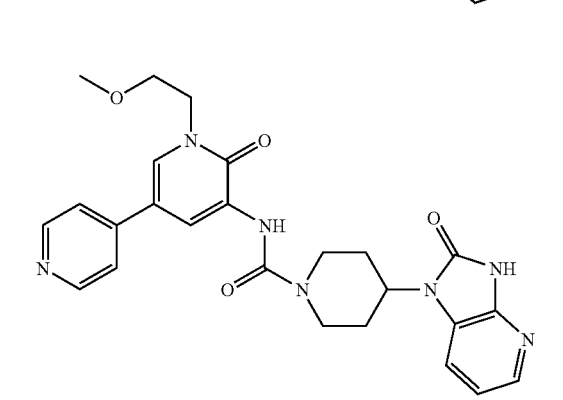
110
-continued
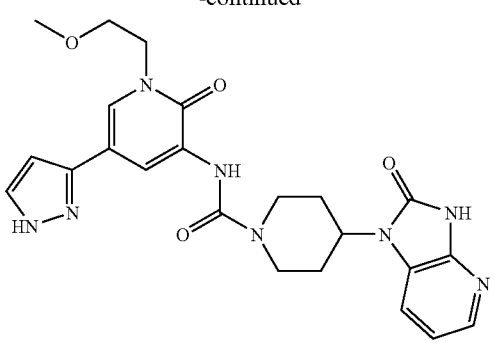
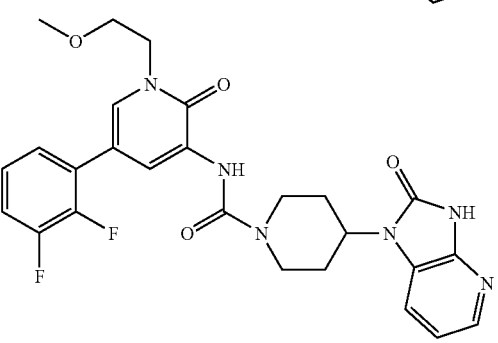
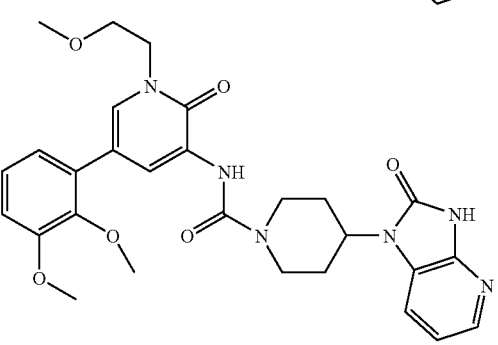
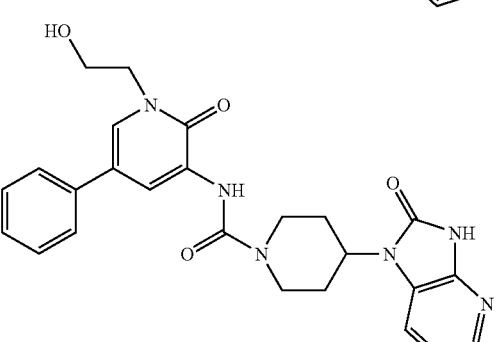
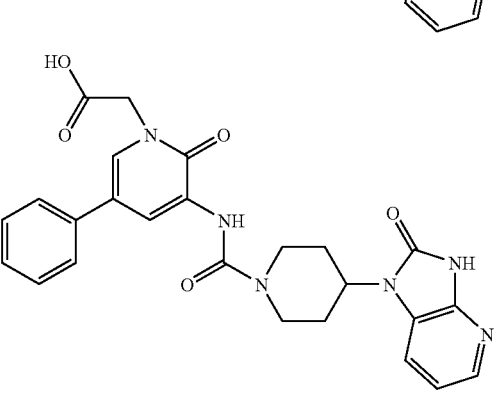

111
-continued
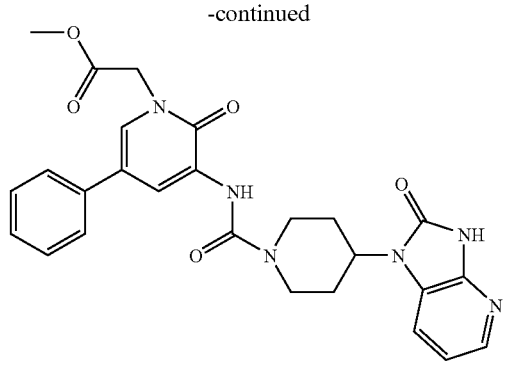
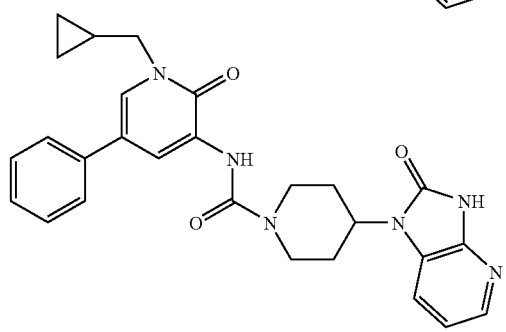
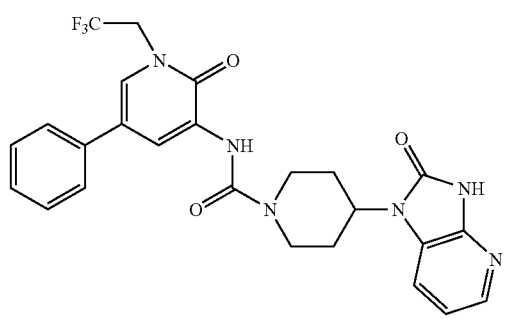
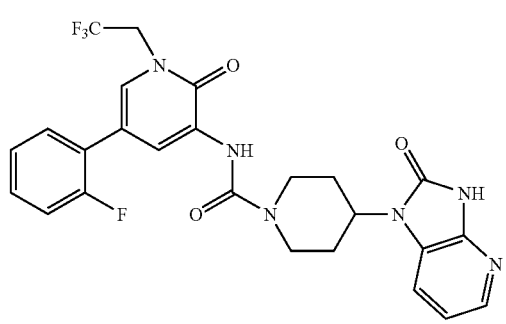
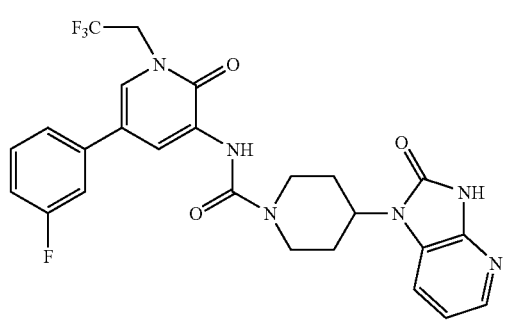
112
-continued
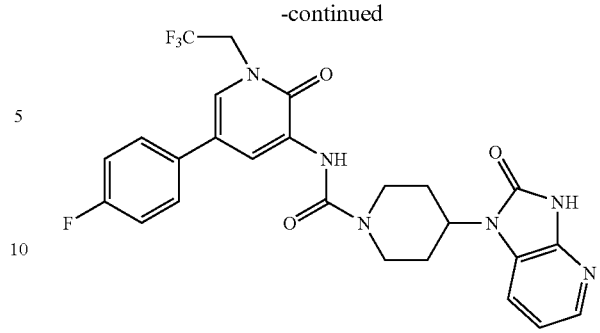
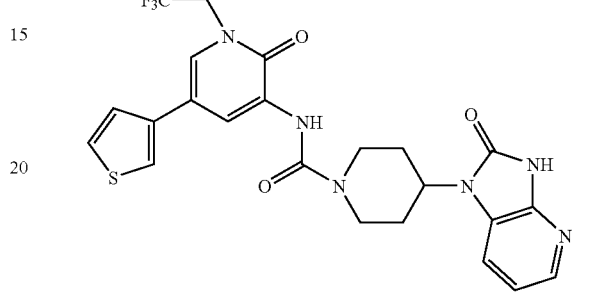
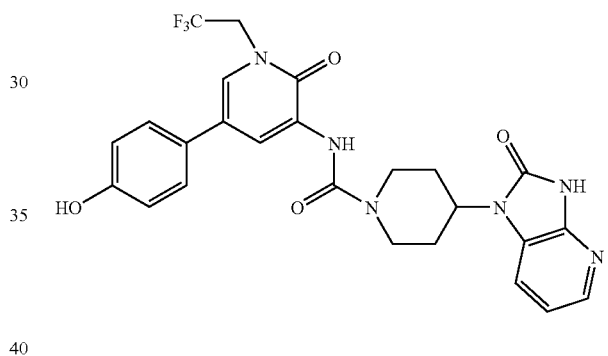
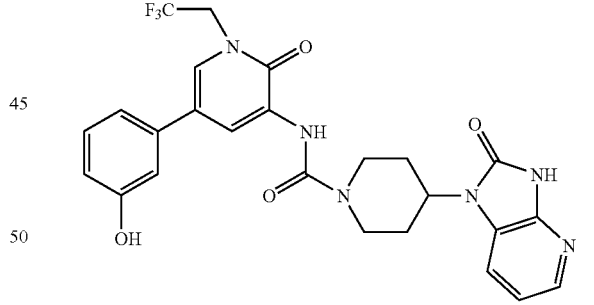
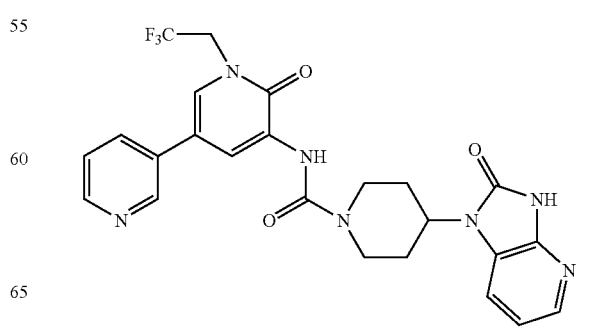

113
-continued
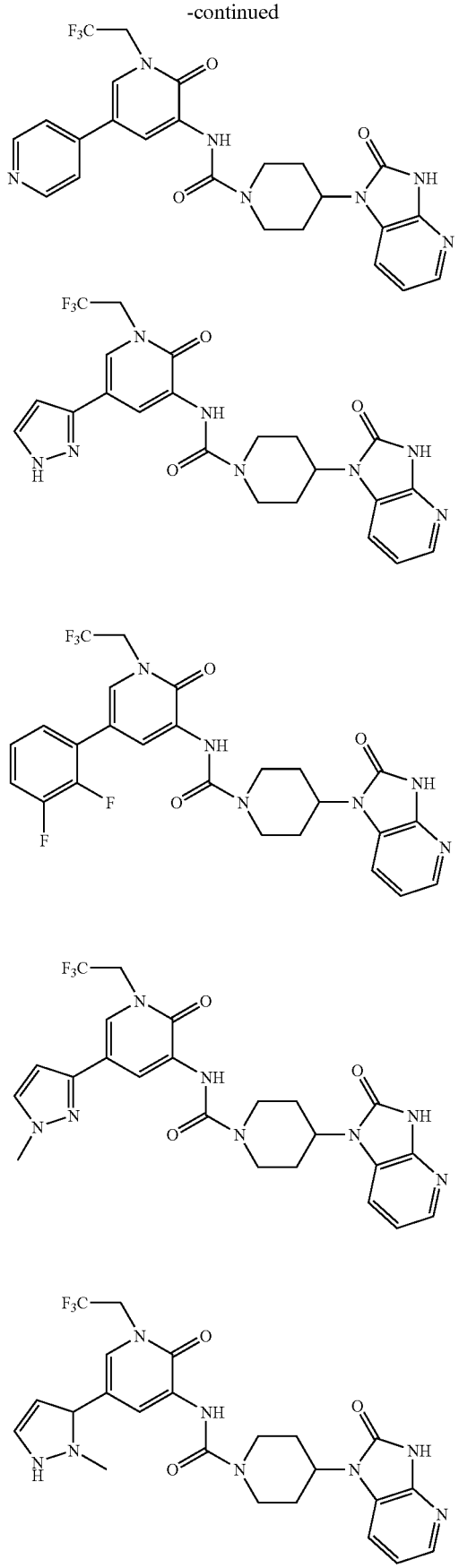
114
-continued
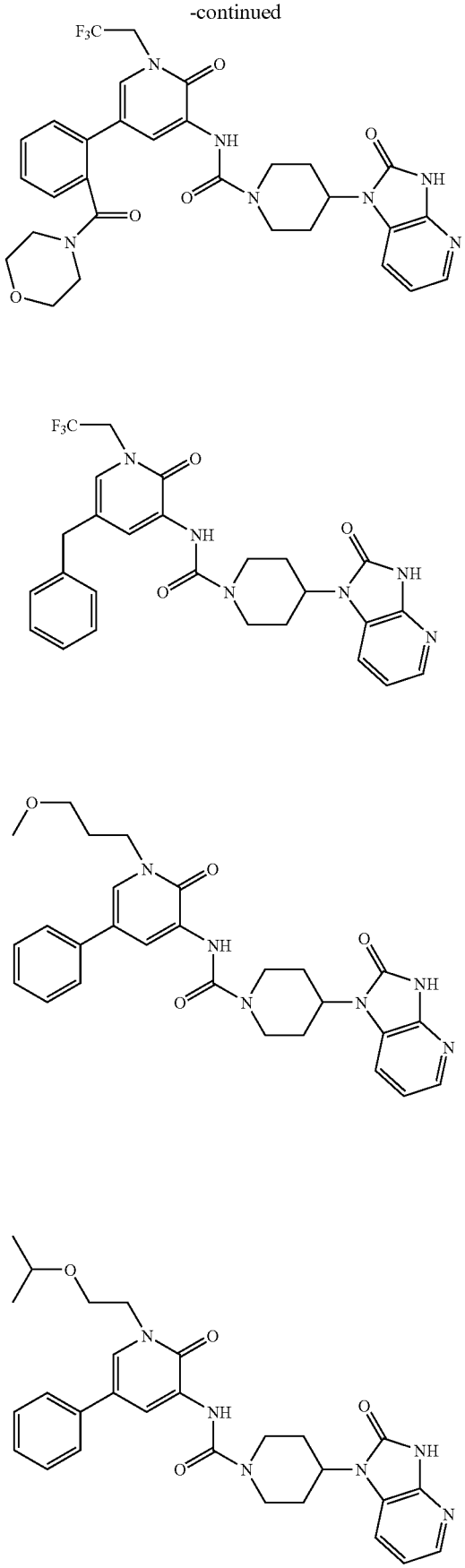

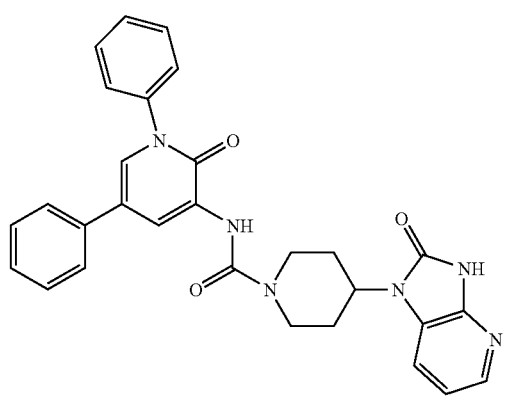
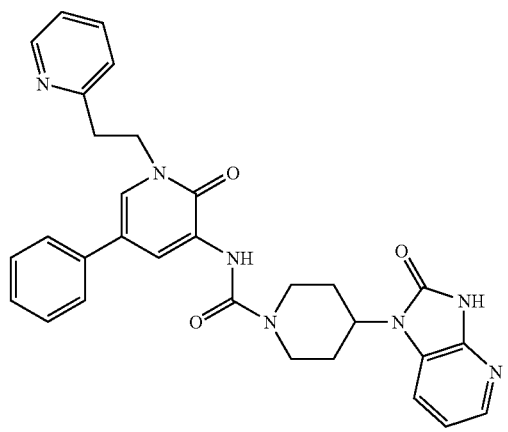
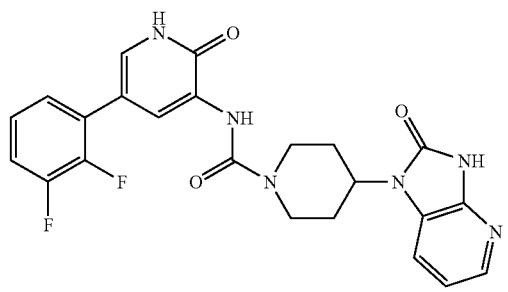
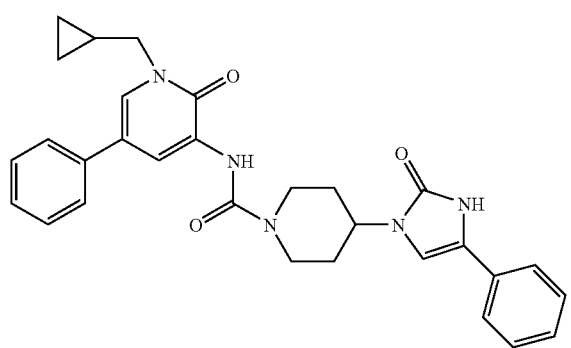
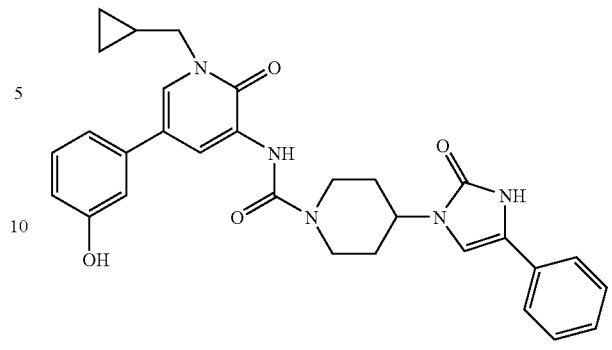
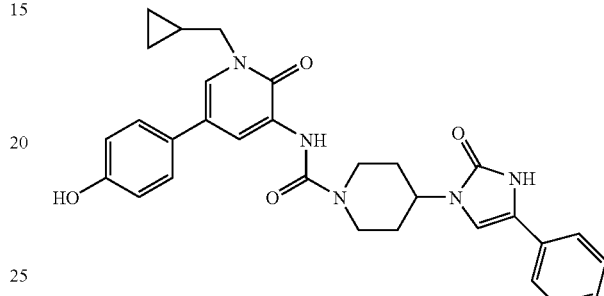
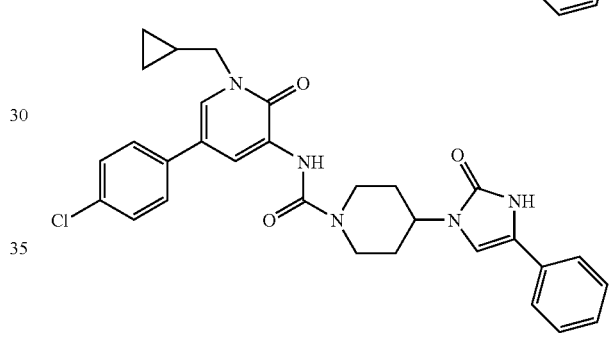
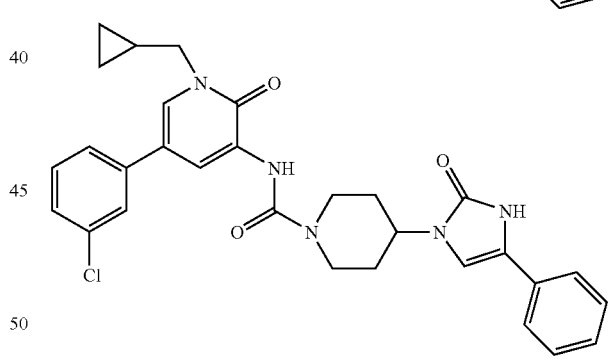
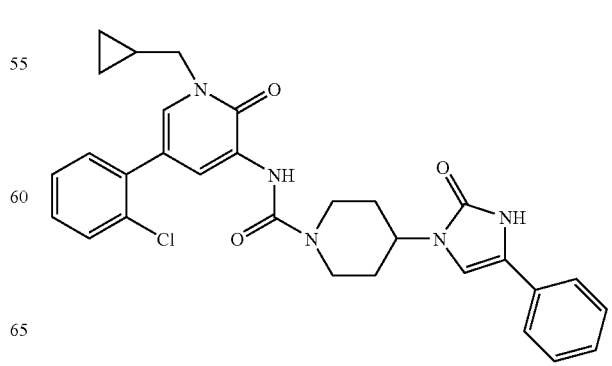

117
-continued
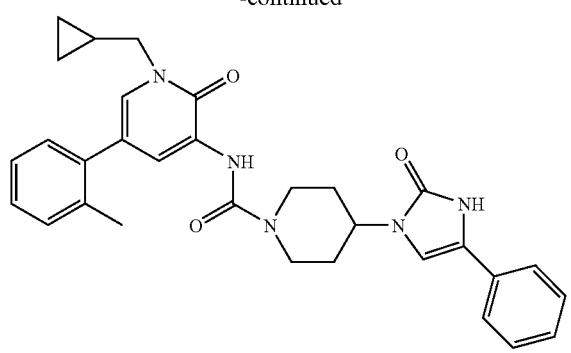
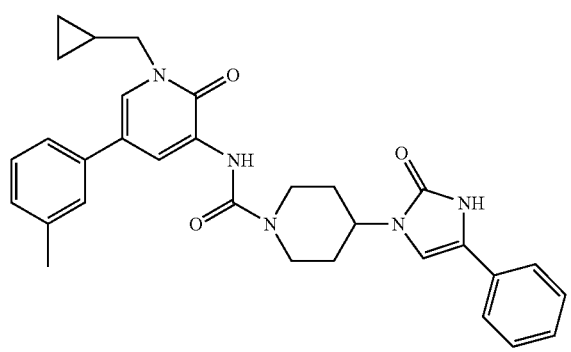
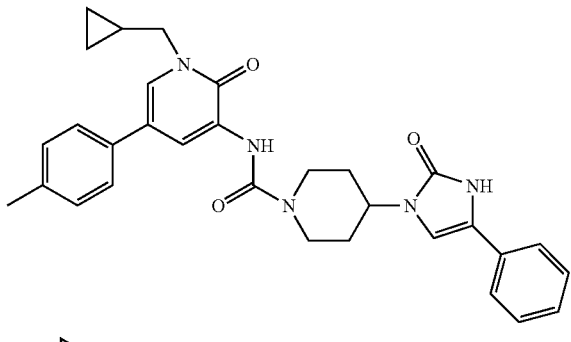
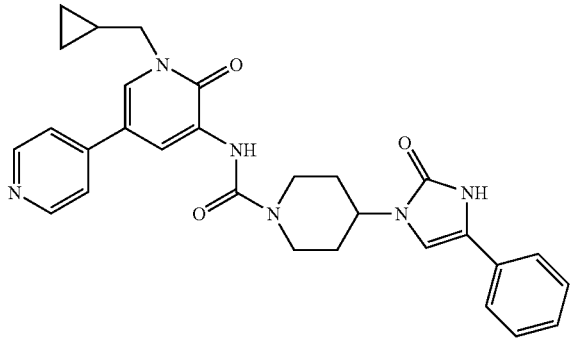
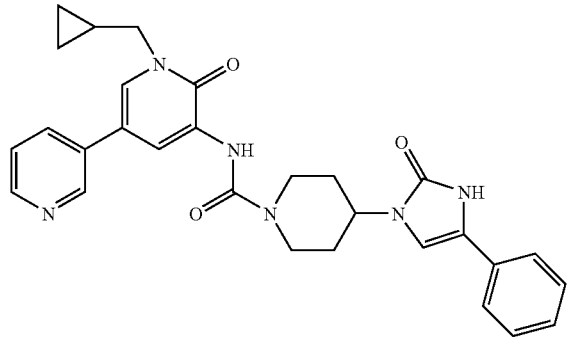
118
-continued
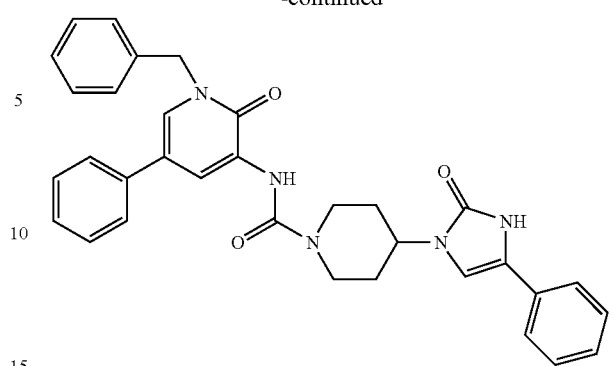
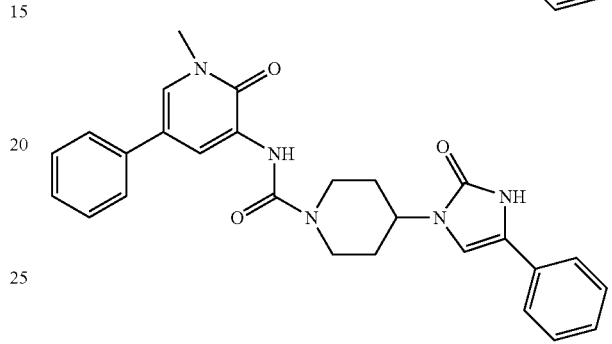
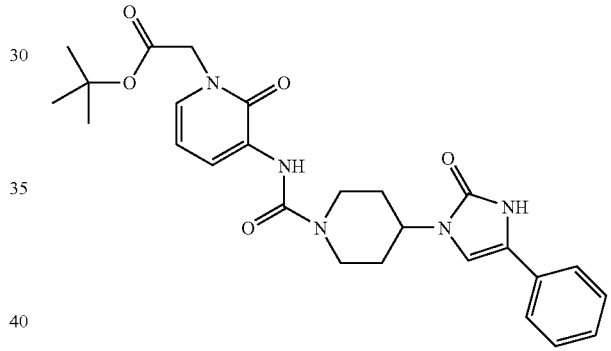
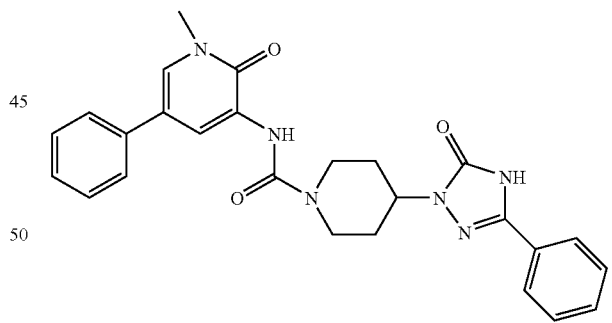
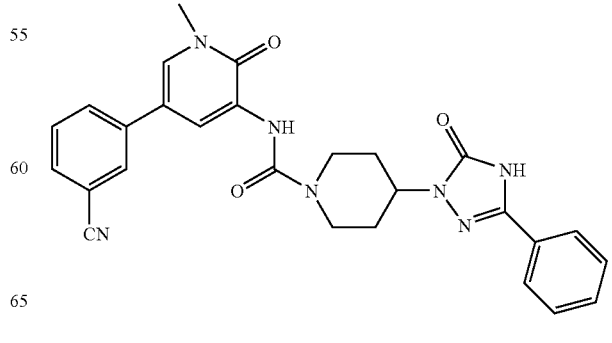

119
-continued
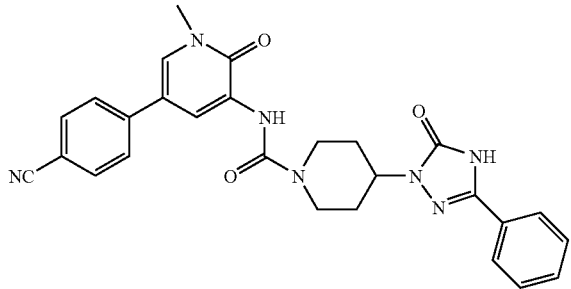
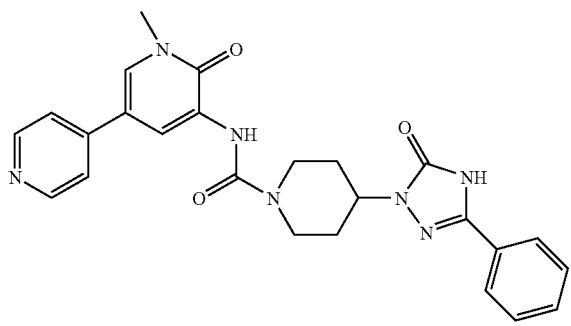
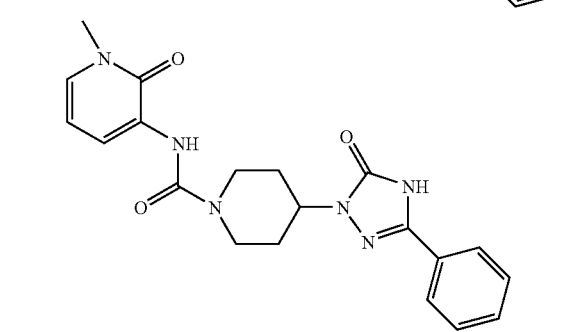
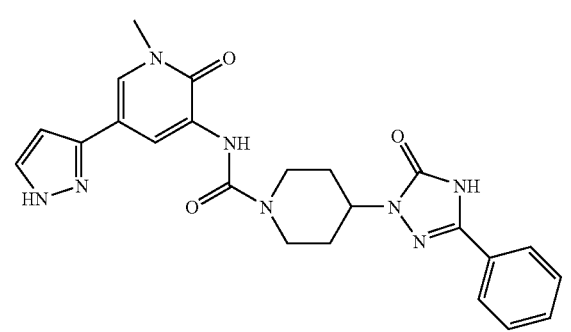
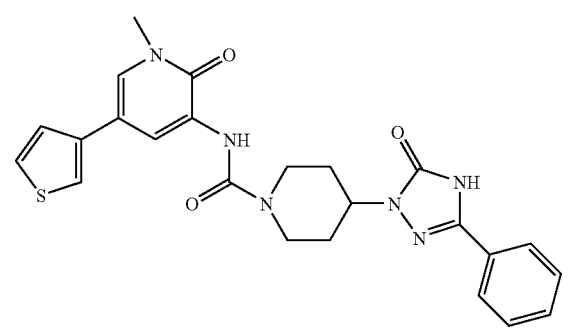
120
-continued
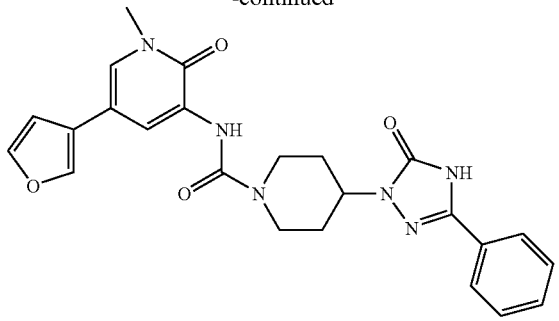
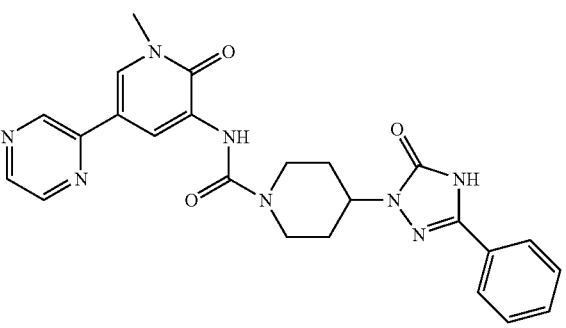
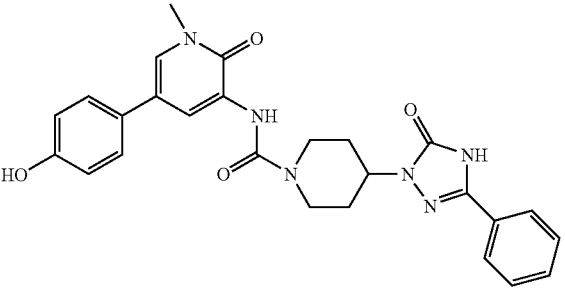

121
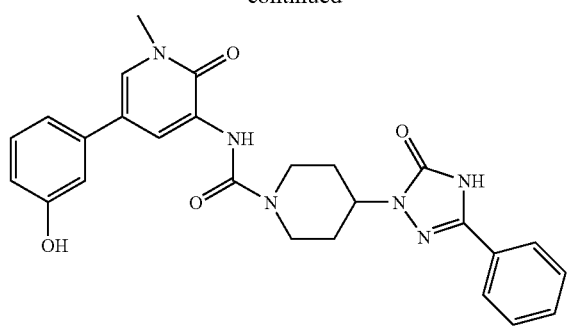
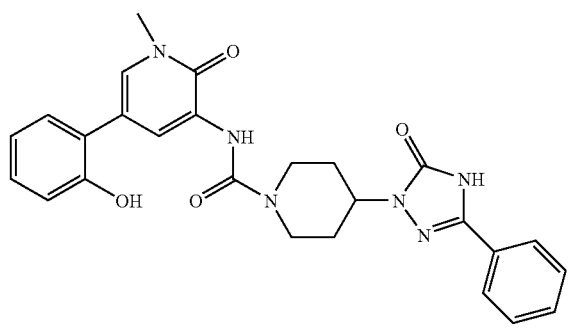
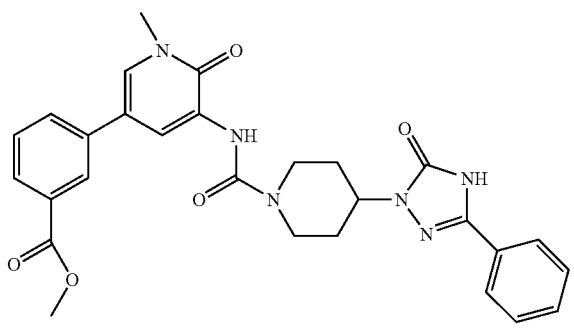
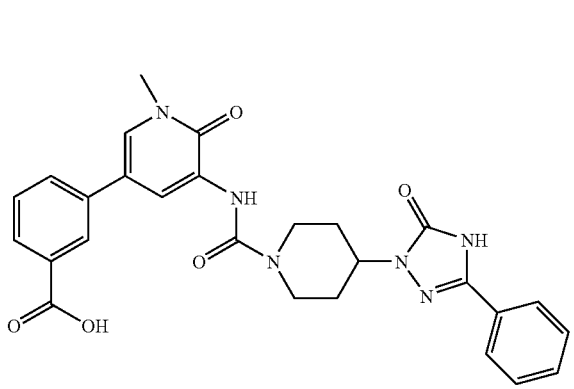
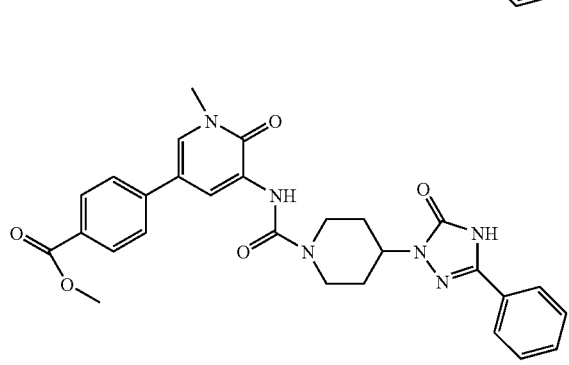
122
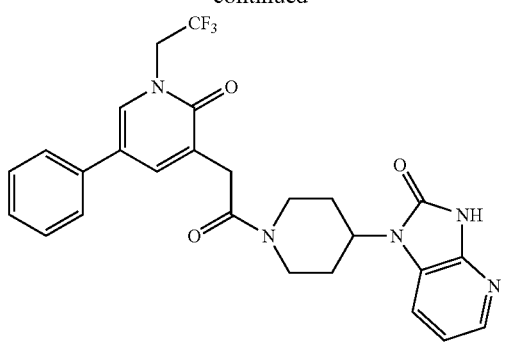
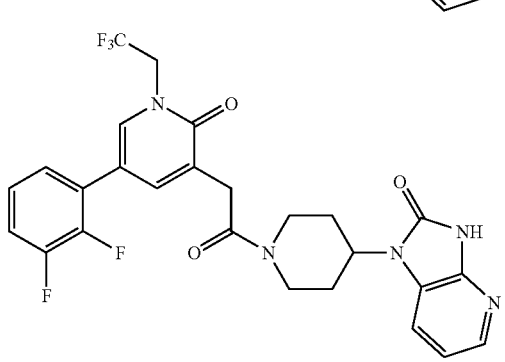
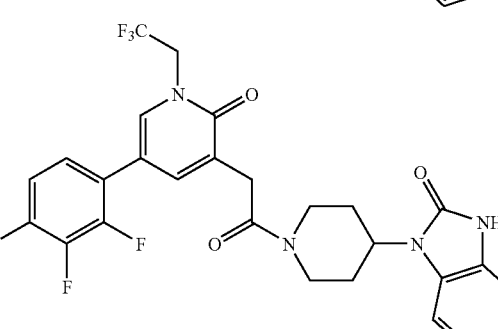
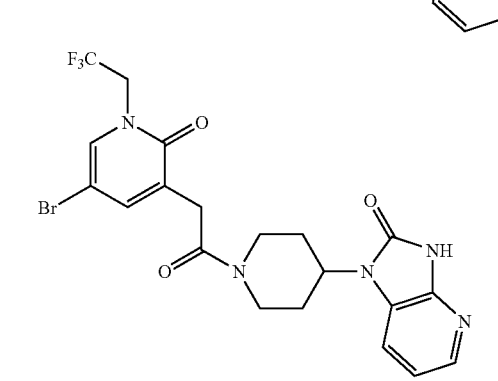
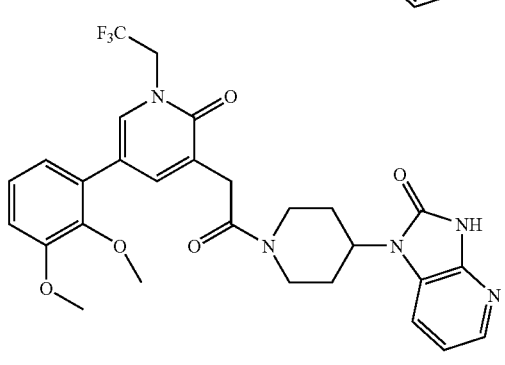

123
-continued
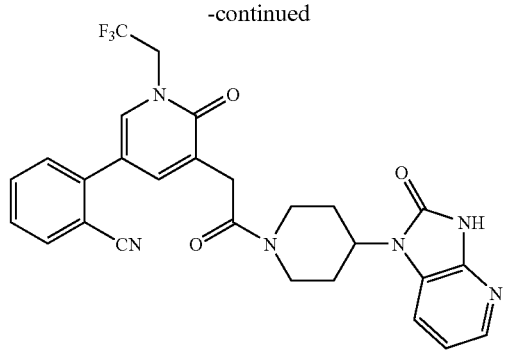
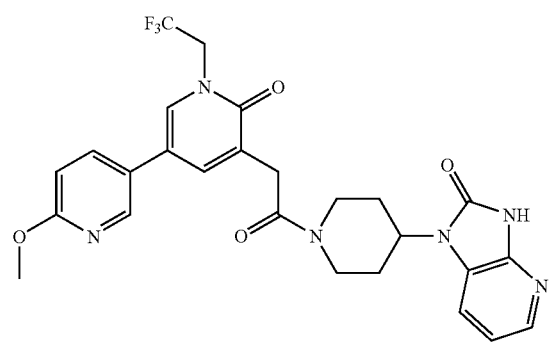
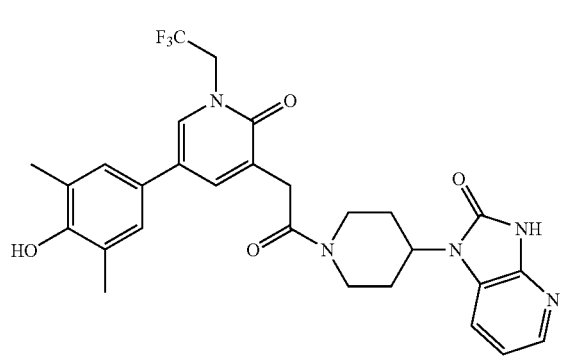
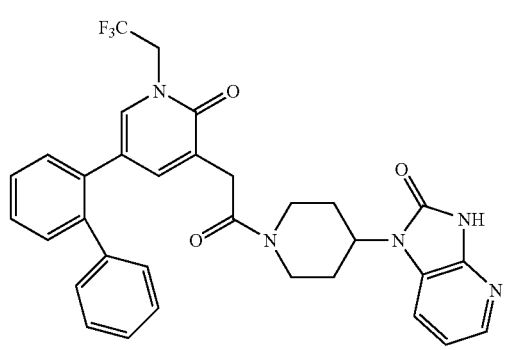
124
-continued
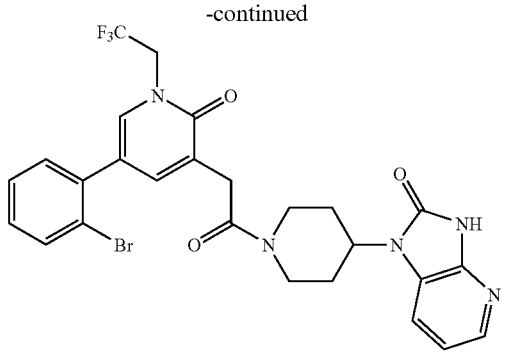
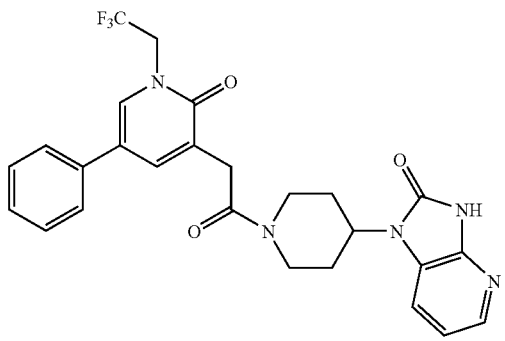
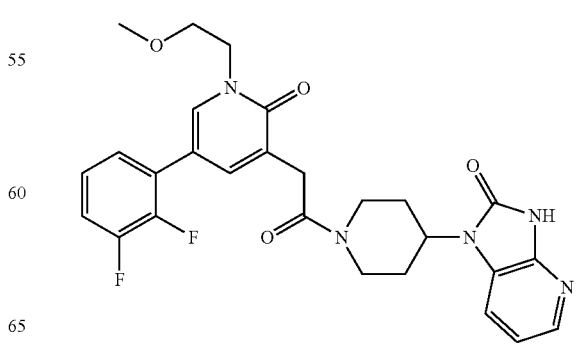

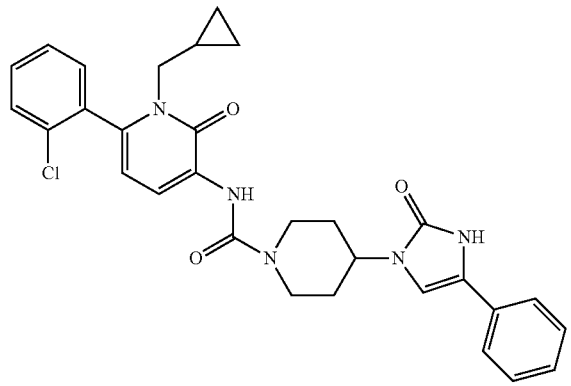
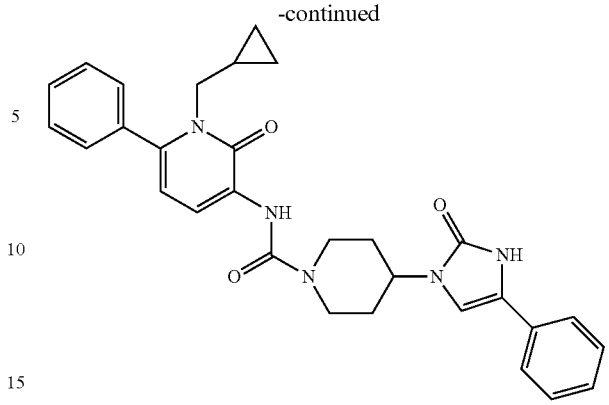
and pharmaceutically acceptable salts and individual stereoisomers thereof.
7. A pharmaceutical composition which comprises an inert carrier and the compound of claim 1.
* * * * *